US009969723B2

(12) United States Patent
Yang et al.

(10) Patent No.: US 9,969,723 B2
(45) Date of Patent: May 15, 2018

(54) 3-(4-(BENZYLOXY)PHENYL)HEX-4-YNOIC ACID DERIVATIVE, METHOD OF PREPARING SAME AND PHARMACEUTICAL COMPOSITION FOR PREVENTING AND TREATING METABOLIC DISEASE INCLUDING SAME AS EFFECTIVE INGREDIENT

(71) Applicant: HYUNDAI PHARM CO., LTD, Cheonan-si (KR)

(72) Inventors: Jin Yang, Yongin-si (KR); Jin Woong Kim, Suwon-si (KR); Han Kyu Lee, Hwaseong-si (KR); Jae Hyun Kim, Yongin-si (KR); Chang Mo Son, Yongin-si (KR); kyu hwan Lee, Ansan-si (KR); Hyung-Ho Choi, Suwon-si (KR); daehoon Kim, Seoul (KR); Tae-Young Ha, Suwon-si (KR); Jaekeol Rhee, Hwaseong-si (KR)

(73) Assignee: HYUNDAI PHARM CO., LTD, Cheonan-si (KR)

( * ) Notice: Subject to any disclaimer, the term of this patent is extended or adjusted under 35 U.S.C. 154(b) by 0 days. days.

(21) Appl. No.: 14/872,745

(22) Filed: Oct. 1, 2015

(65) Prior Publication Data
US 2016/0024063 A1    Jan. 28, 2016

Related U.S. Application Data

(63) Continuation of application No. PCT/KR2014/003355, filed on Apr. 17, 2014.

(51) Int. Cl.
| *A61K 31/497* | (2006.01) |
| *C07D 413/04* | (2006.01) |
| *C07D 213/85* | (2006.01) |
| *C07D 215/06* | (2006.01) |
| *C07D 217/04* | (2006.01) |
| *C07D 221/20* | (2006.01) |
| *C07D 317/72* | (2006.01) |
| *C07D 239/42* | (2006.01) |
| *C07D 271/07* | (2006.01) |
| *C07D 277/82* | (2006.01) |
| *C07D 209/44* | (2006.01) |
| *C07D 211/14* | (2006.01) |

(Continued)

(52) U.S. Cl.
CPC .......... *C07D 413/04* (2013.01); *C07C 51/367* (2013.01); *C07C 51/373* (2013.01); *C07C 59/72* (2013.01); *C07C 59/90* (2013.01); *C07D 207/06* (2013.01); *C07D 209/44* (2013.01); *C07D 211/14* (2013.01); *C07D 211/70* (2013.01); *C07D 213/74* (2013.01); *C07D 213/85* (2013.01); *C07D 215/04* (2013.01); *C07D 215/06* (2013.01); *C07D 217/04* (2013.01); *C07D 217/24* (2013.01); *C07D 221/20* (2013.01); *C07D 239/28* (2013.01); *C07D 239/42* (2013.01); *C07D 271/07* (2013.01); *C07D 277/82* (2013.01); *C07D 295/073* (2013.01); *C07D 295/096* (2013.01); *C07D 295/155* (2013.01); *C07D 317/72* (2013.01)

(58) Field of Classification Search
USPC ...................................................... 514/252.14
See application file for complete search history.

(56) References Cited

U.S. PATENT DOCUMENTS

| 7,338,960 B2 | 3/2008 | Bell et al. |
| 7,649,110 B2 | 1/2010 | Akerman et al. |
(Continued)

FOREIGN PATENT DOCUMENTS

| KR | 1020010034586 A | 9/1999 |
| WO | WO 2005/086661 A2 | 9/2005 |
(Continued)

OTHER PUBLICATIONS

Greene and Wuts "Protective Groups in Organic Synthesis," *Wiley-Interscience* Third Edittion:312-319 (1999).

(Continued)

*Primary Examiner* — Marcos L Sznaidman
(74) *Attorney, Agent, or Firm* — Klarquist Sparkman, LLP

(57) ABSTRACT

The present invention relates to a novel 3-(4-(benzyloxy) phenyl)hex-4-inoic acid derivative, a preparation method thereof, and a pharmaceutical composition comprising the same as an active ingredient for the prevention and treatment of metabolic disease. The novel 3-(4-(benzyloxy)phenyl) hex-4-inoic acid derivative, the optical isomer thereof, or the pharmaceutically acceptable salt thereof of the present invention has excellent activities of activating GPR40 protein and promoting insulin secretion accordingly but has no toxicity when co-administered with other drugs. That is, the novel 3-(4-(benzyloxy)phenyl)hex-4-inoic acid derivative, the optical isomer thereof, or the pharmaceutically acceptable salt thereof of the present invention can be co-administered with other drugs and can promote the activation of GPR40 protein significantly, so that the composition comprising the same as an active ingredient can be efficiently used as a pharmaceutical composition for the prevention and treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

14 Claims, 2 Drawing Sheets

(51) Int. Cl.

| | |
|---|---|
| *C07D 295/073* | (2006.01) |
| *C07D 295/096* | (2006.01) |
| *C07C 51/367* | (2006.01) |
| *C07C 51/373* | (2006.01) |
| *C07C 59/72* | (2006.01) |
| *C07C 59/90* | (2006.01) |
| *C07D 207/06* | (2006.01) |
| *C07D 211/70* | (2006.01) |
| *C07D 213/74* | (2006.01) |
| *C07D 215/04* | (2006.01) |
| *C07D 217/24* | (2006.01) |
| *C07D 239/28* | (2006.01) |
| *C07D 295/155* | (2006.01) |

(56) References Cited

U.S. PATENT DOCUMENTS

| | | |
|---|---|---|
| 8,299,296 B2 | 10/2012 | Shimada et al. |
| 2007/0213364 A1 | 9/2007 | Yasuma et al. |

FOREIGN PATENT DOCUMENTS

| | | | |
|---|---|---|---|
| WO | WO 2005/095338 | | 10/2005 |
| WO | WO 2008/030520 | | 3/2008 |
| WO | WO 2008/030618 A1 | | 3/2008 |
| WO | WO 2011/046851 | * | 4/2011 |
| WO | WO 2011/046851 A1 | | 4/2011 |
| WO | WO 2015/097713 | * | 7/2015 |

OTHER PUBLICATIONS

Telvekar and Kundaikar, "GPR40 Carboxylic Acid Receptor Family and Diabetes: A New Drug Target" *Current Drug Targets* 9(10):899-910 (2008) (Abstract).

Walker et al. "Development of a Scalable Synthesis of a GPR40 Receptor Agonist," *Organic Process Research & Development* 15:570-580 (2011).

Ferdaoussi et al. "Free Fatty Acid Receptor 1: A New Drug Target for Type 2 Diabetes?," *Canadian Journal of Diabetes* 36:275-280 (2012).

Houze et al., "AMG 837: A potent, orally bioavailable GPR40 agonist," *Bioorganic & Medicinal Chemistry Letters*, 22 (2012) 1267-1270.

Lu et al., "Molecular docking and molecular dynamics simulation studies of GPR40 receptor-agonist interactions," *Journal of Molecular Graphics and Modelling*, vol. 28, pp. 766-774, 2010.

* cited by examiner

【Figure 1】
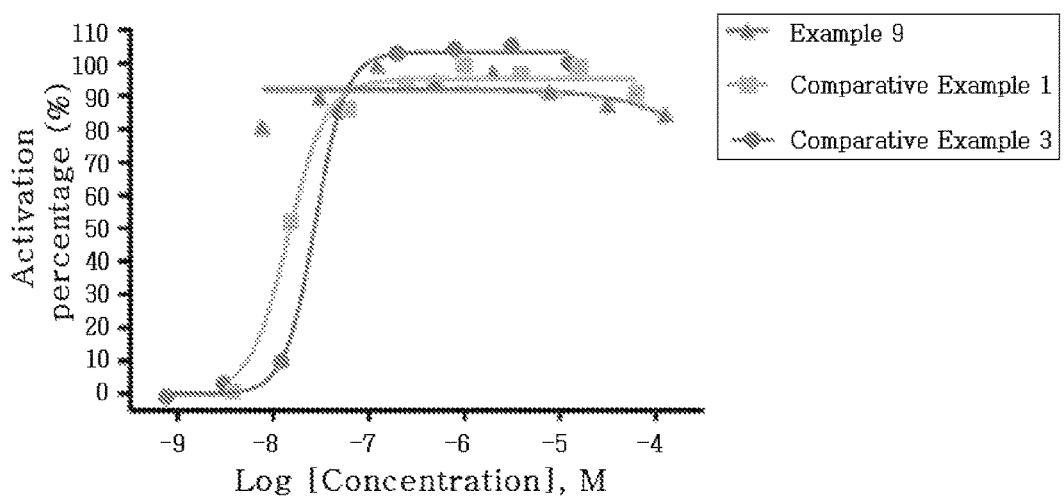

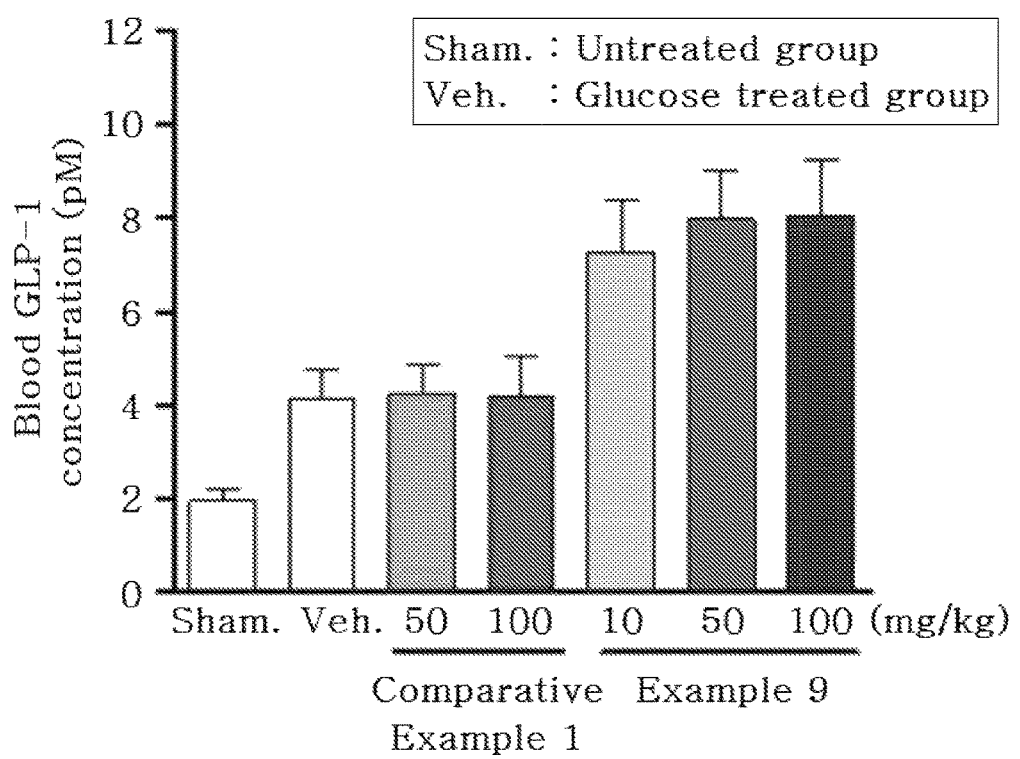
[Figure 2]

3-(4-(BENZYLOXY)PHENYL)HEX-4-YNOIC ACID DERIVATIVE, METHOD OF PREPARING SAME AND PHARMACEUTICAL COMPOSITION FOR PREVENTING AND TREATING METABOLIC DISEASE INCLUDING SAME AS EFFECTIVE INGREDIENT

CROSS-REFERENCES TO RELATED APPLICATION

This is a continuation of International Application No. PCT/KR2014/003355, filed Apr. 17, 2014, which in turn claims the benefit of priority from Korean Patent Application No. 10-2013-0043100, filed on Apr. 18, 2013 and Korean Patent Application No. 10-2014-0045343, filed on Apr. 16, 2014. The Korean applications are incorporated herein in their entirety.

BACKGROUND OF THE INVENTION

1. Field of the Invention

The present invention relates to a novel 3-(4-(benzyloxy)phenyl)hex-4-inoic acid derivative, a preparation method thereof, and a pharmaceutical composition for the prevention and treatment of metabolic disease comprising the same as an active ingredient.

2. Description of the Related Art

Diabetes is a serious disease that continually threatens our health and at least a hundred million people have been suffering over the world. Diabetes can be classified into two clinical symptom categories, which are type I diabetes and type II diabetes. Type I diabetes, informed as insulin-dependent diabetes mellitus (IDDM), is caused by autoimmune destruction of pancreatic beta cells that produce insulin, so that it requires regular administration of exogenous insulin. Type II diabetes, informed as non insulin-dependent diabetes mellitus (NIDDM), is resulted from the defect in regulating blood sugar. So, those people who have type II diabetes characteristically show defect in insulin secretion or insulin resistance, suggesting that they hardly have insulin secreted in vivo or cannot utilize insulin efficiently.

Diabetes is characterized by high concentration of glucose in blood and urine, by which this disease causes polyuria, thirst, hunger, and other lipid and protein metabolism related problems. Diabetes can cause life threatening complications such as vision loss, renal failure, and heart disease. Diabetes is also a reason of retinal damage, and increases the risk of cataract and glaucoma. Diabetes also lowers response to the pain relating to nerve injury in legs and feet and can be a reason of significant infection.

Recent drugs to treat diabetes are insulin, insulin-secretagogue, glucose lowering effector, peroxisome proliferator-activated receptor activator, etc. However, recent treatment methods have problems of inducing low blood sugar, increasing body weight, losing reactivity to the treatment drug over the time, causing gastro-intestinal tract problems and edema, etc. Therefore, studies have been undergoing to introduce a more effective and efficient treatment method. One of those attempts is to use G-protein coupled receptor (GPCR).

GPR40 has recently been identified as one of G-protein coupled receptor (GPCR). It is known as free fatty acid receptor I, which is over-expressed in β-cells in pancreas. Intracellular calcium concentration is increased by such compound that activates GPR40 (FFAR1) and accordingly glucose-stimulated insulin secretion (GSIS) is promoted (Current Drug Targets, 2008, 9, 899-910). When the GPR40 activator was introduced in a normal mouse or a transgenic mouse being apt to have diabetes and glucose tolerance test followed, it showed increased glucose tolerance. The treated mouse demonstrated a short-term increase of insulin in blood plasma. It was confirmed from the study on the functions of GPR40 that free fatty acid which is the ligand of GPR40 was acting in pancreatic β cells, and as a result the β cells secreted insulin glucose concentration dependently. From the analysis with GPR knockout mouse, it was confirmed that GPR40 was involved in obesity and diabetes (Can J Diabetes 2012, 36, 275-280). Therefore, GPR40 is regarded as a novel target of diabetes study.

In the course of study on GPR40 activator, the present inventors confirmed that a novel 3-(4-(benzyloxy)phenyl)hex-4-inoic acid derivative, a pharmaceutically acceptable salt thereof, or an optical isomer of the same had GPR40 related activity, resulting in the confirmation of excellent in vivo effect such as the increase of intracellular calcium concentration and the effect of lowering blood glucose, leading to the completion of this invention.

SUMMARY

It is an object of the present invention to provide a novel 3-(4-(benzyloxy)phenyl)hex-4-inoic acid derivative, an optical isomer thereof, or a pharmaceutically acceptable salt thereof.

It is another object of the present invention to provide a method for preparing the said 3-(4-(benzyloxy)phenyl)hex-4-inoic acid derivative.

It is also an object of the present invention to provide a pharmaceutical composition comprising the said 3-(4-(benzyloxy)phenyl)hex-4-inoic acid derivative as an active ingredient for the prevention or treatment of metabolic disease.

To achieve the above objects, the present invention provides the compound represented by the below formula 1, the optical isomer thereof, or the pharmaceutically acceptable salt of the same.

[Formula 1]

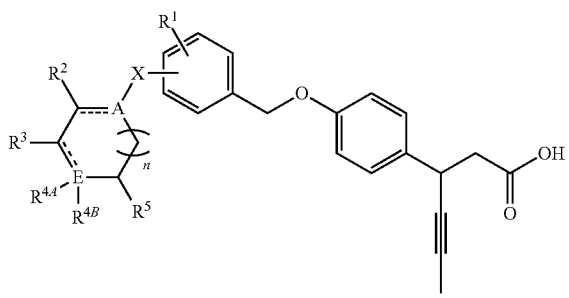

(In formula 1, ═══ is single bond or double bond;
A and E are independently C, N, or O;
n is an integer of 0-5;
X is single bond, or $C_{1-10}$ straight or branched alkylene;
$R^1$ is —H, —OH, halogen, $C_{1-10}$ straight or branched alkyl, $C_{1-10}$ straight or branched alkoxy, $C_{5-10}$ cycloalkyl, or $C_{5-10}$ cycloalkenyl;
$R^2$, $R^3$, and $R^5$ are independently —H, —OH, halogen, $C_{1-10}$ straight or branched alkyl, or $C_{1-10}$ straight or branched alkoxy;

Wherein, $R^2$ and $R^3$ can form $C_{5-10}$ cycloalkyl, $C_{6-10}$ aryl, 5-10 membered heterocycloalkyl or 5-10 membered heteroaryl along with atoms which are conjugated to the same. The 5-10 membered heterocycloalkyl can contain one or more hetero atoms selected from the group consisting of N, O, and S, and the 5-10 membered heteroaryl can contain one or more hetero atoms selected from the group consisting of N, O, and S;

$R^{4A}$ is —H, —OH, =O, unsubstituted or substituted $C_{6-10}$ aryl, or unsubstituted or substituted 5-10 membered heteroaryl containing one or more hetero atoms selected from the group consisting of N, O, and S.

In the said substituted $C_{6-10}$ aryl and the substituted 5-10 membered heteroaryl, one or more substituents selected from the group consisting of —OH, halogen, nitrile, unsubstituted or substituted $C_{1-5}$ straight or branched alkyl in which one or more halogens are substituted, unsubstituted or substituted $C_{1-5}$ straight or branched alkoxy in which one or more halogens are substituted, $C_{1-10}$ straight or branched alkylsulfonyl,

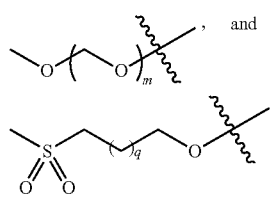

can be substituted, wherein m and q are independently integers of 1-10,

In the said unsubstituted or substituted 5-10 membered heteroaryl, phenyl can be fused;

Wherein, $R^3$ and $R^{4A}$ can form $C_{5-10}$ cycloalkyl, $C_{6-10}$ aryl, 5-10 membered heterocycloalkyl or 5-10 membered heteroaryl along with atoms which are conjugated to the same. The 5-10 membered heterocycloalkyl can contain one or more hetero atoms selected from the group consisting of N, O, and S, and the 5-10 membered heteroaryl can contain one or more hetero atoms selected from the group consisting of N, O, and S;

In the said $C_{5-10}$ cycloalkyl, $C_{6-10}$ aryl, 5-10 membered heterocycloalkyl, and 5-10 membered heteroaryl, $C_{1-5}$ straight or branched alkoxy can be substituted;

$R^{4B}$ is absent or can form 5-10 membered heterocycle containing one or more hetero atoms selected from the group consisting of N, O, and S along with atoms which are conjugated to the same and $R^{4A}$).

The present invention also provides a method for preparing the compound represented by formula 1 comprising the following steps as shown in the below reaction formula 1:

preparing the compound represented by formula 4 by condensation reaction of the compound represented by formula 2 and the compound represented by formula 3 (step 1); and preparing the compound represented by formula 1 by reduction reaction of the compound represented by formula 4 prepared in step 1) (step 2).

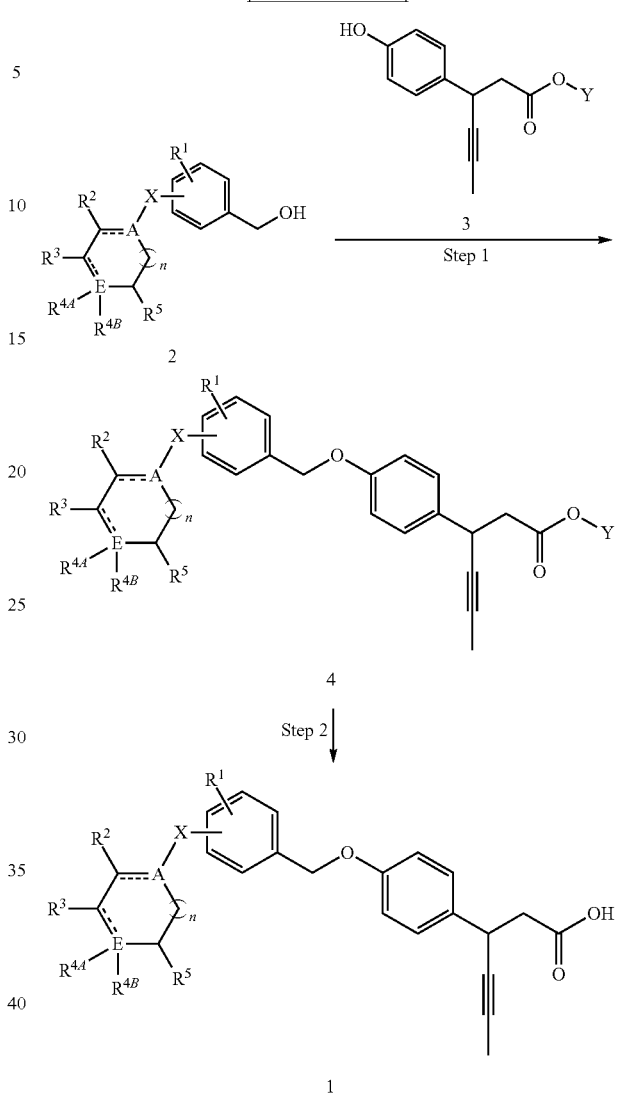

(In reaction formula 1, $R^1$, $R^2$, $R^3$, $R^{4A}$, $R^{4B}$, $R^5$, A, E, n, $\cdots$, and X are as defined in formula 1; and Y is $C_{1-10}$ straight or branched alkyl).

Further, the present invention provides a method for preparing the compound represented by formula 1 of claim 1 comprising the following steps as shown in the below reaction formula 3;

preparing the compound represented by formula 6 by coupling reaction of the compound represented by formula 5 and the compound represented by formula 3 (step 1);

preparing the compound represented by formula 7 by mesylate reaction of the compound represented by formula 6 prepared in step 1) (step 2);

preparing the compound represented by formula 4 by replacing the mesylate site of the compound represented by formula 7 prepared in step 2) with the compound represented by formula 13 (step 3); and preparing the compound represented by formula 1 by reduction reaction of the compound represented by formula 4 prepared in step 3) (step 4).

[Reaction Formula 3]

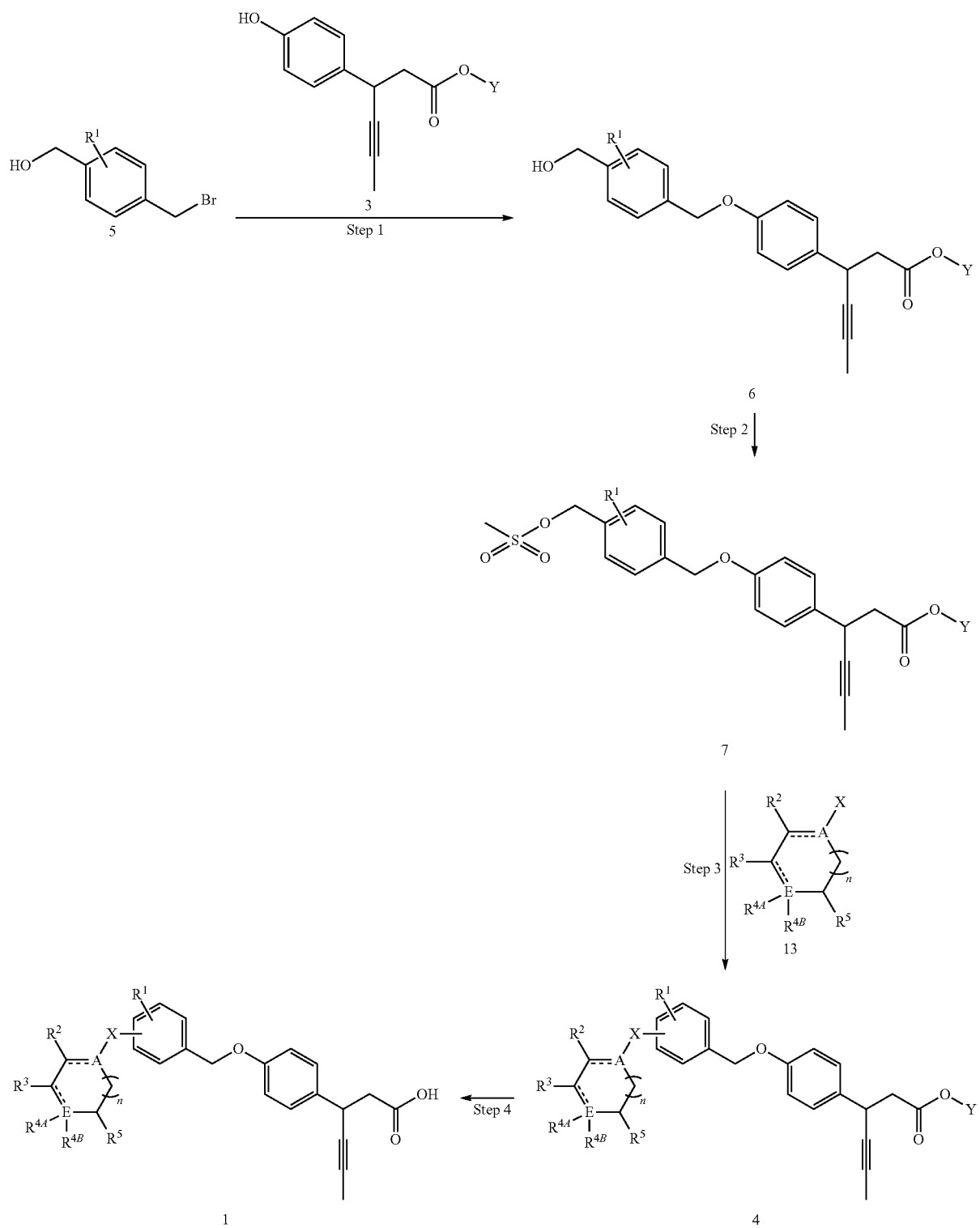

(In reaction formula 3, $R^1$, $R^2$, $R^3$, $R^{4A}$, $R^{4B}$, $R^5$, A, E, n, ⚌, and X are as defined in formula 1; and Y is $C_{1-10}$ straight or branched alkyl).

The present invention also provides a method for preparing the compound represented by formula 1 containing the step of preparing the compound represented by formula 1b by ring-opening reaction of the compound represented by formula 1a (step 1) as shown in the below reaction formula 4.

[Reaction Formula 4]

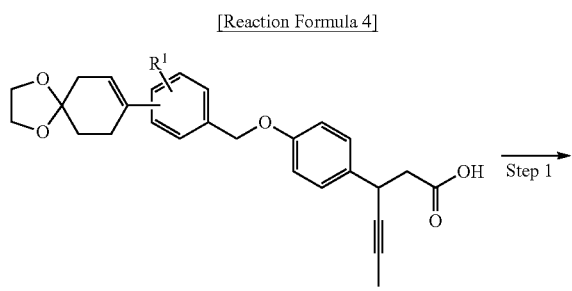

(In reaction formula 4, R¹ is as defined in formula 1; and the compounds represented by formula 1a and formula 1b are included in the compound represented by formula 1).

The present invention also provides a method for preparing the compound represented by formula 1 containing the step of preparing the compound represented by formula 1c by reduction reaction of the compound represented by formula 1b (step 1) as shown in the below reaction formula 5.

[Reaction Formula 5]

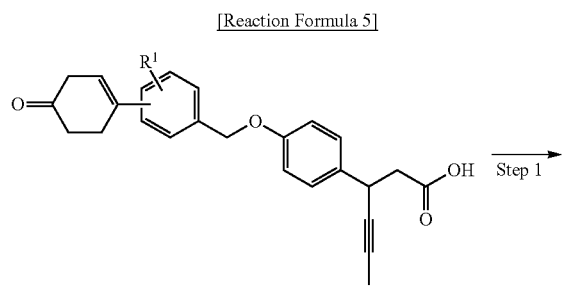
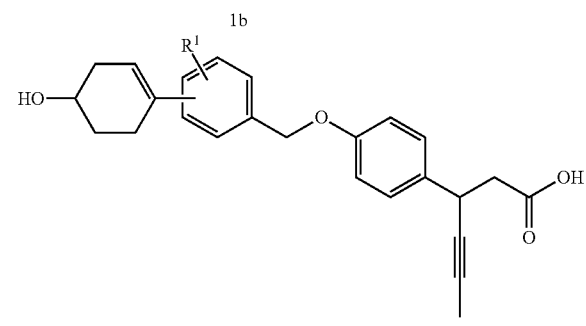

(In reaction formula 5, R¹ is as defined in formula 1; and the compounds represented by formula 1b and formula 1c are included in the compound represented by formula 1).

In addition, the present invention provides a pharmaceutical composition comprising the compound represented by formula 1, the optical isomer thereof, or the pharmaceutically acceptable salt thereof as an active ingredient.

Advantageous Effect

The novel 3-(4-(benzyloxy)phenyl)hex-4-inoic acid derivative, the optical isomer thereof, or the pharmaceutically acceptable salt thereof of the present invention has excellent activities of activating GPR40 protein and promoting insulin secretion accordingly but has no toxicity when co-administered with other drugs. That is, the novel 3-(4-(benzyloxy)phenyl)hex-4-inoic acid derivative, the optical isomer thereof, or the pharmaceutically acceptable salt thereof of the present invention can be co-administered with other drugs and can promote the activation of GPR40 protein significantly, so that the composition comprising the same as an active ingredient can be efficiently used as a pharmaceutical composition for the prevention and treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

BRIEF DESCRIPTION OF THE DRAWINGS

The application of the preferred embodiments of the present invention is best understood with reference to the accompanying drawings, wherein:

FIG. 1 is a graph illustrating the activation pattern of GPR40 according to the concentration of the compounds of Example 9, Comparative Example 1, and Comparative Example 3.

FIG. 2 is a graph illustrating the blood GLP-1 content in SD rat (Sprague Dawley rat) according to the oral-administration of the compounds of Example 9 and Comparative Example 1.

DESCRIPTION OF THE PREFERRED EMBODIMENTS

Hereinafter, the present invention is described in detail.
The present invention provides the compound represented by the below formula 1, the optical isomer thereof, or the pharmaceutically acceptable salt of the same.

[Formula 1]

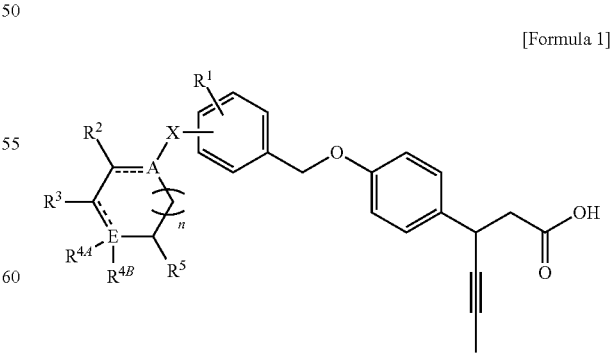

(In formula 1, ≡ is single bond or double bond;
A and E are independently C, N, or O;
n is an integer of 0-5;

X is single bond, or $C_{1-10}$ straight or branched alkylene;

$R^1$ is —H, —OH, halogen, $C_{1-10}$ straight or branched alkyl, $C_{1-10}$ straight or branched alkoxy, $C_{5-10}$ cycloalkyl, or $C_{5-10}$ cycloalkenyl;

$R^2$, $R^3$, and $R^5$ are independently —H, —OH, halogen, $C_{1-10}$ straight or branched alkyl, or $C_{1-10}$ straight or branched alkoxy;

Wherein, $R^2$ and $R^3$ can form $C_{5-10}$ cycloalkyl, $C_{6-10}$ aryl, 5-10 membered heterocycloalkyl or 5-10 membered heteroaryl along with atoms which are conjugated to the same. The 5-10 membered heterocycloalkyl can contain one or more hetero atoms selected from the group consisting of N, O, and S, and the 5-10 membered heteroaryl can contain one or more hetero atoms selected from the group consisting of N, O, and S;

$R^{4A}$ is —H, —OH, =O, unsubstituted or substituted $C_{6-10}$ aryl, or unsubstituted or substituted 5-10 membered heteroaryl containing one or more hetero atoms selected from the group consisting of N, O, and S, In the said substituted $C_{6-10}$ aryl and the substituted 5-10 membered heteroaryl, one or more substituents selected from the group consisting of —OH, halogen, nitrile, unsubstituted or substituted $C_{1-5}$ straight or branched alkyl in which one or more halogens are substituted, unsubstituted or substituted $C_{1-5}$ straight or branched alkoxy in which one or more halogens are substituted, $C_{1-10}$ straight or branched alkylsulfonyl,

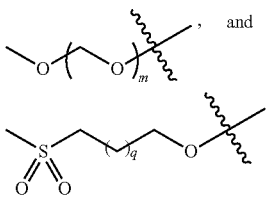, and can be substituted. Wherein, m and q are independently integers of 1-10, In the said unsubstituted or substituted 5-10 membered heteroaryl, phenyl can be fused;

Wherein, $R^3$ and $R^{4A}$ can form $C_{5-10}$ cycloalkyl, $C_{6-10}$ aryl, 5-10 membered heterocycloalkyl or 5-10 membered heteroaryl along with atoms which are conjugated to the same. The 5-10 membered heterocycloalkyl can contain one or more hetero atoms selected from the group consisting of N, O, and S, and the 5-10 membered heteroaryl can contain one or more hetero atoms selected from the group consisting of N, O, and S;

In the said $C_{5-10}$ cycloalkyl, $C_{6-10}$ aryl, 5-10 membered heterocycloalkyl, and 5-10 membered heteroaryl, $C_{1-5}$ straight or branched alkoxy can be substituted;

$R^{4B}$ is absent or can form 5-10 membered heterocycle containing one or more hetero atoms selected from the group consisting of N, O, and S along with atoms which are conjugated to the same and $R^{4A}$).

Preferably,

═══ is single bond or double bond;

A and E are independently C, N, or O;

n is an integer of 0-3;

X is single bond, or $C_{1-5}$ straight or branched alkylene;

$R^1$ is —H, —OH, halogen, $C_{1-5}$ straight or branched alkyl, $C_{1-5}$ straight or branched alkoxy, $C_{5-8}$ cycloalkyl, or $C_{5-8}$ cycloalkenyl;

$R^2$, $R^3$, and $R^5$ are independently —H, —OH, halogen, $C_{1-5}$ straight or branched alkyl, or $C_{1-5}$ straight or branched alkoxy;

Wherein, $R^2$ and $R^3$ can form $C_{5-8}$ cycloalkyl, $C_{6-8}$ aryl, 5-8 membered heterocycloalkyl or 5-8 membered heteroaryl along with atoms which are conjugated to the same. The 5-8 membered heterocycloalkyl can contain one or more hetero atoms selected from the group consisting of N, O, and S, and the 5-8 membered heteroaryl can contain one or more hetero atoms selected from the group consisting of N, O, and S;

$R^{4A}$ is —H, —OH, =O, unsubstituted or substituted $C_{6-8}$ aryl, or unsubstituted or substituted 5-8 membered heteroaryl containing one or more hetero atoms selected from the group consisting of N, O, and S, In the said substituted $C_{6-8}$ aryl and the substituted 5-8 membered heteroaryl, one or more substituents selected from the group consisting of —OH, halogen, nitrile, unsubstituted or substituted $C_{1-5}$ straight or branched alkyl in which one or more halogens are substituted, unsubstituted or substituted $C_{1-5}$ straight or branched alkoxy in which one or more halogens are substituted, $C_{1-8}$ straight or branched alkylsulfonyl,

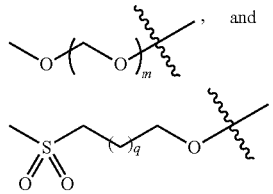, and can be substituted. Wherein, m and q are independently integers of 1-5, In the said unsubstituted or substituted 5-8 membered heteroaryl, phenyl can be fused;

Wherein, $R^3$ and $R^{4A}$ can form $C_{5-8}$ cycloalkyl, $C_{6-8}$ aryl, 5-8 membered heterocycloalkyl or 5-8 membered heteroaryl along with atoms which are conjugated to the same. The 5-8 membered heterocycloalkyl can contain one or more hetero atoms selected from the group consisting of N, O, and S, and the 5-8 membered heteroaryl can contain one or more hetero atoms selected from the group consisting of N, O, and S;

In the said $C_{5-8}$ cycloalkyl, $C_{6-8}$ aryl, 5-8 membered heterocycloalkyl, and 5-8 membered heteroaryl, $C_{1-5}$ straight or branched alkoxy can be substituted;

$R^{4B}$ is absent or can form 5-8 membered heterocycle containing one or more hetero atoms selected from the group consisting of N, O, and S along with atoms which are conjugated to the same and $R^{4A}$.

More preferably,

═══ is single bond or double bond;

A and E are independently C, or N;

n is an integer of 0-1;

X is single bond, or $C_{1-3}$ straight or branched alkylene;

$R^1$ is —H, or

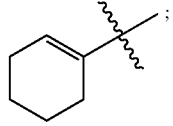 [SMILES: *C1=CCCCC1];

$R^2$, $R^3$, and $R^5$ are independently —H,

Wherein, $R^2$ and $R^3$ can form phenyl;

$R^{4A}$ is —H, —OH, =O,

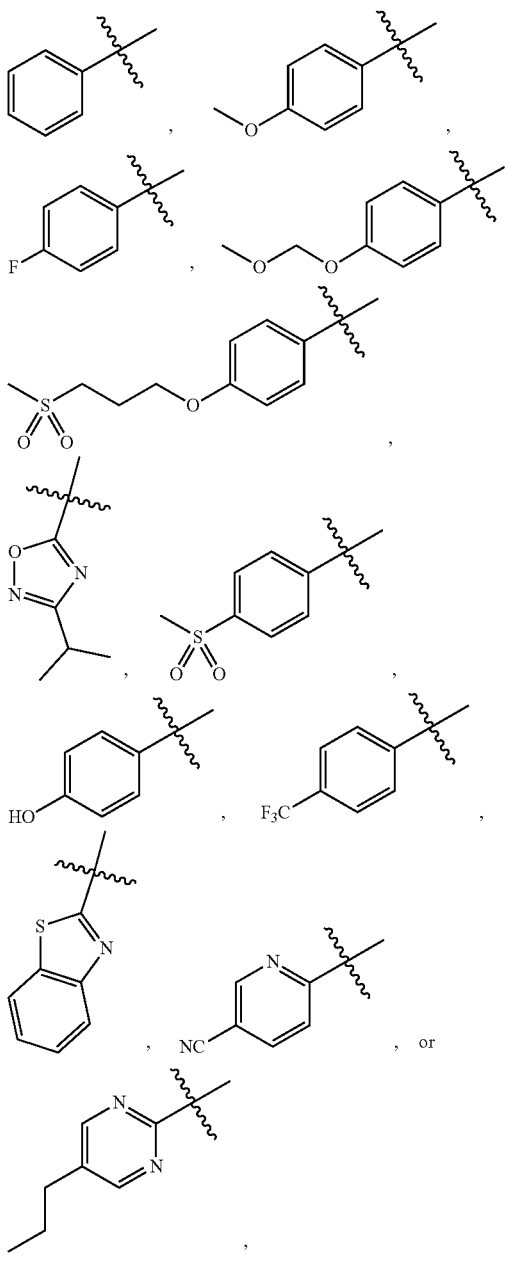

Wherein, $R^3$ and $R^{4A}$ can form phenyl along with atoms which are conjugated to the same. In the said phenyl, methoxy can be substituted;

$R^{4B}$ is absent or can form

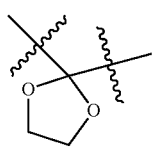 [SMILES: *C1(*)OCCO1]

along with atoms which are conjugated to the same and $R^{4A}$.

The compound represented by formula 1 can be exemplified by the following compounds.

(1) 3-(4-(3-(1,4-dioxaspiro[4,5]dec-7-en-8-yl)benzyloxy)phenyl)hex-4-ynoic acid;
(2) L-lysine 3-(4-(3-(1,4-dioxaspiro[4,5]dec-7-en-8-yl)benzyloxy)phenyl)hex-4-ynoate;
(3) 4-(4-(3-(1,4-dioxaspiro[4,5]dec-7-en-8-yl)benzyloxy)phenyl)hex-4-ynoic acid;
(4) 3-(4-(3-(4-oxocyclohex-1-enyl)benzyloxy)phenyl)hex-4-ynoic acid;
(5) 3-(4-(3-(4-hydroxycyclohex-1-enyl)benzyloxy)phenyl)hex-4-ynoic acid;
(6) L-lysine 3-(4-(3-(4-hydroxycyclohex-1-enyl)benzyloxy)phenyl)hex-4-ynoate;
(7) (3S)-3-(4-(3-(1,4-dioxaspiro[4,5]dec-7-en-8-yl)benzyloxy)phenyl)hex-4-ynoic acid;
(8) (3R)-3-(4-(3-(1,4-dioxaspiro[4,5]dec-7-en-8-yl)benzyloxy)phenyl)hex-4-ynoic acid;
(9) L-lysine (3S)-3-(4-(3-(1,4-dioxaspiro[4,5]dec-7-en-8-yl)benzyloxy)phenyl)hex-4-ynoate;
(10) L-lysine (3R)-3-(4-(3-(1,4-dioxaspiro[4,5]dec-7-en-8-yl)benzyloxy)phenyl)hex-4-ynoate L-lysinate;
(11) sodium (3S)-3-(4-(3-(1,4-dioxaspiro[4,5]dec-7-en-8-yl)benzyloxy)phenyl)hex-4-ynoate;
(12) 3-(4-(4-((3,4-dihydroisoquinoline-2(1H)-yl)methyl)benzyloxy) phenyl)hex-4-ynoic acid;
(13) 3-(4-(3-cyclohexenyl-4-((3,4-dihydroisoquinoline-2(1H)-yl)methyl)benzyloxy)phenyl)hex-4-ynoic acid;
(14) 3-(4-(4-((4-phenyl-5,6-dihydropyridine-1(2H)-yl)methyl) benzyloxy)phenyl)hex-4-ynoic acid;
(15) 3-(4-(4-((4-phenylpiperazine-1-yl)methyl)benzyloxy)phenyl)hex-4-ynoic acid;
(16) 3-(4-(4-((6-methoxy-3,4-dihydroisoquinoline-2(1H)-yl)methyl) benzyloxy)phenyl)hex-4-ynoic acid;
(17) 3-(4-(4-((4-phenylpiperidine-1-yl)methyl)benzyloxy)phenyl)hex-4-ynoic acid;
(18) 3-(4-(4-((4-(4-fluorophenyl)piperazine-1-yl)methyl)benzyloxy) phenyl)hex-4-ynoic acid;
(19) 3-(4-(4-((4-(4-(trifluoromethyl)phenyl)piperazine-1-yl)methyl) benzyloxy)phenyl)hex-4-ynoic acid;
(20) 3-(4-(4-((4-(4-(3-(methylsulfonyl)propoxy)phenyl)piperazine-1-yl)methyl)benzyloxy)phenyl)hex-4-ynoic acid;
(21) (S)-3-(4-(4-((3,4-dihydroisoquinoline-2(1H)-yl)methyl) benzyloxy)phenyl)hex-4-ynoic acid;
(22) (S)-3-(4-(4-((4-(4-(trifluoromethyl)phenyl)piperazine-1-yl)methyl)benzyloxy)phenyl)hex-4-ynoic acid;
(23) (S)-3-(4-(4-((4-(4-fluorophenyl)piperazine-1-yl)methyl)benzyloxy)phenyl)hex-4-ynoic acid;
(24) potassium (S)-3-(4-(4-((4-(4-(trifluoromethyl)phenyl)piperazine-1-yl)methyl)benzyloxy)phenyl)hex-4-ynoate;
(25) (5)-3-(4-(4-((6-methoxy-3,4-dihydroisoquinoline-2(1H)-yl)methyl)benzyloxy)phenyl)hex-4-ynoic acid;
(26) (S)-3-(4-(4-((4-phenylpiperidine-1-yl)methyl)benzyloxy)phenyl)hex-4-ynoic acid;
(27) (S)-3-(4-(4-(isoindoline-2-ylmethyl)benzyloxy)phenyl)hex-4-ynoic acid;
(28) (S)-3-(4-(4-((4-phenyl-5,6-dihydropyridine-1(2H)-yl)methyl)benzyloxy)phenyl)hex-4-ynoic acid;
(29) (S)-3-(4-(4-((4-(4-(methoxymethoxy)phenyl)piperazine-1-yl)methyl)benzyloxy)phenyl)hex-4-ynoic acid;
(30) (S)-3-(4-(4-((4-(5-isopropyl-1,2,4-oxadiazole-3-yl)piperidine-1-yl)methyl)benzyloxy)phenyl)hex-4-ynoic acid;
(31) (S)-3-(4-(4-((4-(5-isopropyl-1,2,4-oxadiazole-3-yl)piperazine-1-yl)methyl)benzyloxy)phenyl)hex-4-ynoic acid;
(32) (S)-3-(4-(4-((4-(4-(methylsulfonyl)phenyl)-5,6-dihydropyridine-1(2H)-yl)methyl)benzyloxy)phenyl)hex-4-ynoic acid;

(33) (S)-3-(4-(4-((4-(4-(3-(methylsulfonyl)propoxy)phenyl)-5,6-dihydropyridine-1(2H)-yl)methyl)benzyloxy)phenyl)hex-4-ynoic acid;
(34) (3S)-3-(4-(4-(1-(3,4-dihydroisoquinoline-2(1H)-yl)ethyl)benzyloxy)phenyl)hex-4-ynoic acid;
(35) (S)-3-(4-(4-((4-(4-hydroxyphenyl)piperazine-1-yl)methyl)benzyloxy)phenyl)hex-4-ynoic acid;
(36) (S)-3-(4-(4-((4-(4-(3-(methylsulfonyl)propoxy)phenyl)piperazine-1-yl)methyl)benzyloxy)phenyl)hex-4-ynoic acid;
(37) sodium (S)-3-(4-(4-(isoindoline-2-ylmethyl)benzyloxy)phenyl)hex-4-ynoate;
(38) L-lysine (S)-3-(4-(4-(isoindoline-2-ylmethyl)benzyloxy)phenyl)hex-4-ynoate;
(39) (S)-3-(4-(4-((4-(4-fluorophenyl)-5,6-dihydropyridine-1(2H)-yl)methyl)benzyloxy)phenyl)hex-4-ynoic acid;
(40) (S)-3-(4-(4-((4-(4-methoxyphenyl)piperazine-1-yl)methyl)benzyloxy)phenyl)hex-4-ynoic acid;
(41) sodium (S)-3-(4-(4-((3,4-dihydroquinoline-1(2H)-yl)methyl)benzyloxy)phenyl)hex-4-ynoate;
(42) potassium (S)-3-(4-(4-((3,4-dihydroquinoline-1(2H)-yl)methyl)benzyloxy)phenyl)hex-4-ynoate;
(43) (S)-3-(4-(4-((4-(benzo[d]thiazole-2-yl)piperazine-1-yl)methyl)benzyloxy)phenyl)hex-4-ynoic acid;
(44) (S)-3-(4-(4-((4-(5-propylpyrimidine-2-yl)piperazine-1-yl)methyl)benzyloxy)phenyl)hex-4-ynoic acid;
(45) (S)-3-(4-(4-((4-(5-cyanopyridine-2-yl)piperazine-1-yl)methyl)benzyloxy)phenyl)hex-4-ynoic acid;
(46) (3S)-3-(4-(4-((3-phenylpyrrolidine-1-yl)methyl)benzyloxy)phenyl)hex-4-ynoic acid;
(47) sodium (S)-3-(4-(4-((4-(4-methoxyphenyl)piperazine-1-yl)methyl)benzyloxy)phenyl)hex-4-ynoate;
(48) (S)-3-(4-(4-(2-(6-methoxy-3,4-dihydroisoquinoline-2(1H)-yl)ethyl)benzyloxy)phenyl)hex-4-ynoic acid;
(49) (S)-3-(4-(4-(2-(isoindoline-2-yl)ethyl)benzyloxy)phenyl)hex-4-ynoic acid;
(50) (S)-3-(4-(4-(2-(3,4-dihydroisoquinoline-2(1H)-yl)ethyl)benzyloxy)phenyl)hex-4-ynoic acid; and
(51) sodium (S)-3-(4-(4-((6-methoxy-3,4-dihydroisoquinoline-2(1H)-yl)methyl)benzyloxy)phenyl)hex-4-ynoate.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydriodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt in this invention can be prepared by the conventional method known to those in the art. For example, the compound represented by formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

A pharmaceutically acceptable salt can also be prepared by using the amino acid wherein amino group is attached on organic acid, and at this time the amino acid salt is preferably prepared as such natural amino acids as glysine, alanine, phenylalanine, valine, lysine, and glutamic acid, and is more preferably L-lysine.

The present invention includes not only the compound represented by formula 1 but also a pharmaceutically acceptable salt thereof, and a solvate, an optical isomer, or a hydrate possibly produced from the same.

In addition, the present invention provides a method for preparing the compound represented by formula 1.

Preparation Method 1

The compound represented by formula 1 of the present invention can be prepared by the method comprising the following steps, as shown in the below reaction formula 1:

preparing the compound represented by formula 4 by condensation reaction of the compound represented by formula 2 and the compound represented by formula 3 (step 1); and preparing the compound represented by formula 1 by reduction reaction of the compound represented by formula 4 prepared in step 1) (step 2).

[Reaction Formula 1]

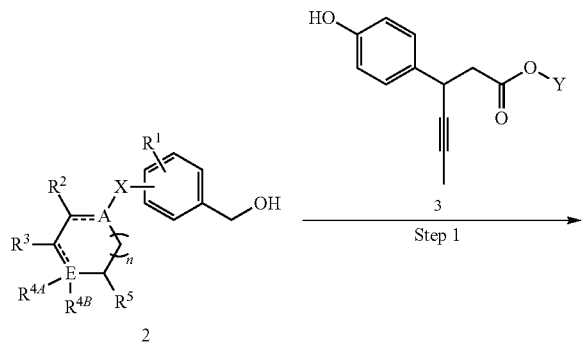

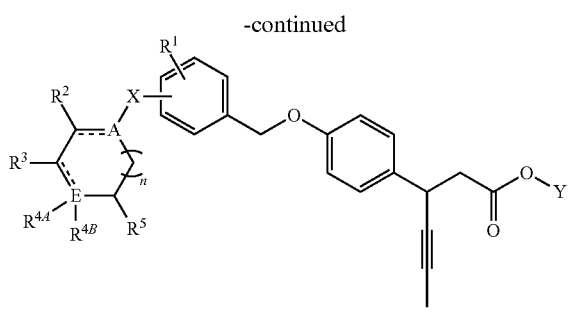

4

Step 2 ↓

1

(In reaction formula 1, $R^1$, $R^2$, $R^3$, $R^{4A}$, $R^{4B}$, $R^5$, A, E, n, ---, and X are as defined in formula 1; and Y is $C_{1-10}$ straight or branched alkyl).

Hereinafter, the method for preparing the compound represented by formula 1 of the present invention is illustrated in more detail, step by step.

In the method for preparing the compound represented by formula 1 of the present invention, step 1) is to prepare the compound represented by formula 4 by inducing the coupling reaction between the compound represented by formula 2 and the compound represented by formula 3. More precisely, the compound represented by formula 2, the compound represented by formula 3, and triphenylphosphine are all mixed, resulting in the mixed solution. Azocarboxylate reagent is slowly added to the mixed solution at the temperature of −5° C.~10° C., followed by inducing Mitsunobu reaction to give the compound represented by formula 4.

At this time, the azodicarboxylate reagent can be selected from the group consisting of diethyl azodicarboxylate (DEAD) and diisopropyl azodicarboxylate (DIAD), and diisopropyl azodicarboxylate (DIAD) is preferably selected.

The reaction solvent herein can be selected from the group consisting of tetrahydrofuran (THF), dichloromethane (DCM), toluene, and acetonitrile, and tetrahydrofuran is preferably selected.

The reaction temperature is preferably 0° C.~the boiling point of the solvent, and the reaction time is not limited, but 0.5~10 hour reaction is preferred.

In the method for preparing the compound represented by formula 1 of the present invention, step 2) is to prepare the compound represented by formula 1 by inducing the reduction reaction of the compound represented by formula 4 prepared in step 1) in the presence of a base. More precisely, the compound represented by formula 4 prepared in step 1) is reacted with a base at room temperature, by which the ester group included in the compound represented by formula 4 is reduced into carboxyl group, resulting in the preparation of the compound represented by formula 1.

At this time, the base can be selected from the group consisting of potassium hydroxide (KOH), sodium hydroxide (NaOH), and lithium hydroxide (LiOH), and potassium hydroxide (KOH) is preferably selected.

The reaction solvent herein can be selected from the group consisting of tetrahydrofuran (THF), dichloromethane (DCM), toluene, and acetonitrile, and tetrahydrofuran is preferably selected.

The reaction temperature is preferably 0° C.~the boiling point of the solvent, and the reaction time is not limited, but 0.5~10 hour reaction is preferred.

Preparation of the Starting Material (the Compound Represented by Formula 2)

In the reaction formula 1 of the present invention, the compound represented by formula 2 can be prepared by the method comprising the following steps, as shown in the below reaction formula 2:

preparing the compound represented by formula 10 by reacting the compound represented by formula 8 and the compound represented by formula 9 (step 1);

preparing the compound represented by formula 12 by reacting the compound represented by formula 10 prepared in step 1) and the compound represented by formula 11 (step 2); and preparing the compound represented by formula 2 by reduction reaction of the compound represented by formula 12 prepared in step 2) (step 3).

[Reaction Formula 2]

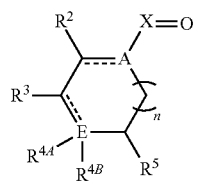

8

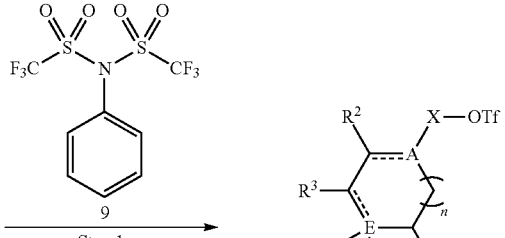

Step 1

10

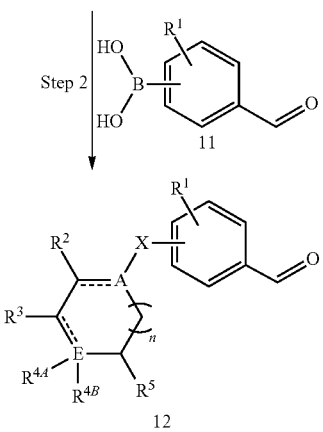

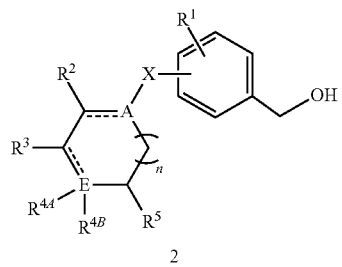

(In reaction formula 2, $R^1$, $R^2$, $R^3$, $R^{4A}$, $R^{4B}$, $R^5$, A, E, n, ===, and X are as defined in formula 1; and -OTf is trifluoromethanesulfonate).

Hereinafter, the method for preparing the compound represented by formula 2 of the present invention is illustrated in more detail, step by step.

In the method for preparing the compound represented by formula 2 of the present invention, step 1) is to prepare the compound represented by formula 10 by reacting the compound represented by formula 8 and the compound represented by formula 9. More precisely, the compound represented by formula 8 and the compound represented by formula 9 were dissolved in an organic solvent at −80° C.~−70° C., to which bis(trimethylsilyl)amide metal complex is slowly added, followed by stirring with raising temperature to give the compound represented by formula 10.

At this time, the bis(trimethylsilyl)amide metal complex can be selected from the group consisting of potassium bis(trimethylsilyl)amide, lithium bis(trimethylsilyl)amide, and sodium bis(trimethylsilyl)amide, and potassium bis(trimethylsilyl)amide is preferably selected.

The organic solvent herein can be selected from the group consisting of tetrahydrofuran (THF), diethylether, diphenylether, diisopropylether (DIPE), dimethylformamide (DMF), dimethylacetamide (DMA), dimethylsulfoxide DMSO), dichloromethane (DCM), chlorobenzene, toluene, and benzene.

The reaction temperature is preferably −80° C.~the boiling point of the solvent, and the reaction time is not limited, but 0.5~10 hour reaction is preferred.

In the method for preparing the compound represented by formula 2 of the present invention, step 2) is to prepare the compound represented by formula 12 by reacting the compound represented by formula 10 prepared in step 1) and the compound represented by formula 11. More precisely, the compound represented by formula 12 is prepared by inducing Suzuki coupling reaction between the compound represented by formula 10 prepared in step 1) and the boronate compound represented by formula 11.

At this time, the palladium catalyst can be tetrakis(triphenylphosphine) (Pd(PPh$_3$)$_4$), bis(triphenylphosphine)palladium(II) dichloride (PdCl$_2$(PPh$_3$)$_2$), palladium dichloride (PdCl$_2$), or palladium acetate (Pd(OCOCH$_3$)$_2$), and tetrakis(triphenylphosphine) (Pd(PPh$_3$)$_4$) is more preferred.

The organic solvent herein is selected from the group consisting of tetrahydrofuran (THF), diethylether, diphenylether, diisopropylether (DIPE), dimethylformamide (DMF), dimethylacetamide (DMA), dimethylsulfoxide (DMSO), dichloromethane (DCM), chlorobenzene, toluene, and benzene, and toluene is preferably selected.

The reaction temperature is preferably 0° C.~the boiling point of the solvent, and the reaction time is not limited, but 0.5~10 hour reaction is preferred.

In the method for preparing the compound represented by formula 2 of the present invention, step 3) is to prepare the compound represented by formula 2 by inducing reduction reaction of the compound represented by formula 12 prepared in step 2) in the presence of a base. More precisely, the compound represented by formula 12 prepared in step 2) is dissolved in an organic solvent, to which a base is added. Then, aldehyde group included in the compound represented by formula 12 is reduced into hydroxy group, resulting in the compound represented by formula 2.

At this time, the organic solvent can be methanol, ethanol, ethylacetate, tetrahydrofuran, diethyl ether, or a mixed solution comprising two or more of those solvents, but preferably tetrahydrofuran:methanol (4:1) mixed solvent is used herein.

The base herein can be sodium borohydride (NaBH$_3$) or lithium aluminum hydride (LiAlH$_4$), and sodium borohydride (NaBH$_3$) is more preferred.

The reaction temperature is preferably 0° C.~the boiling point of the solvent, and the reaction time is not limited, but 0.5~10 hour reaction is preferred.

Preparation Method 2

The compound represented by formula 1 of the present invention can be prepared by the method comprising the following steps, as shown in the below reaction formula 3:

preparing the compound represented by formula 6 by inducing coupling reaction between the compound represented by formula 5 and the compound represented by formula 3 (step 1);

preparing the compound represented by formula 7 by inducing Mesylate reaction of the compound represented by formula 6 prepared in step 1) (step 2);

preparing the compound represented by formula 4 by replacing the Mesylate site of the compound represented by formula 7 with the compound represented by formula 13 (step 3); and preparing the compound represented by formula 1 by inducing reduction reaction of the compound represented by formula 4 prepared in step 3) (step 4).

[Reaction Formula 3]

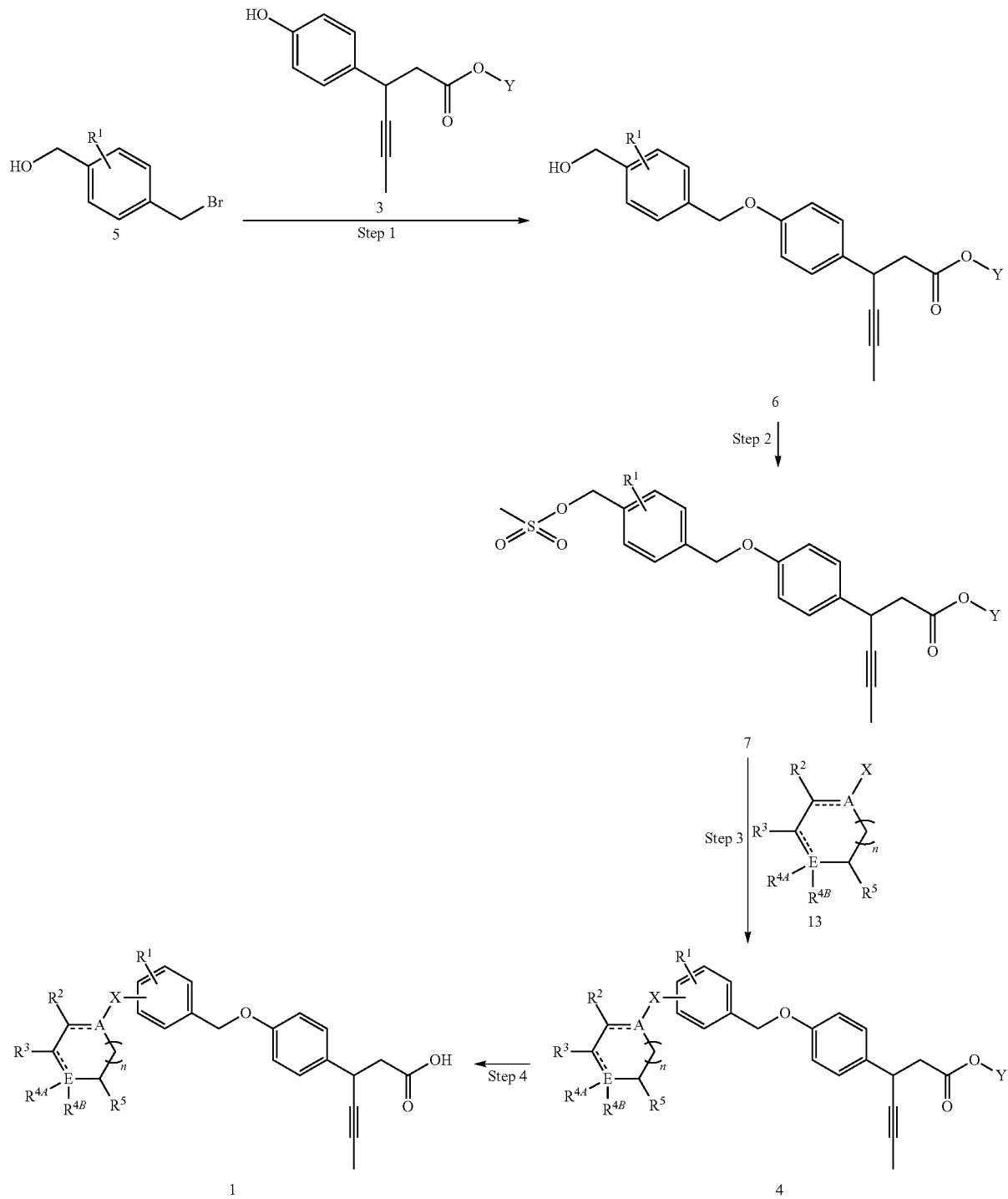

(In reaction formula 3, $R^1$, $R^2$, $R^3$, $R^{4A}$, $R^{4B}$, $R^5$, A, E, n, ⁼⁼⁼, and X are as defined in formula 1; and Y is $C_{1-10}$ straight or branched alkyl).

Hereinafter, the method for preparing the compound represented by formula 1 of the present invention is illustrated in more detail, step by step.

In the method for preparing the compound represented by formula 1 of the present invention, step 1) is to prepare the compound represented by formula 6 by inducing coupling reaction between the compound represented by formula 5 and the compound represented by formula 3.

The organic solvent herein is selected from the group consisting of tetrahydrofuran (THF), diethylether, diphenylether, diisopropylether (DIPE), dimethylformamide (DMF), dimethylacetamide (DMA), dimethylsulfoxide (DMSO), dichloromethane (DCM), chlorobenzene, toluene, and benzene, and dimethylformamide (DMF) is preferably selected.

The base herein can be cesium carbonate ($Cs_2CO_3$), sodium borohydride ($NaBH_3$) or lithium aluminum hydride ($LiAlH_4$), and cesium carbonate ($Cs_2CO_3$) is more preferred.

The reaction temperature is preferably 0° C.~the boiling point of the solvent, and the reaction time is not limited, but 0.5~10 hour reaction is preferred.

In the method for preparing the compound represented by formula 1 of the present invention, step 2) is to prepare the compound represented by formula 7 by inducing Mesylate reaction of the compound represented by formula 6 prepared in step 1) in a solvent.

At this time, the sample used for the Mesylate reaction can be methane sulfonyl chloride (MsCl).

The organic solvent herein is selected from the group consisting of triethylamine (TEA), tetrahydrofuran (THF), diethylether, diphenylether, diisopropylether (DIPE), dimethylformamide (DMF), dimethylacetamide (DMA), dimethylsulfoxide (DMSO), dichloromethane (DCM), chlorobenzene, toluene, and benzene, and triethylamine (TEA) is preferably selected.

The reaction temperature is preferably 0° C.~the boiling point of the solvent, and the reaction time is not limited, but 0.5~10 hour reaction is preferred.

In the method for preparing the compound represented by formula 1 of the present invention, step 3) is to prepare the compound represented by formula 4 by replacing the Mesylate site of the compound represented by formula 7 prepared in step 2) with the compound represented by formula 13.

At this time, the organic solvent herein is selected from the group consisting of tetrahydrofuran (THF), diethylether, diphenylether, diisopropylether (DIPE), dimethylformamide (DMF), dimethylacetamide (DMA), dimethylsulfoxide (DMSO), dichloromethane (DCM), chlorobenzene, toluene, and benzene, and dichloromethane (DCM) is preferably selected.

The base herein can be cesium carbonate ($Cs_2CO_3$), sodium borohydride ($NaBH_3$) or lithium aluminum hydride ($LiAlH_4$), and cesium carbonate ($Cs_2CO_3$) is more preferred.

The reaction temperature is preferably 0° C.~the boiling point of the solvent, and the reaction time is not limited, but 0.5~10 hour reaction is preferred.

In the method for preparing the compound represented by formula 1 of the present invention, step 4) is to prepare the compound represented by formula 1 by inducing reduction reaction of the compound represented by formula 4 prepared in step 3) in the presence of a base. More precisely, the compound represented by formula 4 prepared in step 3) is reacted with a base at room temperature to reduce the ester group included in the compound represented by formula 4 into carboxyl group, resulting in the preparation of the compound represented by formula 1.

At this time, the base herein can be potassium hydroxide (KOH), sodium hydroxide (NaOH), or lithium hydroxide (LiOH), and potassium hydroxide (KOH) is more preferred.

The reaction solvent herein can be tetrahydrofuran (THF), dichloromethane (DCM), toluene, or acetonitrile, and tetrahydrofuran (THF) is more preferred.

The reaction temperature is preferably 0° C.~the boiling point of the solvent, and the reaction time is not limited, but 0.5~10 hour reaction is preferred.

Preparation Method 3

The compound represented by formula 1 of the present invention can be prepared by the method containing the step of preparing the compound represented by formula 1b by ring-opening reaction of the compound represented by formula 1a (step 1), as shown in the below reaction formula 4.

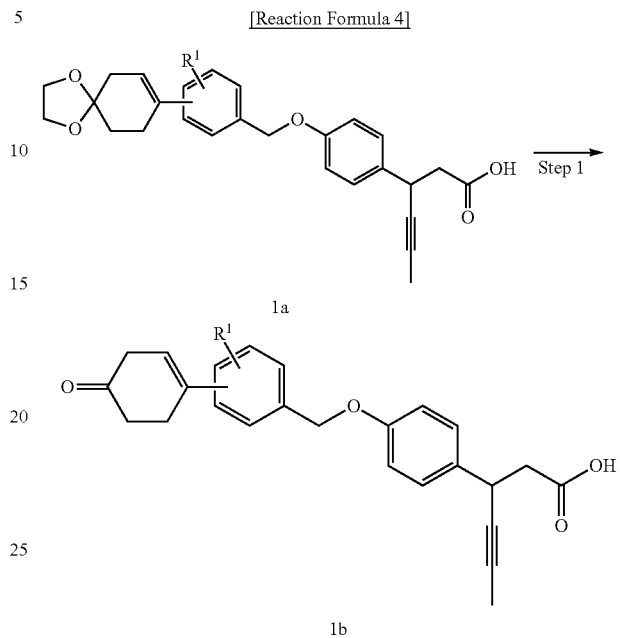

[Reaction Formula 4]

(In reaction formula 4, $R^1$ is as defined in formula 1; and the compounds represented by formula 1a and formula 1b are included in the compound represented by formula 1).

Hereinafter, the preparation method of the present invention is described in more detail, step by step.

In the preparation method, step 1) is to prepare the compound represented by formula 1b by inducing ring-opening reaction of the compound represented by formula 1a in the presence of an acid. More precisely, the compound represented by formula 1a included in the compound represented by formula 1 proceeded to ring-opening reaction in the presence of an acid. As a result, the heterocycle of the compound represented by formula 1a is opened to give the compound represented by formula 1b containing carbonyl.

At this time, the acid herein can be hydrochloric acid, sulfuric acid, or phosphoric acid, and hydrochloric acid is more preferred.

The reaction solvent herein can be tetrahydrofuran (THF), dichloromethane (DCM), toluene, or acetonitrile, and tetrahydrofuran (THF) is more preferred.

The reaction temperature is preferably 0° C.~the boiling point of the solvent, and the reaction time is not limited, but 0.5~10 hour reaction is preferred.

Preparation Method 4

The compound represented by formula 1 of the present invention can be prepared by the method containing the step of preparing the compound represented by formula 1c by reduction reaction of the compound represented by formula 1b (step 1), as shown in the below reaction formula 5.

[Reaction Formula 5]

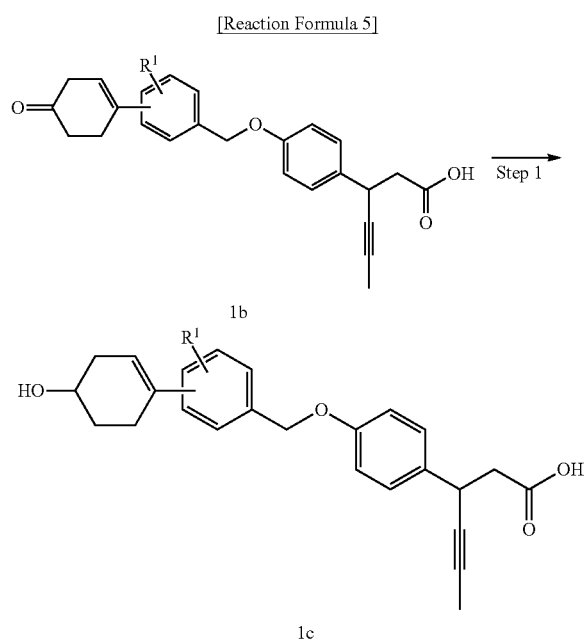

(In reaction formula 5, R$^1$ is as defined in formula 1; and the compounds represented by formula 1b and formula 1c are included in the compound represented by formula 1).

Hereinafter, the preparation method of the present invention is described in more detail, step by step.

In the preparation method, step 1) is to prepare the compound represented by formula 1c by inducing reduction reaction of the compound represented by formula 1b in the presence of a base. More precisely, the compound represented by formula 1b, one of the compound represented by formula 1 is reduced in the presence of a base. That is, carbonyl group of the compound represented by formula 1b is reduced into hydroxy group, resulting in the compound represented by formula 1c.

At this time, the base herein can be sodium borohydride (NaBH$_3$) or lithium aluminum hydride (LiAlH$_4$), and sodium borohydride (NaBH$_3$) is more preferred.

The reaction solvent herein can be tetrahydrofuran (THF), dichloromethane (DCM), toluene, or acetonitrile, and tetrahydrofuran (THF) is more preferred.

The reaction temperature is preferably 0° C.~the boiling point of the solvent, and the reaction time is not limited, but 0.5~10 hour reaction is preferred.

The present invention also provides a pharmaceutical composition comprising the compound represented by formula 1, the optical isomer thereof, or the pharmaceutically acceptable salt thereof as an active ingredient for the prevention or treatment of metabolic disease.

At this time, the pharmaceutical composition is characteristically functioning to activate GPR40 enzyme.

GPR40 is the G-protein coupled receptor (GPCR) mainly expressed in insulin secreting cells in the pancreas. The GPR40 expression profile has the potential usability for the treatment of various metabolic diseases including obesity and diabetes.

Therefore, the inventors investigated the activation pattern of GPR40 receptor according to the compound represented by formula 1, the optical isomer thereof, or the pharmaceutically acceptable salt thereof of the present invention. As a result, all the experimental compounds of the present invention could activate GPR40 receptor by 50% (EC$_{50}$) at a low concentration, suggesting that the activating effect of the compounds of the present invention was excellent (see Experimental Examples 1 and 2, and FIG. 1).

In relation to the drug metabolism of the compound represented by formula 1, the optical isomer thereof, or the pharmaceutically acceptable salt thereof of the present invention, the inventors evaluated the CYP enzyme inhibiting rate of the same. As a result, all the experimental compounds were confirmed not to cause toxicity when co-administered with other drugs regardless of the concentration, suggesting that they can be co-administered with other drugs when complications have to be treated (see Experimental Example 3).

The present inventors also performed oral glucose tolerance test with the compound represented by formula 1, the optical isomer thereof, or the pharmaceutically acceptable salt thereof of the invention. As a result, all the experimental compounds of the invention demonstrated similar or more excellent blood glucose lowering effect than the conventional GPR40 activator, suggesting that they were all excellent in activating GPR40 in vivo (see Experimental Examples 4, 5, and 6).

The present inventors also investigated the blood GLP-1 increasing rate according to the oral administration of the compound represented by formula 1, the optical isomer thereof, or the pharmaceutically acceptable salt thereof of the invention. As a result, the compound of Comparative Example 1 did not display blood GLP-1 increasing effect after the administration, compared with the glucose treated group (Veh.), while the compound of Example 9 of the present invention increased blood GLP-1 after being administered to SD rat (see Experimental Example 7, and FIG. 2).

Therefore, the compound represented by formula 1 of the present invention is not only excellent in activating GPR40 protein and in promoting insulin secretion thereby but also co-usable with other drugs, so that the composition comprising the compound of formula 1 that is excellent in activating GPR40 protein in vivo as an active ingredient can be efficiently used as a pharmaceutical composition for the prevention or treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

The compound represented by formula 1 of the present invention can be administered orally or parenterally and be used in general forms of pharmaceutical formulation. That is, the compound of the present invention can be prepared for oral or parenteral administration by mixing with generally used diluents or excipients such as fillers, extenders, binders, wetting agents, disintegrating agents and surfactants.

Solid formulations for oral administration are tablets, pills, powders, granules, capsules, and troches, etc. These solid formulations are prepared by mixing the compound of the invention with one or more suitable excipients such as starch, calcium carbonate, sucrose or lactose, and gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The effective dosage of the compound of the present invention can be adjusted according to the age, weight, and gender of patient, administration pathway, health condition, severity of disease, etc. In general, the dosage is 0.001~100 mg/kg/day, and preferably 0.01~35 mg/kg/day. The compound of the present invention can be administered by 0.07~7000 mg/day for an adult patient that weighs 70 kg, and more preferably by 0.7~2500 mg/day, which can be administered 1~several times a day at a regular interval according to the judgment of a doctor or a pharmacist.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Manufacturing Example 1: Preparation of ethyl 3-(4-hydroxyphenyl)hex-4-inoate

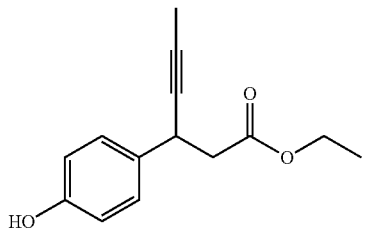 [SMILES: CC#CC(CC(=O)OCC)c1ccc(O)cc1]

3-(4-hydroxyphenyl)-hex-4-inoic acid (20.0 g) and ethanol (200 mL) were loaded in a 250 mL flask in nitrogen atmosphere, followed by stirring for dissolving them. Sulfuric acid (9.6 mL) was slowly added thereto at room temperature. The mixture was reflux-stirred for at least 6 hours. Upon completion of the reaction, distilled water (150 mL) was slowly added thereto, followed by extraction using ethylacetate (200 mL). The extracted organic layer was dried under reduced pressure to give the target compound (19.5 g, 85.7%).

$^1$H NMR (400 MHz, CDCl$_3$): δ 7.25 (2H, d), 6.78 (2H, d), 4.95 (1H, s), 4.14 (2H, m), 4.04 (1H, m), 2.68 (2H, m), 1.84 (3H, d), 1.29 (3H, t).

Manufacturing Example 2: Preparation of (S)-ethyl 3-(4-hydroxyphenyl)hex-4-inoate

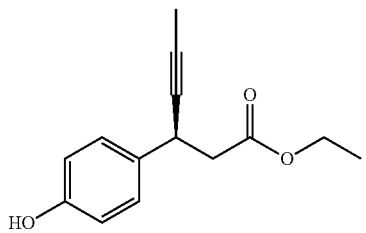 [SMILES: CC#C[C@@H](CC(=O)OCC)c1ccc(O)cc1]

(S)-3-(4-hydroxyphenyl)-hex-4-inoic acid (20.0 g) and ethanol (200 mL) were loaded in a 250 mL flask in nitrogen atmosphere, followed by stirring for dissolving them. Sulfuric acid (9.6 mL) was slowly added thereto at room temperature. The mixture was reflux-stirred for at least 6 hours. Upon completion of the reaction, distilled water (150 mL) was slowly added thereto, followed by extraction using ethylacetate (200 mL). The extracted organic layer was dried under reduced pressure to give the target compound (21.2 g, 93.2%).

$^1$H NMR (400 MHz, CDCl$_3$): δ 7.25 (2H, d), 6.78 (2H, d), 4.95 (1H, s), 4.14 (2H, m), 4.04 (1H, m), 2.68 (2H, m), 1.84 (3H, d), 1.29 (3H, t).

Manufacturing Example 3: Preparation of (R)-ethyl 3-(4-hydroxyphenyl)hex-4-inoate

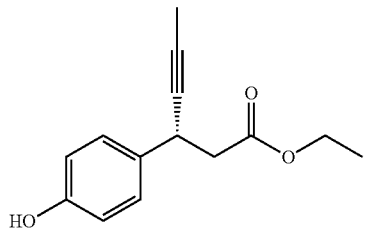 [SMILES: CC#C[C@H](CC(=O)OCC)c1ccc(O)cc1]

(R)-3-(4-hydroxyphenyl)-hex-4-inoic acid (20.0 g) and ethanol (200 mL) were loaded in a 250 mL flask in nitrogen atmosphere, followed by stirring for dissolving them. Sulfuric acid (9.6 mL) was slowly added thereto at room temperature. The mixture was reflux-stirred for at least 6 hours. Upon completion of the reaction, distilled water (150 mL) was slowly added thereto, followed by extraction using ethylacetate (200 mL). The extracted organic layer was dried under reduced pressure to give the target compound (20.6 g, 90.6%).

$^1$H NMR (400 MHz, CDCl$_3$): δ 7.25 (2H, d), 6.78 (2H, d), 4.95 (1H, s), 4.14 (2H, m), 4.04 (1H, m), 2.68 (2H, m), 1.84 (3H, d), 1.29 (3H, t).

Manufacturing Example 4: Preparation of (3-(1,4-dioxaspiro[4,5]des-7-en-8-yl)phenyl)methanol

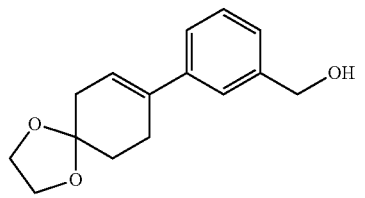 [SMILES: OCc1cccc(C2=CCC3(CC2)OCCO3)c1]

Step 1: Preparation of 1,4-dioxaspiro[4,5]des-7-en-8-yl trifluoromethanesulfonate 1.4-dioxaspiro[4.5]decane-8-one (30.0 g) and toluene (300 mL) were loaded in a 1000 mL flask in nitrogen atmosphere, followed by stifling for dissolving them. Then, N-phenyl bis(trifluoromethanesulfoneimide) (64.3 g) was added thereto. 0.7 M potassium bis(trimethylsilyl)amide solution (257 mL) was slowly added thereto by using a dropping funnel at −78° C., followed by stifling for at least 4 hours with raising the temperature to room temperature. Upon completion of the reaction, distilled water (200 mL) was slowly added thereto, followed by extraction using ethylacetate (300 mL). The extracted organic layer was dried under reduced pressure to give the target compound (54.7 g, 98.8%).

$^1$H NMR (400 MHz, CDCl$_3$): δ 5.68 (1H, t), 4.01 (4H, s), 2.55 (2H, t), 2.42 (2H, d), 1.92 (2H, t).

Step 2: Preparation of 3-(1,4-dioxaspiro[4,5]des-7-en-8-yl)benzaldehyde 1.4-dioxaspiro[4.5]des-7-en-8-yl trifluoromethanesulfonate (54.70 g) and toluene (300 mL) were loaded in a 1000 mL flask in nitrogen atmosphere, followed by stirring for dissolving them. 3-formylphenylboronic acid (28.7 g) and cesiumcarbonate (156 g) were added thereto. The mixture was cooled down to 0° C., to which tetrakis(triphenylphosphine)palladium (11.09 g) was slowly added. The mixture was stirred for at least 3 hours with raising the temperature to room temperature. Upon completion of the reaction, distilled water (200 mL) was slowly added thereto, followed by extraction using ethylacetate (300 mL). The extracted organic layer was dried under reduced pressure to give the target compound (45.9 g, 99%).

$^1$H NMR (400 MHz, CDCl$_3$): δ 10.03 (1H, s), 7.92 (1H, s), 7.76 (1H, d), 7.67 (1H, d), 7.47 (1H, t), 6.11 (1H, s), 4.05 (4H, s), 2.71 (2H, t), 2.51 (2H, s), 1.97 (2H, t).

Step 3: Preparation of (3-(1,4-dioxaspiro[4,5]des-7-en-8-yl)phenyl)methanol 3-(1.4-dioxaspiro[4.5]des-7-en-8-yl)benzaldehyde (46.9 g), tetrahydrofuran (160 mL) and methanol (40 mL) were loaded in a 500 mL flask in nitrogen atmosphere, followed by stifling for dissolving them. The mixture was cooled down to 0° C. Then, sodiumborohydride (10.9 g) was slowly added thereto, followed by stifling for at least 3 hours with raising the temperature to room temperature. Upon completion of the reaction, distilled water (150 mL) was slowly added thereto, followed by extraction using ethylacetate (150 mL). The extracted organic layer was dried under reduced pressure to give the target compound (37.8 g, 81.7%).

$^1$H NMR (400 MHz, CDCl$_3$): δ 7.34 (1H, s), 7.25 (3H, m), 6.01 (1H, m), 4.69 (2H, d), 4.04 (4H, s), 2.68 (2H, m), 2.48 (2H, s), 1.94 (2H, t), 1.80 (1H, t).

Manufacturing Example 5: Preparation of (4-(1,4-dioxaspiro[4,5]des-7-en-8-yl)phenyl)methanol

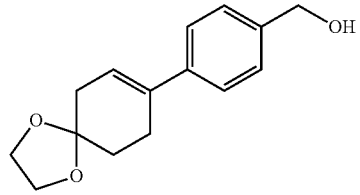 [SMILES: OCc1ccc(C2=CCC3(CC2)OCCO3)cc1]

Step 1: Preparation of 4-(1,4-dioxaspiro[4,5]des-7-en-8-yl)benzaldehyde 1.4-dioxaspiro[4.5]des-7-en-8-yl trifluoromethanesulfonate (3.0 g) and toluene (50 mL) were loaded in a 250 mL flask in nitrogen atmosphere, followed by stifling for dissolving them. 3-formylphenyl boronic acid (1.8 g) and cesiumcarbonate (8.47 g) were added thereto. The mixture was cooled down to 0° C., to which tetrakis(triphenylphosphine)palladium (601 mg) was slowly added. The mixture was stirred for at least 3 hours with raising the temperature to room temperature. Upon completion of the reaction, distilled water (500 mL) was slowly added thereto, followed by extraction using ethylacetate (100 mL). The extracted organic layer was dried under reduced pressure to give the target compound (2.0 g, 78.7%).

$^1$H NMR (400 MHz, CDCl$_3$): δ 10.00 (1H, s), 7.84 (2H, d), 7.57 (2H, d), 6.19 (1H, s), 4.06 (4H, s), 2.71 (2H, t), 2.53 (2H, s), 1.97 (2H, t).

Step 2: Preparation of (4-(1,4-dioxaspiro[4,5]des-7-en-8-yl)phenyl)methanol 4-(1,4-dioxaspiro[4,5]des-7-en-8-yl)benzaldehyde (2.0 g), tetrahydrofuran (40 mL), and methanol (10 mL) were loaded in a 250 mL flask in nitrogen atmosphere, followed by stifling for dissolving them. The mixture was cooled down to 0° C. Then, sodiumborohydride (619 mg) was slowly added thereto, followed by stirring for at least 3 hours with raising the temperature to room temperature. Upon completion of the reaction, distilled water (50 mL) was slowly added thereto, followed by extraction using ethylacetate (100 mL). The extracted organic layer was dried under reduced pressure to give the target compound (1.6 g, 52.9%).

$^1$H NMR (400 MHz, CDCl$_3$): δ 7.40 (2H, d), 7.32 (2H, d), 6.01 (1H, m), 4.70 (2H, d), 4.13 (4H, s), 2.68 (2H, t), 2.49 (2H, s), 1.93 (2H, t), 1.60 (1H, t).

Manufacturing Example 6: Preparation of ethyl 3-(4-(4-((methylsulfonyloxy)methyl)benzyloxy)phenyl)hex-4-inoate Step 1: Preparation of (4-(bromomethyl)phenyl)methanol

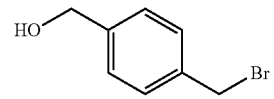

Methyl 4-(bromomethyl)benzoate (5.0 g) and MC (20 ml) were loaded in a 1 L flask in nitrogen atmosphere, followed by stirring for dissolving them. Then, 70 ml of DIBAL-H was slowly added thereto at −78° C., followed by stifling for 5 hours. Upon completion of the reaction, the mixture was cooled down to 0° C. and distilled water was slowly added thereto, followed by extraction using MC. The extracted organic layer was dried under reduced pressure to give the target compound.

$^1$H NMR (400 MHz, CDCl$_3$): δ 7.42 (2H, d), 7.38 (2H, d), 4.73 (2H, s), 4.52 (2H, m).

Step 2: Preparation of ethyl 3-(4-(4-(hydroxymethyl)benzyloxy)phenyl)hex-4-inoate

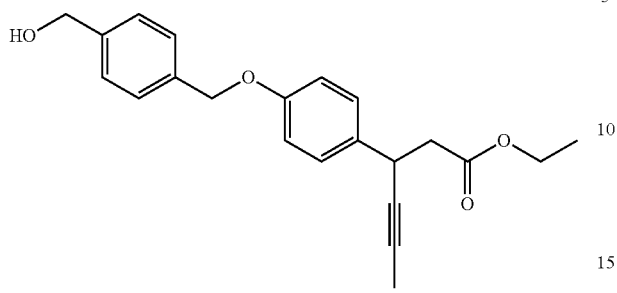

4.0 g of ethyl 3-(4-hydroxyphenyl)hex-4-inoate prepared in Manufacturing Example 1 and 5.0 g of (4-(bromomethyl)phenyl)methanol prepared in step 1) were loaded in a 500 mL flask containing 50 ml of DMF in nitrogen atmosphere, followed by stirring for dissolving them. Then, 9.0 g of Cs$_2$CO$_3$ was loaded thereto, followed by stirring at room temperature for 12 hours. Upon completion of the reaction, distilled water was slowly added thereto, followed by extraction using ethylacetate. The extract was washed with brine, dried over anhydrous MgSO$_4$, and concentrated. Then, silica gel column chromatography was performed to give the target compound.

$^1$H NMR (400 MHz, CDCl$_3$): δ 7.42 (2H, d), 7.38 (2H, d), 7.29 (2H, d), 6.93 (2H, d), 5.06 (2H, s), 4.73 (2H, d), 4.15 (2H, m), 4.06 (1H, m), 2.68 (2H, m), 1.84 (3H, s), 1.69 (1H, m), 1.24 (3H, m).

Step 3: Preparation of ethyl 3-(4-(4-((methylsulfonyloxy)methyl)benzyloxy)phenyl) hex-4-inoate

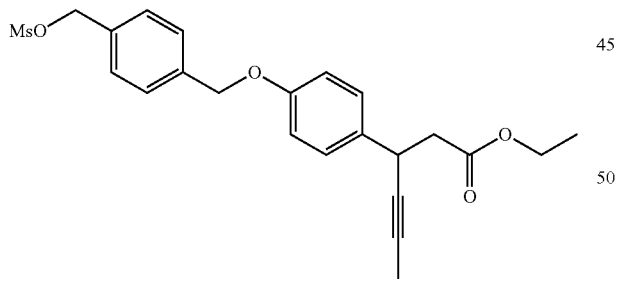

3.0 g of ethyl 3-(4-(4-(hydroxymethyl)benzyloxy)phenyl)hex-4-inoate obtained in step 2) was loaded in a 500 mL flask containing 30 ml of MC in nitrogen atmosphere, followed by stifling for dissolving them. Then, 4.0 mL of TEA was loaded thereto at 0° C. 30 minutes later, 2.1 ml of MsCl was slowly added thereto. One hour later when the reaction was completed, distilled water was slowly added thereto, followed by extraction using MC. The extracted organic layer was dried under reduced pressure to give the target compound.

$^1$H NMR (400 MHz, CDCl$_3$): δ 7.49 (4H, m), 7.29 (2H, d), 6.93 (2H, d), 5.27 (2H, s), 5.08 (2H, s), 4.15 (2H, m), 4.06 (1H, m), 2.95 (3H, s), 2.68 (2H, m), 1.84 (3H, s), 1.69 (1H, m), 1.24 (3H, m).

Manufacturing Example 7: Preparation of (S)-ethyl 3-(4-(4-((methylsulfonyloxy)methyl)benzyloxy)phenyl)hex-4-inoate

Step 1: Preparation of (S)-ethyl 3-(4-(4-(hydroxymethyl)benzyloxy)phenyl)hex-4-inoate

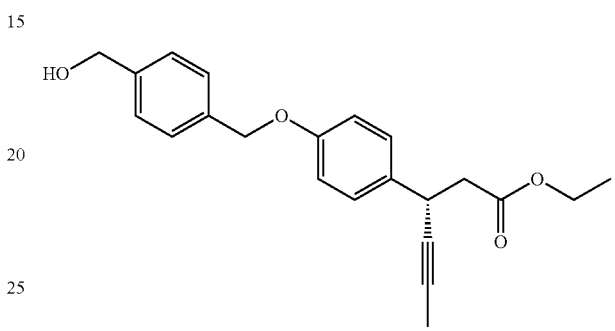

The target compound was obtained by the same manner as described in step 2) of Manufacturing Example 6 except that (S)-ethyl 3-(4-hydroxyphenyl)hex-4-inoate was used instead of ethyl 3-(4-hydroxyphenyl)hex-4-inoate.

$^1$H NMR (400 MHz, CDCl$_3$): δ 7.42 (2H, d), 7.38 (2H, d), 7.29 (2H, d), 6.93 (2H, d), 5.06 (2H, s), 4.73 (2H, d), 4.15 (2H, m), 4.06 (1H, m), 2.68 (2H, m), 1.84 (3H, s), 1.69 (1H, m), 1.24 (3H, m).

Step 2: Preparation of (S)-ethyl 3-(4-(4-((methylsulfonyloxy)methyl)benzyloxy)phenyl)hex-4-inoate

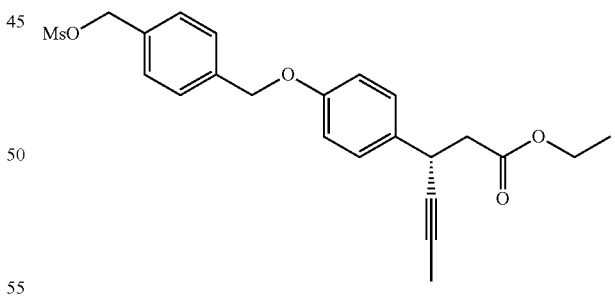

The target compound was obtained by the same manner as described in step 3) of Manufacturing Example 6 except that (S)-ethyl 3-(4-(4-(hydroxymethyl)benzyl)phenyl)hex-4-inoate obtained in step 1) was used instead of ethyl 3-(4-(4-(hydroxymethyl)benzyloxy)phenyl)hex-4-inoate.

$^1$H NMR (400 MHz, CDCl$_3$): δ 7.49 (4H, m), 7.29 (2H, d), 6.93 (2H, d), 5.27 (2H, s), 5.08 (2H, s), 4.15 (2H, m), 4.06 (1H, m), 2.95 (3H, s), 2.68 (2H, m), 1.84 (3H, s), 1.69 (1H, m), 1.24 (3H, m).

Manufacturing Example 8: Preparation of 6-methoxy-1,2,3,4-tetrahydroisoquinoline

Step 1: Preparation of ethyl 3-methoxyphenetylcarbamate

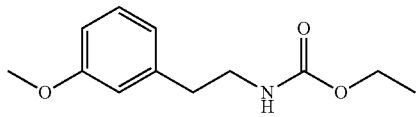 [SMILES: CCOC(=O)NCCc1cccc(OC)c1]

25 g of 2-(3-methoxyphenyl)ethaneamine was loaded in a flask containing 300 ml of MC in nitrogen atmosphere, followed by stifling for dissolving them. Then, 24.2 ml of TEA was loaded thereto at 0° C. 30 minutes later, 16.6 ml of ethyl chloroformate was slowly added thereto. One hour later when the reaction was completed, distilled water was slowly added thereto, followed by extraction using MC. The extracted organic layer was dried under reduced pressure to give the target compound.

$^1$H NMR (400 MHz, CDCl$_3$): δ 7.25 (1H, m), 6.79 (3H, m), 4.70 (1H, s), 4.13 (2H, m), 3.81 (3H, s), 3.46 (2H, m), 2.80 (2H, m), 1.25 (3H, m).

Step 2: Preparation of 6-methoxy-3,4-dihydroisoquinoline-1(2H)-one

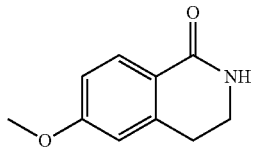

36 g of ethyl 3-methoxyphenetylcarbamate obtained in step 1) and 120 g of polyphosphoric acid were loaded in a 500 mL flask in nitrogen atmosphere, followed by stirring for dissolving them. Then, the mixture was refluxed with heating for at least 3 hours. The mixture was cooled down to room temperature. Ethylacetate and distilled water were slowly added thereto, followed by extraction at least three times. The extracted organic layer was washed with brine, dried over anhydrous MgSO$_4$, and concentrated. Then, silica gel column chromatography was performed to give the target compound.

$^1$H NMR (400 MHz, CDCl$_3$): δ 8.03 (1H, d), 6.87 (1H, d), 6.72 (1H, s), 6.44 (1H, s), 3.86 (3H, s), 3.57 (2H, m), 2.98 (2H, m).

Step 3: Preparation of 6-methoxy-1,2,3,4-tetrahydroisoquinoline

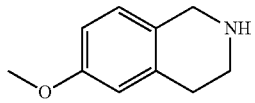

10 g of 6-methoxy-3,4-dihydroisoquinoline-1(2H)-one was loaded in a flask containing 150 ml of THF in nitrogen atmosphere, followed by stirring for dissolving them. Then, 4.3 g of LAH was slowly added thereto at 0° C. After inducing heat-reflux for at least 5 hours, when the reaction was completed, distilled water was slowly added, followed by extraction using ethylacetate. The extract was washed with brine, dried over anhydrous MgSO$_4$, and concentrated. Then, solidification was performed to give the target compound.

$^1$H NMR (400 MHz, CDCl$_3$): δ 6.94 (1H, d), 6.73 (1H, d), 6.65 (1H, s), 4.14 (2H, s), 3.80 (3H, s), 3.13 (2H, m), 2.79 (2H, m).

Manufacturing Example 9: Preparation of 4-(4-(methylsulfonyl)phenyl)-1,2,3,6-tetrahydropyridine hydrochloride

Step 1: Preparation of tert-butyl 4-(4-(methylsulfonyl)phenyl)-5,6-dihydropyridine-1(2H)-carboxylate

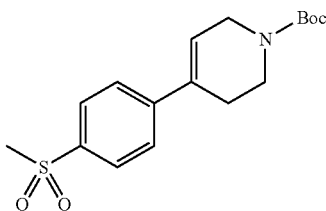 [SMILES: CC(C)(C)OC(=O)N1CC=C(c2ccc(S(C)(=O)=O)cc2)CC1]

3.31 g of tert-butyl 4-(trifluoromethylsulfonyloxy)-5,6-dihydropyridine-1(2H)-carboxylate and 50 ml of toluene were loaded in a 1000 mL flask in nitrogen atmosphere, followed by stifling for dissolving them. then, 2.0 g of 4-(methylsulfonyl)phenylboronic acid and 6.6 g of cesium-carbonate were added thereto. The mixture was cooled down to 0° C., to which 1.16 g of tetrakis(triphenylphosphine) palladium (11.09 g) was slowly added. The mixture was stirred for at least 3 hours with raising the temperature to room temperature. Upon completion of the reaction, distilled water was slowly added thereto, followed by extraction using ethylacetate. The extracted organic layer was dried under reduced pressure. Then, silica gel column chromatography was performed to give the target compound.

$^1$H NMR (400 MHz, CDCl$_3$): δ 7.92 (2H, d), 7.56 (2H, d), 6.21 (1H, s), 4.14 (2H, d), 3.68 (2H, m), 3.07 (3H, s), 2.56 (2H, s), 1.49 (9H, s).

Step 2: Preparation of 4-(4-(methylsulfonyl)phenyl)-1,2,3,6-tetrahydropyridine hydrochloride

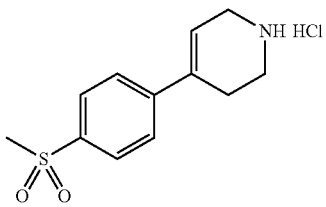 [SMILES: CS(=O)(=O)c1ccc(C2=CCNCC2)cc1 ; Cl]

1.4 g of tert-butyl 4-(4-(methylsulfonyl)phenyl)-5,6-dihydropyridine-1(2H)-carboxylate obtained in step 1) was dissolved in 20 ml of MC, to which 10.4 ml of 4 N HCl was added. 5 hours later, when the reaction was completed, diethyl ether was added thereto. Then, solidification was performed to give the target compound.

¹H NMR (400 MHz, D₂O): δ 7.92 (2H. d), 7.56 (2H, d), 6.21 (1H, s), 4.14 (2H, d), 3.68 (2H, m), 3.07 (3H, s), 2.56 (2H, s).

Manufacturing Example 10: Preparation of 4-(1,2,3,6-tetrahydropyridine-4-yl)phenol hydrochloride Step 1: Preparation of tert-butyl 4-(4-hydroxyphenyl)-5,6-dihydropyridine-1(2H)-carboxylate

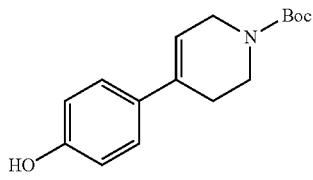 [SMILES: CC(C)(C)OC(=O)N1CC=C(c2ccc(O)cc2)CC1]

The target compound was obtained by the same manner as described in step 1) of Manufacturing Example 9 except that 4-hydroxyphenylboronic acid was used instead of 4-(methylsulfonyl)phenylboronic acid.

¹H NMR (400 MHz, CDCl₃): δ 7.26 (2H, d), 6.83 (2H, d), 5.93 (1H, s), 5.47 (1H, s), 4.07 (2H, s), 3.66 (2H, m), 2.50 (2H, s), 1.52 (9H, s).

Step 2: Preparation of 4-(1,2,3,6-tetrahydropyridine-4-yl)phenol hydrochloride

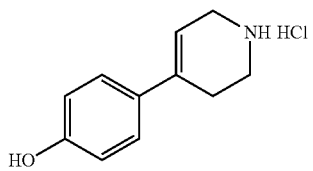

The target compound was obtained by the same manner as described in step 2) of Manufacturing Example 9 except that tert-butyl 4-(4-hydroxyphenyl)-5,6-dihydropyridine-1(2H)-carboxylate obtained in step 1) was used instead of tert-butyl 4-(4-(methylsulfonyl)phenyl)-5,6-dihydropyridine-1(2H)-carboxylate.

¹H NMR (400 MHz, D₂O): δ 7.26 (2H, d), 6.83 (2H, d), 5.93 (1H, s), 5.47 (1H, s), 4.07 (2H, s), 3.66 (2H, m), 2.50 (2H, s).

Manufacturing Example 11: Preparation of 4-(4-(3-(methylsulfonyl)propoxy)phenyl)-1,2,3,6-tetrahydropyridine hydrochloride Step 1: Preparation of 3-(methylthio)propyl 4-methylbenzenesulfonate

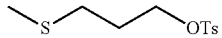

25.4 g of 3-(methylthio)propane-1-ol was loaded in a 500 mL flask containing 500 ml of MC in nitrogen atmosphere, followed by stirring for dissolving them. Then, 44 ml of TEA was added thereto at 0° C. 30 minutes later, 46 g of TsCl was slowly added thereto. One hour later, when the reaction was completed, distilled water was slowly added thereto, followed by extraction using MC. The extracted organic layer was dried under reduced pressure to give the target compound.

¹H NMR (400 MHz, CDCl₃): δ 7.81 (2H, d), 7.38 (2H, d), 4.16 (2H, m), 2.53 (2H, m), 2.47 (3H, s), 2.05 (3H, s), 1.94 (2H, m).

Step 2: Preparation of 3-(methylsulfonyl)propyl 4-methylbenzenesulfonate

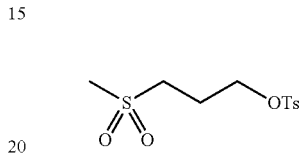

62 g of 3-(methylthio)propyl 4-methylbenzenesulfonate obtained in step 1) was loaded in THF/distilled water (150/100 ml) in a flask in nitrogen atmosphere, followed by stirring for dissolving them. Then, 310 g of oxone was added thereto. The mixture was stirred for 12 hours at room temperature. Upon completion of the reaction, distilled water was slowly added thereto, followed by extraction using ethylacetate. The extract was washed with brine, dried over anhydrous MgSO₄, and concentrated to give the target compound.

¹H NMR (400 MHz, CDCl₃): δ 7.81 (2H, d), 7.38 (2H, d), 4.20 (2H, m), 3.13 (2H, m), 2.93 (3H, s), 2.48 (3H, s), 2.23 (2H, m).

Step 3: Preparation of tert-butyl 4-(4-(3-(methylsulfonyl)propoxy)phenyl)-5,6-dihydropyridine-1(2H)-carboxylate

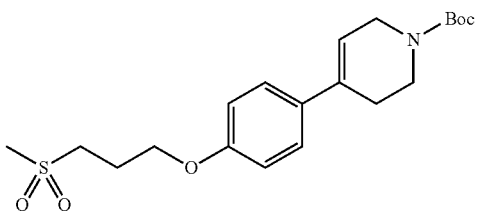 [SMILES: CC(C)(C)OC(=O)N1CC=C(c2ccc(OCCCS(C)(=O)=O)cc2)CC1]

The target compound was obtained by the same manner as described in step 2) of Manufacturing Example 6 except that tert-butyl 4-(4-hydroxyphenyl)-5,6-dihydropyridine-1(2H)-carboxylate obtained in step 1) of Manufacturing Example 10 and 3-(methylsulfonyl)propyl 4-methylbenzenesulfonate obtained in step 2) of Manufacturing Example 10 were used.

¹H NMR (400 MHz, CDCl₃): δ 7.34 (2H, d), 6.85 (2H, d), 6.00 (1H, s), 4.12 (2H, s), 3.28 (2H, m), 3.18 (2H, s), 2.97 (3H, s), 2.72 (2H, m), 2.56 (2H, m), 2.36 (2H, m), 1.52 (9H, s).

Step 4: Preparation of 4-(4-(3-(methylsulfonyl)propoxy)phenyl)-1,2,3,6-tetrahydropyridine hydrochloride

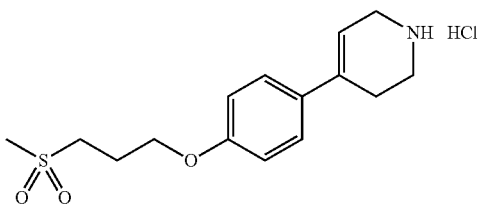 [SMILES: CS(=O)(=O)CCCOc1ccc(C2=CCNCC2)cc1 ; Cl]

The target compound was obtained by the same manner as described in step 2) of Manufacturing Example 9 except that tert-butyl 4-(4-(3-(methylsulfonyl)propoxy)phenyl)-5,6-dihydropyridine-1(2H)-carboxylate obtained in step 3) was used instead of tert-butyl 4-(4-(methylsulfonyl)phenyl)-5,6-dihydropyridine-1(2H)-carboxylate.

¹H NMR (400 MHz, D₂O): δ 7.34 (2H, d), 6.85 (2H, d), 6.00 (1H, s), 4.12 (2H, s), 3.28 (2H, m), 3.18 (2H, s), 2.97 (3H, s), 2.72 (2H, m), 2.56 (2H, m), 2.36 (2H, m).

Manufacturing Example 12: Preparation of (3S)-ethyl 3-(4-(4-(1-bromoethyl)benzyloxy)phenyl)hex-4-inoate Step 1: Preparation of 1-(4-(bromomethyl)phenyl)ethanone

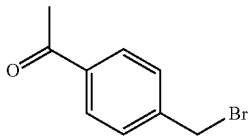

5.0 g of 1-p-tolylethane was dissolved in 100 ml of CCl₄ in a flask in nitrogen atmosphere with stirring, to which 14.6 g of NBS and 6.7 g of AIBN were added at 0° C. Then, the mixture was refluxed with heating for at least 5 hours. Upon completion of the reaction, distilled water was slowly added thereto, followed by extraction using MC. The extracted organic layer was washed with brine, dried over anhydrous MgSO₄, and concentrated. Then, silica gel column chromatography was performed to give the target compound.

¹H NMR (400 MHz, CDCl₃): δ 7.95 (2H, d), 7.50 (2H, d), 4.52 (2H, s), 2.62 (3H, s).

Step 2: Preparation of (S)-ethyl 3-(4-(4-acetylbenzyloxy)phenyl)hex-4-inoate

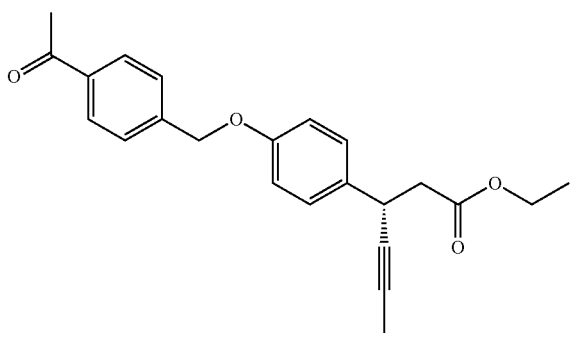 [SMILES: CC#C[C@@H](CC(=O)OCC)c1ccc(OCc2ccc(C(C)=O)cc2)cc1]

The target compound was obtained by the same manner as described in step 2) of Manufacturing Example 6 except that (S)-ethyl 3-(4-hydroxyphenyl)hex-4-inoate obtained in Manufacturing Example 2 and 1-(4-(bromomethyl)phenyl)ethanone obtained in step 1) were used.

¹H NMR (400 MHz, CDCl₃): δ 7.99 (2H, d), 7.53 (2H, d) 7.31 (2H, d), 6.92 (2H, d), 5.13 (2H, s), 4.15 (2H, m), 4.09 (1H, m), 2.75 (2H, m), 2.64 (3H, s), 1.84 (3H, d), 1.24 (3H, m).

Step 3: Preparation of (3S)-ethyl 3-(4-(4-(1-hydroxyethyl)benzyloxy)phenyl)hex-4-inoate

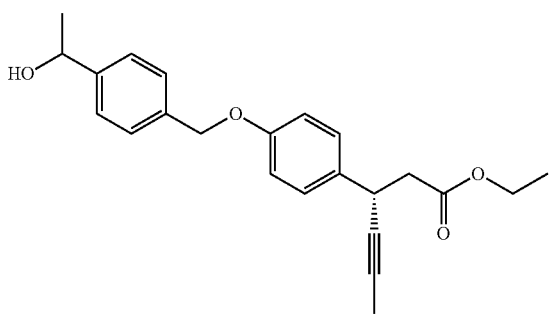 [SMILES: CC#C[C@@H](CC(=O)OCC)c1ccc(OCc2ccc(C(C)O)cc2)cc1]

1.0 g of (S)-ethyl 3-(4-(4-acetylbenzyloxy)phenyl)hex-4-inoate obtained in step 2) was dissolved in 50 ml of THF in a flask with stirring in nitrogen atmosphere, to which 0.16 g of NaBH₄ was added at 0° C. After stifling the mixture at room temperature for at least 2 hours, when the reaction was completed, distilled water was slowly added thereto, followed by extraction using EA. The extracted organic layer was washed with brine, dried over anhydrous MgSO₄, and concentrated to give the target compound.

¹H NMR (400 MHz, CDCl₃): δ 8.02 (2H, d), 7.57 (2H, d) 7.36 (2H, d), 6.99 (2H, d), 5.21 (2H, s), 4.23 (2H, m), 4.17 (1H, m), 3.81 (1H, s), 2.75 (2H, m), 2.64 (3H, s), 1.84 (3H, d), 1.24 (3H, m).

Step 4: Preparation of (3S)-ethyl 3-(4-(4-(1-bromoethyl)benzyloxy)phenyl)hex-4-inoate

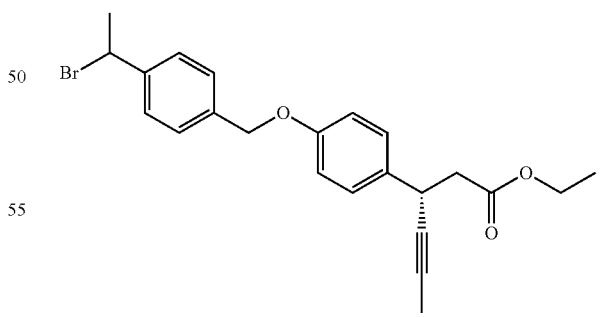

0.76 g of (3S)-ethyl 3-(4-(4-(1-hydroxyethyl)benzyloxy)phenyl)hex-4-inoate obtained in step 3) was dissolved in 50 ml of MC in a flask with stifling in nitrogen atmosphere, to which 0.6 g of triphenylphosphine and 0.75 g of CBr₄ were added at 0° C. After stifling the mixture at room temperature for at least 2 hours, when the reaction was completed, distilled water was slowly added thereto, followed by extraction using EA. The extracted organic layer was washed with brine, dried over anhydrous MgSO$_4$, and concentrated to give the target compound.

$^1$H NMR (400 MHz, CDCl$_3$): δ 8.02 (2H, d), 7.57 (2H, d) 7.36 (2H, d), 6.99 (2H, d), 5.21 (2H, s), 4.23 (2H, m), 4.17 (1H, m), 3.92 (1H, s), 2.85 (2H, m), 2.44 (3H, s), 1.86 (3H, d), 1.27 (3H, m).

Manufacturing Example 13: Preparation of 2-(piperazine-1-yl)benzo[d]thiazole hydrochloride Step 1: Preparation of tert-butyl 4-(benzo[d]thiazole-2-yl)piperazine-1-carboxylate

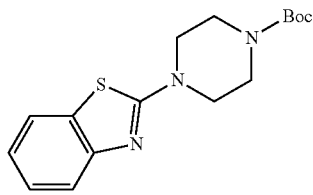 [SMILES: CC(C)(C)OC(=O)N1CCN(c2nc3ccccc3s2)CC1]

2.0 g of tert-butyl piperazine-1-carboxylate was dissolved in AN/distilled water (100/50 ml) in a flask with stirring in nitrogen atmosphere, to which 2.1 ml of DIPEA was added at 0° C. 0.9 g of 2-chlorobenzo[d]thiazole was added thereto, followed by heat-reflux for at least 2 hours. Upon completion of the reaction, distilled water was slowly added thereto, followed by extraction using EA. The extracted organic layer was washed with brine, dried over anhydrous MgSO$_4$, and concentrated to give the target compound.

$^1$H NMR (400 MHz, CDCl$_3$): δ 7.61 (1H, d), 7.60 (1H, d), 7.29 (1H, m), 7.09 (1H, m), 3.77 (4H, m), 2.62 (4H, m), 1.52 (9H, s).

Step 2: Preparation of 2-(piperazine-1-yl)benzo[d]thiazole hydrochloride

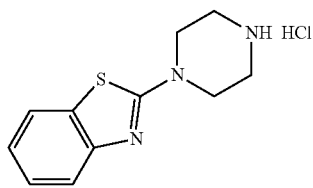 [SMILES: c1ccc2sc(N3CCNCC3)nc2c1 ; Cl]

The target compound was obtained by the same manner as described in step 2) of Manufacturing Example 9 except that tert-butyl 4-(benzo[d]thiazole-2-yl)piperazine-1-carboxylate obtained in step 1) was used instead of tert-butyl 4-(4-(methylsulfonyl)phenyl)-5,6-dihydropyridine-1(2H)-carboxylate.

$^1$H NMR (400 MHz, D$_2$O): δ 7.61 (1H, d), 7.60 (1H, d), 7.29 (1H, m), 7.09 (1H, m), 3.77 (4H, m), 2.62 (4H, m).

Manufacturing Example 14: Preparation of 2-(piperazine-1-yl)-5-propylpyrimidine hydrochloride Step 1: Preparation of tert-butyl 4-(5-propylpyrimidine-2-yl)piperazine-1-carboxylate

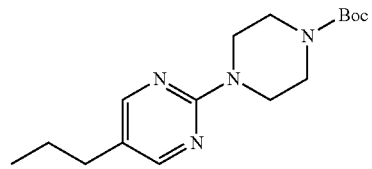 [SMILES: CCCc1cnc(N2CCN(C(=O)OC(C)(C)C)CC2)nc1]

The target compound was obtained by the same manner as described in step 1) of Manufacturing Example 13 except that 2-chloro-5-propylpyrimidine was used instead of 2-chlorobenzo[d]thiazole.

$^1$H NMR (400 MHz, CDCl$_3$): δ 8.19 (2H, s), 3.77 (4H, m), 2.62 (4H, m), 2.41 (2H, m), 1.61 (2H, m), 1.52 (9H, s), 0.96 (3H, m).

Step 2: Preparation of 2-(piperazine-1-yl)-5-propylpyrimidine hydrochloride

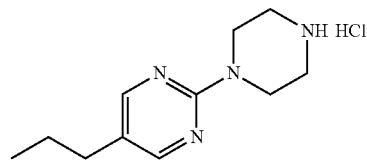

The target compound was obtained by the same manner as described in step 2) of Manufacturing Example 9 except that tert-butyl 4-(5-propylpyrimidine-2-yl)piperazine-1-carboxylate obtained in step 1) was used instead of tert-butyl 4-(4-(methylsulfonyl)phenyl)-5,6-dihydropyridine-1(2H)-carboxylate.

$^1$H NMR (400 MHz, D$_2$O): δ 8.19 (2H, s), 3.77 (4H, m), 2.62 (4H, m), 2.41 (2H, m), 1.61 (2H, m), 0.96 (3H, m).

Manufacturing Example 15: Preparation of 6-(piperazine-1-yl)nicotinonitrile hydrochloride Step 1: Preparation of tert-butyl 4-(5-cyanopyridine-2-yl)piperazine-1-carboxylate

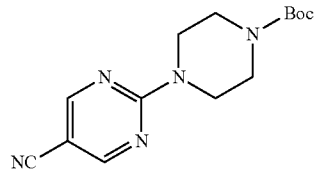 [SMILES: CC(C)(C)OC(=O)N1CCN(c2ncc(C#N)cn2)CC1]

The target compound was obtained by the same manner as described in step 1) of Manufacturing Example 13 except that 6-chloronicotinonitrile was used instead of 2-chlorobenzo[d]thiazole.

¹H NMR (400 MHz, CDCl₃): δ 8.41 (1H, s) 7.61 (1H, d), 6.59 (1H, d), 3.77 (4H, m), 2.62 (4H, m), 1.52 (9H, s).

Step 2: Preparation of 6-(piperazine-1-yl)nicotinonitrile hydrochloride

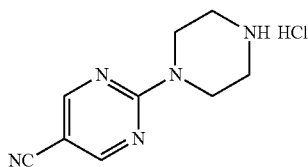 [SMILES: N#Cc1cnc(N2CCNCC2)nc1 ; Cl]

The target compound was obtained by the same manner as described in step 2) of Manufacturing Example 9 except that tert-butyl 4-(5-cyanopyridine-2-yl)piperazine-1-carboxylate obtained in step 1) was used instead of tert-butyl 4-(4-(methylsulfonyl)phenyl)-5,6-dihydropyridine-1(2H)-carboxylate.

¹H NMR (400 MHz, D₂O): δ 8.41 (1H, s) 7.61 (1H, d), 6.59 (1H, d), 3.77 (4H, m), 2.62 (4H, m).

Manufacturing Example 16: Preparation of (S)-ethyl 3-(4-(4-(2-(methylsulfonyloxy)ethyl)benzyloxy)phenyl)hex-4-inoate Step 1: Preparation of 2-(4-(bromomethyl)phenyl)ethanol

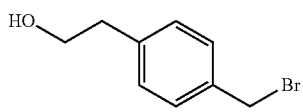

5 g of 2-(4-(bromomethyl)phenyl)acetic acid was dissolved in 100 ml of THF in a flask with stifling in nitrogen atmosphere, to which 70 ml of borane-THF solution was slowly added at 0° C. After stifling the mixture for 2 hours, when the reaction was completed, the temperature was lowered to 0° C. and distilled water was slowly added thereto, followed by extraction using EA. The extracted organic layer was dried under reduced pressure to give the target compound.

¹H NMR (400 MHz, CDCl₃): δ 37 (2H, d), 7.24 (2H, d), 4.51 (2H, s), 3.89 (2H, m), 2.89 (2H, m).

Step 2: Preparation of (S)-ethyl 3-(4-(4-(2-hydroxyethyl)benzyloxy)phenyl)hex-4-inoate

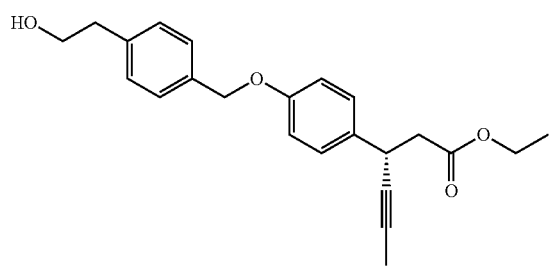 [SMILES: CC#C[C@@H](CC(=O)OCC)c1ccc(OCc2ccc(CCO)cc2)cc1]

The target compound was obtained by the same manner as described in step 2) of Manufacturing Example 6 except that 2-(4-(bromomethyl)phenyl)ethanol obtained in step 1) was used instead of (4-(bromomethyl)phenyl)methanol.

¹H NMR (400 MHz, CDCl₃): δ 7.40 (2H, d), 7.30 (2H, d), 7.27 (2H, d), 6.95 (2H, d), 5.04 (2H, s), 4.18 (2H, m), 4.11 (1H, m), 3.89 (2H, m), 2.91 (2H, m), 2.71 (2H, m), 1.84 (3H, s), 1.38 (1H, m), 1.25 (3H, m).

Step 3: Preparation of (S)-ethyl 3-(4-(4-(2-(methylsulfonyloxy)ethyl)benzyloxy)phenyl)hex-4-inoate

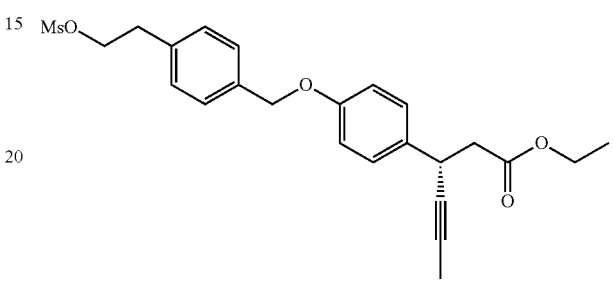

The target compound was obtained by the same manner as described in step 3) of Manufacturing Example 6 except that (S)-ethyl 3-(4-(4-(2-hydroxyethyl)benzyloxy)phenyl)hex-4-inoate obtained in step 2) was used instead of ethyl 3-(4-(4-(hydroxymethyl)benzyloxy)phenyl)hex-4-inoate.

¹H NMR (400 MHz, CDCl₃): δ 7.40 (2H, d), 7.30 (2H, d), 7.27 (2H, d), 6.95 (2H, d), 5.04 (2H, s), 4.18 (2H, m), 4.11 (1H, m), 3.99 (2H, m), 2.95 (3H, s), 2.93 (2H, m), 2.71 (2H, m), 1.84 (3H, s), 1.25 (3H, m).

Example 1: Preparation of 3-(4-(3-(1,4-dioxaspiro[4,5]dec-7-en-8-yl)benzyloxy)phenyl)hex-4-ynoic acid

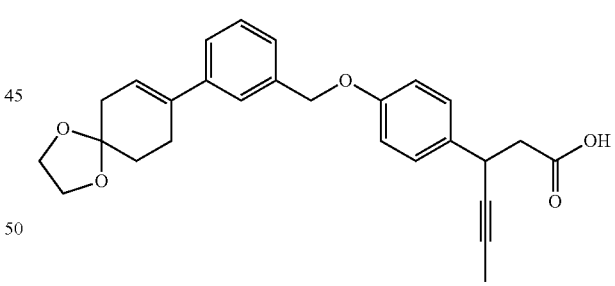

Step 1: Preparation of ethyl 3-(4-(3-(1,4-dioxaspiro[4,5]des-7-en-8-yl)benzyloxy)phenyl)hex-4-inoate (3-(1,4-dioxaspiro[4,5]des-7-en-8-yl)phenyl)methanol (19.54 g) prepared in Manufacturing Example 4 and tetrahydrofuran (80 mL) were loaded in a 500 mL flask in nitrogen atmosphere, followed by stirring for dissolving them. Then, ethyl 3-(4-hydroxyphenyl)hex-4-inoate (18.42 g) prepared in Manufacturing Example 1 and triphenyl phosphine (31.21 g) were slowly added thereto. Diisopropyl azodicarboxylate (23.4 mL) was slowly added thereto by using a dropping funnel at 0° C., followed by stirring for at least 4 hours with raising the temperature to room temperature. Upon completion of the reaction, distilled water (200 mL) was slowly added thereto, followed by extraction using ethylacetate (300 mL). The extracted organic layer was dried under reduced pressure to give the target compound (32.1 g, 87.9%).

$^1$H NMR (400 MHz, CDCl$_3$): δ 7.46 (1H, s), 7.31 (5H, m), 6.93 (2H, d), 6.02 (1H, m), 5.04 (2H, s), 4.13 (2H, m), 4.08 (1H, m), 4.04 (4H, s), 2.69 (4H, m), 2.49 (2H, s), 1.94 (2H, t), 1.84 (3H, d), 1.31 (3H, t).

Step 2: Preparation of 3-(4-(3-(1,4-dioxaspiro[4,5] des-7-en-8-yl)benzyloxy)phenyl)hex-4-inoic acid Ethyl 3-(4-(3-(1,4-dioxaspiro[4,5]des-7-en-8-yl)benzyloxy)phenyl)hex-4-inoate (32.1 g) prepared in step 1), methanol (50 mL), and distilled water (50 mL) were loaded in a 500 mL flask in nitrogen atmosphere, followed by stifling for dissolving them. Then, potassium hydroxide (19.5 g) was slowly added thereto at room temperature, followed by stifling at least 1 hour. Upon completion of the reaction, the mixture was acidized (pH: 2~3) by using 1 M HCl aqueous solution, followed by extraction using ethylacetate (300 mL). The extracted organic layer was dried under reduced pressure to give the target compound (24.1 g, 79.9%).

$^1$H NMR (400 MHz, CDCl$_3$): δ 7.44 (1H, s), 7.34 (5H, m), 6.91 (2H, d), 6.00 (1H, t), 5.02 (2H, s), 4.08 (1H, m), 4.04 (4H, s), 2.73 (4H, m), 2.48 (2H, s), 1.92 (2H, t), 1.82 (3H, s).

Example 2: Preparation of L-lysine 3-(4-(3-(1,4-dioxaspiro[4,5]dec-7-en-8-yl)benzyloxy)phenyl)hex-4-ynoate

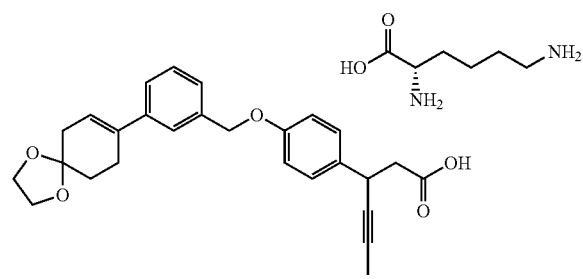

3-(4-(3-(1,4-dioxaspiro[4,5]des-7-en-8-yl)benzyloxy) phenyl)hex-4-inoic acid (24.1 g) prepared in Example 1 and ethanol (170 mL) were loaded in a 500 mL flask in nitrogen atmosphere, followed by stirring for dissolving them. Then, L-lysine (7.33 g) was added thereto. The reaction temperature was raised to 50° C. and the mixture was stirred for 30 minutes at 50° C. The mixture was cooled down to room temperature, followed by stifling for 30 minutes. Upon completion of the reaction, the produced solid was filtered to give the target compound (31.5 g, 73.3%).

$^1$H NMR (400 MHz, D$_2$O): δ 7.11 (3H, m), 6.99 (3H, m), 6.64 (2H, d), 5.65 (1H, s), 4.59 (2H, s), 3.79 (5H, s), 3.60 (1H, t), 2.88 (2H, t), 2.35 (2H, d), 2.23 (2H, s), 2.14 (2H, s), 1.75 (2H, m), 1.59 (7H, m), 1.38 (2H, m).

Example 3: Preparation of 4-(4-(3-(1,4-dioxaspiro [4,5]dec-7-en-8-yl)benzyloxy)phenyl)hex-4-ynoic acid

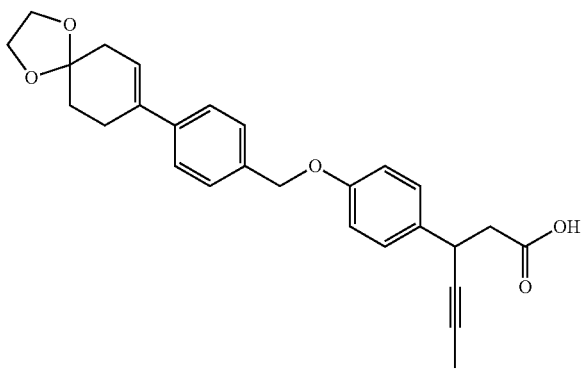 [SMILES: CC#CC(CC(=O)O)c1ccc(OCc2ccc(C3=CCC4(CC3)OCCO4)cc2)cc1]

Step 1: Preparation of ethyl 4-(4-(3-(1,4-dioxaspiro [4,5]des-7-en-8-yl)benzyloxy)phenyl)hex-4-inoate (4-(1,4-dioxaspiro[4,5]des-7-en-8-yl)phenyl)methanol (1.5 g) prepared in Manufacturing Example 5 and tetrahydrofuran (20 mL) were loaded in a 100 mL flask in nitrogen atmosphere, followed by stirring for dissolving them. Then, ethyl 3-(4-hydroxyphenyl)hex-4-inoate (1.41 g) prepared in Manufacturing Example 1 and triphenyl phosphine (2.39 g) were slowly added thereto. Diisopropyl azodicarboxylate (9.38 mL) was slowly added thereto by using a dropping funnel at 0° C., followed by stirring for at least 4 hours with raising the temperature to room temperature. Upon completion of the reaction, distilled water (50 mL) was slowly added thereto, followed by extraction using ethylacetate (100 mL). The extracted organic layer was dried under reduced pressure to give the target compound (1.38 g, 49.2%).

$^1$H NMR (400 MHz, CDCl$_3$): δ 7.42 (2H, d), 7.37 (2H, d), 7.30 (2H, d), 6.92 (2H, d), 6.01 (1H, s), 5.01 (2H, s), 4.14 (2H, m), 4.06 (5H, m), 2.70 (4H, m), 2.49 (2H, s), 1.94 (2H, t), 1.84 (3H, d), 1.24 (3H, t).

Step 2: Preparation of 4-(4-(3-(1,4-dioxaspiro[4,5] des-7-en-8-yl)benzyloxy)phenyl)hex-4-inoic acid Ethyl 4-(4-(3-(1,4-dioxaspiro[4,5]des-7-en-8-yl)benzyloxy)phenyl)hex-4-inoate (1.38 g) prepared in step 1), methanol (10 mL), and distilled water (10 mL) were loaded in a 500 mL flask in nitrogen atmosphere, followed by stifling for dissolving them. Then, potassium hydroxide (1.25 g) was slowly added thereto at room temperature, followed by stifling for at least 1 hour. Upon completion of the reaction, the mixture was acidized (pH: 2~3) by using 1 M HCl aqueous solution, followed by extraction using ethylacetate (50 mL). The extracted organic layer was dried under reduced pressure to give the target compound (0.98 g, 75.6%).

$^1$H NMR (400 MHz, CDCl$_3$): δ 7.41 (2H, d), 7.36 (2H, d), 7.29 (2H, d), 6.92 (2H, d), 6.01 (1H, s), 5.01 (2H, s), 4.04 (5H, m), 2.77 (4H, m), 2.49 (2H, s), 1.96 (2H, t), 1.83 (3H, d).

Example 4: Preparation of 3-(4-(3-(4-oxocyclohex-1-enyl)benzyloxy)phenyl)hex-4-ynoic acid

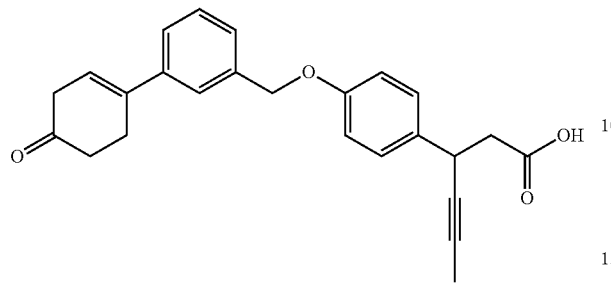

3-(4-(3-(1,4-dioxaspiro[4,5]des-7-en-8-yl)benzyloxy)phenyl)hex-4-inoic acid (1 g) prepared in Example 1 and tetrahydrofuran (5 mL) were loaded in a flask in nitrogen atmosphere, followed by stifling for dissolving them. 6 N HCl aqueous solution (5 mL) was added thereto, followed by stifling at room temperature for at least 1 hour. Upon completion of the reaction, distilled water (50 mL) was slowly added thereto, followed by extraction using ethylacetate (50 mL). The extracted organic layer was dried under reduced pressure to give the target compound (0.76 g, 84.6%).

$^1$H NMR (400 MHz, CDCl$_3$): δ 7.48 (1H, s), 7.40 (5H, m), 6.94 (2H, d), 6.13 (1H, s), 5.07 (2H, s), 4.05 (1H, m), 3.10 (1.5H, t), 2.93 (1.5H, t), 2.82 (2H, m), 2.67 (2H, t), 1.85 (3H, s).

Example 5: Preparation of 3-(4-(3-(4-hydroxycyclohex-1-enyl)benzyloxy)phenyl)hex-4-ynoic acid

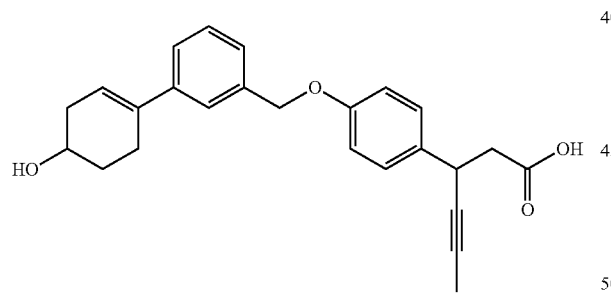

3-(4-(3-(4-oxocyclohex-1-enyl)benzyloxy)phenyl)hex-4-inoic acid (1 g) prepared in Example 4 and ethanol (10 mL) were loaded in a 100 mL flask in nitrogen atmosphere, followed by stifling for dissolving them. Then, sodium borohydride (0.3 g) was added thereto at room temperature, followed by stifling for at least 3 hours. Upon completion of the reaction, the mixture was acidized (pH: 4~5) by using 1 N HCl aqueous solution, followed by extraction using ethylacetate (100 mL) and distilled water (100 mL). The extracted organic layer was dried under reduced pressure to give the target compound (0.81 g, 80.6%).

$^1$H NMR (400 MHz, CDCl$_3$): δ 7.44 (1H, s), 7.33 (5H, m), 6.93 (2H, d), 6.02 (1H, s), 5.03 (2H, s), 4.08 (2H, s), 2.78 (2H, m), 2.55 (2.5H, m), 2.22 (1H, m), 2.04 (1H, m), 1.85 (3H, s).

Example 6: Preparation of L-lysine 3-(4-(3-(4-hydroxycyclohex-1-enyl)benzyloxy)phenyl)hex-4-ynoate

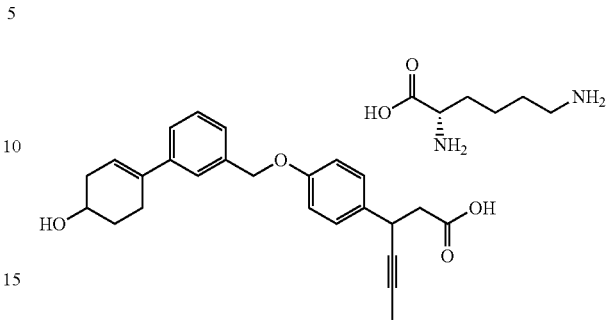

3-(4-(3-(4-hydroxycyclohex-1-enyl)benzyloxy)phenyl)hex-4-inoic acid (1 g) prepared in Example 5 and ethanol (170 mL) were loaded in a 100 mL flask in nitrogen atmosphere, followed by stifling for dissolving them. Then, L-lysine (0.7 g) was added thereto. The reaction temperature was raised to 50° C. and the mixture was stirred for 30 minutes at 50° C. The mixture was cooled down to room temperature, followed by stirring for 30 minutes. Upon completion of the reaction, the produced solid was filtered to give the target compound (0.95 g, 69.1%).

$^1$H NMR (400 MHz, D$_2$O): δ 7.11 (3H, m), 6.99 (3H, m), 6.64 (2H, d), 5.65 (1H, s), 4.59 (2H, s), 3.79 (1H, s), 3.60 (1H, t), 2.88 (2H, t), 2.35 (2H, d), 2.23 (2H, s), 2.14 (2H, s), 1.75 (2H, m), 1.59 (7H, m), 1.38 (2H, m).

Example 7: Preparation of (3S)-3-(4-(3-(1,4-dioxaspiro[4,5]dec-7-en-8-yl)benzyloxy)phenyl)hex-4-ynoic acid

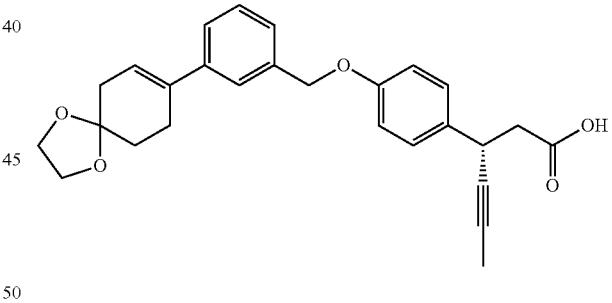

Step 1: Preparation of ethyl-(3S)-3-(4-(3-(1,4-dioxaspiro[4,5]des-7-en-8-yl)benzyloxy)phenyl)hex-4-inoate (3-(1,4-dioxaspiro[4,5]des-7-en-8-yl)phenyl)methanol (19.54 g) prepared in Manufacturing Example 4 and tetrahydrofuran (80 mL) were loaded in a 500 mL flask in nitrogen atmosphere, followed by stirring for dissolving them. Then, (S)-ethyl 3-(4-hydroxyphenyl)hex-4-inoate (18.42 g) prepared in Manufacturing Example 2 and triphenyl phosphine (31.21 g) were slowly added thereto. Diisopropyl azodicarboxylate (23.4 mL) was slowly added thereto by using a dropping funnel at 0° C., followed by stirring for at least 4 hours with raising the temperature to room temperature. Upon completion of the reaction, distilled water (200 mL) was slowly added thereto, followed by extraction using ethylacetate (300 mL). The extracted organic layer was dried under reduced pressure to give the target compound.

¹H NMR (400 MHz, CDCl₃): δ 7.46 (1H, s), 7.31 (5H, m), 6.93 (2H, d), 6.02 (1H, m), 5.04 (2H, s), 4.13 (2H, m), 4.08 (1H, m), 4.04 (4H, s), 2.69 (4H, m), 2.49 (2H, s), 1.94 (2H, t), 1.84 (3H, d), 1.31 (3H, t).

Step 2: Preparation of (3S)-3-(4-(3-(1,4-dioxaspiro[4,5]des-7-en-8-yl)benzyloxy)phenyl)hex-4-inoic acid Ethyl-(3S)-3-(4-(3-(1,4-dioxaspiro[4,5]des-7-en-8-yl)benzyloxy)phenyl)hex-4-inoate (32.1 g) prepared in step 1), methanol (50 mL), and distilled water (50 mL) were loaded in a 500 mL flask in nitrogen atmosphere, followed by stirring for dissolving them. Then, potassiumhydroxide (19.5 g) was slowly added thereto at room temperature, followed by stifling for at least 1 hour. Upon completion of the reaction, the mixture was acidized (pH: 2~3) by using 1 M HCl aqueous solution, followed by extraction using ethylacetate (300 mL). The extracted organic layer was dried under reduced pressure to give the target compound (24.1 g, 66.2%).

¹H NMR (400 MHz, CDCl₃): δ 7.44 (1H, s), 7.34 (5H, m), 6.91 (2H, d), 6.00 (1H, t), 5.02 (2H, s), 4.08 (1H, m), 4.04 (4H, s), 2.73 (4H, m), 2.48 (2H, s), 1.92 (2H, t), 1.82 (3H, s).

Example 8: Preparation of (3R)-3-(4-(3-(1,4-dioxaspiro[4,5]dec-7-en-8-yl)benzyloxy)phenyl)hex-4-ynoic acid

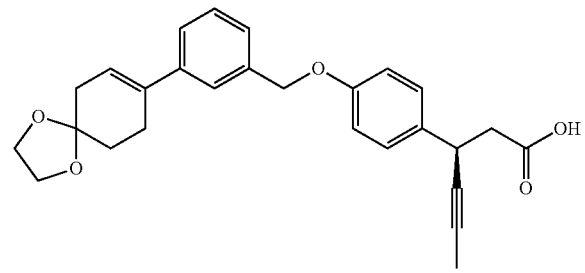 [SMILES: CC#C[C@H](CC(=O)O)c1ccc(OCc2cccc(C3=CCC4(CC3)OCCO4)c2)cc1]

Step 1: Preparation of ethyl-(3R)-3-(4-(3-(1,4-dioxaspiro[4,5]des-7-en-8-yl)benzyloxy)phenyl)hex-4-inoate (3-(1,4-dioxaspiro[4,5]des-7-en-8-yl)phenyl)methanol (19.54 g) prepared in Manufacturing Example 4 and tetrahydrofuran (80 mL) were loaded in a 500 mL flask in nitrogen atmosphere, followed by stirring for dissolving them. Then, (R)-ethyl 3-(4-hydroxyphenyl)hex-4-inoate (18.42 g) prepared in Manufacturing Example 3 and triphenyl phosphine (31.21 g) were slowly added thereto. Diisopropyl azodicarboxylate (23.4 mL) was slowly added thereto by using a dropping funnel at 0° C., followed by stirring for at least 4 hours with raising the temperature to room temperature. Upon completion of the reaction, distilled water (200 mL) was slowly added thereto, followed by extraction using ethylacetate (300 mL). The extracted organic layer was dried under reduced pressure to give the target compound.

¹H NMR (400 MHz, CDCl₃): δ 7.46 (1H, s), 7.31 (5H, m), 6.93 (2H, d), 6.02 (1H, m), 5.04 (2H, s), 4.13 (2H, m), 4.08 (1H, m), 4.04 (4H, s), 2.69 (4H, m), 2.49 (2H, s), 1.94 (2H, t), 1.84 (3H, d), 1.31 (3H, t).

Step 2: Preparation of (3R)-3-(4-(3-(1,4-dioxaspiro[4,5]des-7-en-8-yl)benzyloxy)phenyl)hex-4-inoic acid Ethyl-(3R)-3-(4-(3-(1,4-dioxaspiro[4,5]des-7-en-8-yl)benzyloxy)phenyl)hex-4-inoate (32.1 g) prepared in step 1), methanol (50 mL), and distilled water (50 mL) were loaded in a 500 mL flask in nitrogen atmosphere, followed by stirring for dissolving them. Then, potassium hydroxide (19.5 g) was slowly added thereto at room temperature, followed by stifling for at least 1 hour. Upon completion of the reaction, the mixture was acidized (pH: 2~3) by using 1 M HCl aqueous solution, followed by extraction using ethylacetate (300 mL). The extracted organic layer was dried under reduced pressure to give the target compound (17.3 g, 47.5%).

¹H NMR (400 MHz, CDCl₃): δ 7.44 (1H, s), 7.34 (5H, m), 6.91 (2H, d), 6.00 (1H, t), 5.02 (2H, s), 4.08 (1H, m), 4.04 (4H, s), 2.73 (4H, m), 2.48 (2H, s), 1.92 (2H, t), 1.82 (3H, s).

Example 9: Preparation of L-lysine (3S)-3-(4-(3-(1,4-dioxaspiro[4,5]dec-7-en-8-yl)benzyloxy)phenyl)hex-4-ynoate

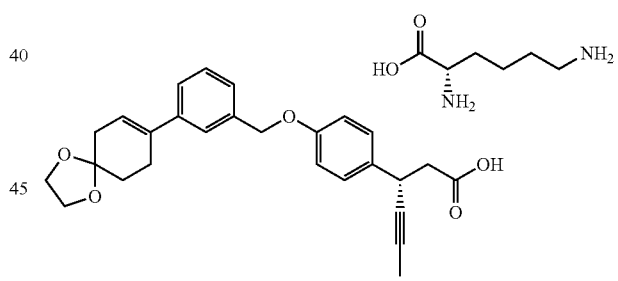

(3S)-3-(4-(3-(1,4-dioxaspiro[4,5]des-7-en-8-yl)benzyloxy)phenyl)hex-4-inoic acid (24.1 g) prepared in Example 7 and ethanol (170 mL) were loaded in a 500 mL flask in nitrogen atmosphere, followed by stirring for dissolving them. Then, L-lysine (7.33 g) was added thereto. The reaction temperature was raised to 50° C. and the mixture was stirred for 30 minutes at 50° C. The mixture was cooled down to room temperature, followed by stifling for 30 minutes. Upon completion of the reaction, the produced solid was filtered to give the target compound (22.5 g, 69.8%).

¹H NMR (400 MHz, D₂O): δ 7.11 (3H, m), 6.99 (3H, m), 6.64 (2H, d), 5.65 (1H, s), 4.59 (2H, s), 3.79 (5H, s), 3.60 (1H, t), 2.88 (2H, t), 2.35 (2H, d), 2.23 (2H, s), 2.14 (2H, s), 1.75 (2H, m), 1.59 (7H, m), 1.38 (2H, m).

Example 10: Preparation of L-lysine (3R)-3-(4-(3-(1,4-dioxaspiro[4,5]dec-7-en-8-yl)benzyloxy)phenyl)hex-4-ynoate L-lysinate

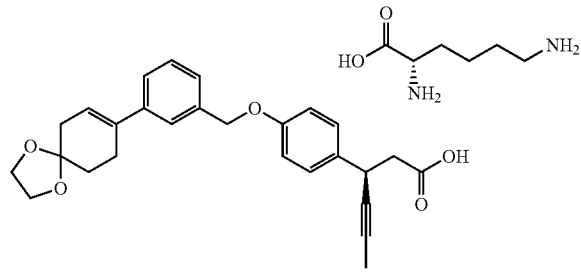 [SMILES: CC#C[C@H](CC(=O)O)c1ccc(OCc2cccc(C3=CCC4(CC3)OCCO4)c2)cc1 ; NCCCC[C@H](N)C(=O)O]

(3R)-3-(4-(3-(1,4-dioxaspiro[4,5]des-7-en-8-yl)benzyloxy)phenyl)hex-4-inoic acid (24.1 g) prepared in Example 8 and ethanol (170 mL) were loaded in a 500 mL flask in nitrogen atmosphere, followed by stirring for dissolving them. Then, L-lysine (7.33 g) was added thereto. The reaction temperature was raised to 50° C. and the mixture was stirred for 30 minutes at 50° C. The mixture was cooled down to room temperature, followed by stifling for 30 minutes. Upon completion of the reaction, the produced solid was filtered to give the target compound (16.2 g, 71.4%).

$^1$H NMR (400 MHz, D$_2$O): δ 7.11 (3H, m), 6.99 (3H, m), 6.64 (2H, d), 5.65 (1H, s), 4.59 (2H, s), 3.79 (5H, s), 3.60 (1H, t), 2.88 (2H, t), 2.35 (2H, d), 2.23 (2H, s), 2.14 (2H, s), 1.75 (2H, m), 1.59 (7H, m), 1.38 (2H, m).

Example 11: Preparation of sodium (3S)-3-(4-(3-(1,4-dioxaspiro[4,5]dec-7-en-8-yl)benzyloxy)phenyl)hex-4-ynoate

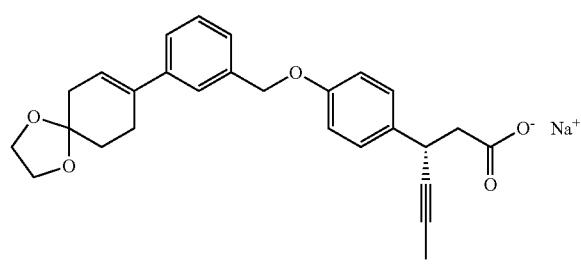 [SMILES: CC#C[C@@H](CC(=O)[O-])c1ccc(OCc2cccc(C3=CCC4(CC3)OCCO4)c2)cc1 ; [Na+]]

(3S)-3-(4-(3-(1,4-dioxaspiro[4,5]des-7-en-8-yl)benzyloxy)phenyl)hex-4-inoic acid (1 g) prepared in Example 7 and ethanol (170 mL) were loaded in a 500 mL flask in nitrogen atmosphere, followed by stirring for dissolving them. Then, 3 N sodiumhydroxide aqueous solution (0.77 mL) was added thereto, followed by stirring at room temperature. Upon completion of the reaction, the reaction mixture was concentrated under reduced pressure. Then, isopropylalcohol (10 mL) was added thereto, and the produced solid was filtered to give the target compound (0.73 g, 69.2%).

$^1$H NMR (400, CDCl$_3$): δ 7.44 (1H, s), 7.34 (5H, m), 6.91 (2H, d), 6.00 (1H, t), 5.02 (2H, s), 4.08 (1H, m), 4.04 (4H, s), 2.73 (4H, m), 2.48 (2H, s), 1.92 (2H, t), 1.82 (3H, s)

Example 12: Preparation of 3-(4-(4-((3,4-dihydroisoquinoline-2(1H)-yl)methyl)benzyloxy) phenyl)hex-4-ynoic acid

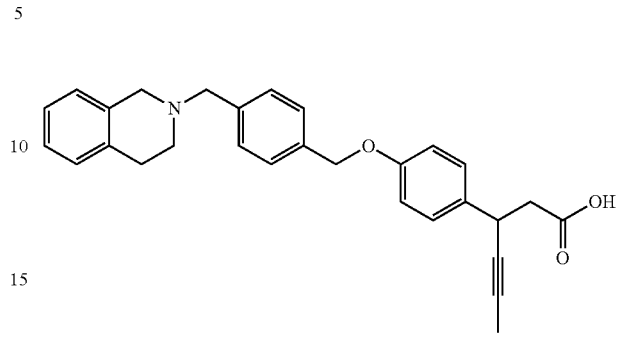

Step 1: Preparation of ethyl 3-(4-(4-((3,4-dihydroisoquinoline-2(1H)-yl)methyl)benzyloxy)phenyl)hex-4-inoate 0.5 g of 1,2,3,4-tetrahydroisoquinoline was loaded in 20 mL of DMF in a flask in nitrogen atmosphere, followed by stirring. 1.2 g of cesiumcarbonate was added thereto at room temperature. 30 minutes later, 1.0 g of ethyl 3-(4-(4-((methylsulfonyloxy)methyl)benzyloxy)phenyl)hex-4-inoate prepared in Manufacturing Example 6 was added thereto, followed by stirring at room temperature for 12 hours. Upon completion of the reaction, distilled water was slowly added thereto, followed by extraction using ethylacetate. The extract was washed with brine, dried over anhydrous MgSO$_4$, and concentrated. Then, silica gel column chromatography was performed to give the target compound.

$^1$H NMR (400 MHz, CDCl$_3$): δ 7.38 (2H, d), 7.31 (2H, d), 7.22 (2H, d), 7.16 (3H, m), 6.97 (3H, m), 4.98 (2H, s), 4.14 (2H, m), 4.09 (1H, s), 3.91 (1H, d), 3.70 (3H, m), 2.92 (4H, s), 2.73 (2H, m), 1.83 (3H, s), 1.29 (3H, m).

Step 2: Preparation of 3-(4-(4-((3,4-dihydroisoquinoline-2(1H)-yl)methyl)benzyloxy) phenyl)hex-4-inoic acid 0.7 g of ethyl 3-(4-(4-((3,4-dihydroisoquinoline-2(1H)-yl)methyl)benzyloxy)phenyl)hex-4-inoate prepared in step 1), THF, and distilled water were loaded in a flask in nitrogen atmosphere, followed by stifling for dissolving them. Then, lithium hydroxide (0.7 g) was slowly added thereto at room temperature, followed by stifling for at least 1 hour. Upon completion of the reaction, the mixture was acidized (pH: 2~3) by using 1 M HCl aqueous solution, followed by extraction using ethylacetate. The extract was dried under reduced pressure to give the target compound.

$^1$H NMR (400 MHz, CDCl$_3$): δ 7.38 (2H, d), 7.31 (2H, d), 7.22 (2H, d), 7.16 (3H, m), 6.97 (3H, m), 4.98 (2H, s), 4.09 (1H, s), 3.91 (1H, d), 3.70 (3H, m), 2.92 (4H, s), 2.73 (2H, m), 1.83 (3H, s).

Example 13: Preparation of 3-(4-(3-cyclohexenyl-4-((3,4-dihydroisoquinoline-2(1H)-yl)methyl)benzyloxy)phenyl)hex-4-ynoic acid

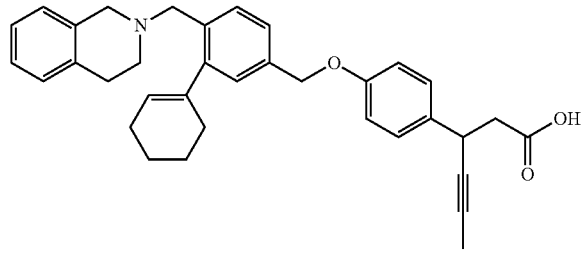 [SMILES: CC#CC(CC(=O)O)c1ccc(OCc2ccc(CN3CCc4ccccc4C3)c(C3=CCCCC3)c2)cc1]

Step 1: Preparation of ethyl 3-(4-(3-cyclohexenyl-4-((3,4-dihydroisoquinoline-2(1H)-yl)methyl)benzyloxy)phenyl)hex-4-inoate 1.0 g of (3-cyclohexenyl-4-((3,4-dihydroisoquinoline-2(1H)-yl)methyl)phenyl)methanol and 30 ml of tetrahydrofuran were loaded in a flask in nitrogen atmosphere, followed by stirring for dissolving them. Then, 0.8 g of ethyl 3-(4-hydroxyphenyl)hex-4-inoate prepared in Manufacturing Example 1 and 0.6 g of triphenyl phosphine were slowly added thereto. 0.5 ml of diisopropyl azodicarboxylate was slowly added thereto by using a dropping funnel at 0° C., followed by stifling for at least 4 hours with raising the temperature to room temperature. Upon completion of the reaction, distilled water was slowly added thereto, followed by extraction using ethylacetate. The extracted organic layer was dried under reduced pressure to give the target compound.

$^1$H NMR (400 MHz, CDCl$_3$): δ 12.56 (1H, s), 8.26 (1H, d), 7.43 (2H, d), 7.25 (6H, m), 7.21 (1H, d), 7.02 (1H, d), 6.89 (2H, d), 5.46 (1H, s), 5.03 (2H, s), 4.14 (2H, m), 4.05 (1H, s), 3.92 (1H, s), 3.70 (1H, s), 3.35 (1H, s), 3.27 (1H, s), 3.03 (1H, s), 2.83 (2H, m), 2.01 (4H, m), 1.84 (3H, d), 1.51 (4H, m), 1.29 (3H, m).

Step 2: Preparation of 3-(4-(3-cyclohexenyl-4-((3,4-dihydroisoquinoline-2(1H)-yl)methyl) benzyloxy)phenyl)hex-4-inoic acid The target compound was obtained by the same manner as described in step 2) of Example 12 except that ethyl 3-(4-(3-cyclohexenyl-4-((3,4-dihydroisoquinoline-2(1H)-yl)methyl)benzyloxy)phenyl)hex-4-inoate was used instead of ethyl 3-(4-(4-((3,4-dihydroisoquinoline-2(1H)-yl)methyl)benzyloxy)phenyl)hex-4-inoate.

$^1$H NMR (400 MHz, CDCl$_3$): δ 12.56 (1H, s), 8.26 (1H, d), 7.43 (2H, d), 7.25 (6H, m), 7.21 (1H, d), 7.02 (1H, d), 6.89 (2H, d), 5.46 (1H, s), 5.03 (2H, s), 4.05 (1H, s), 3.92 (1H, s), 3.70 (1H, s), 3.35 (1H, s), 3.27 (1H, s), 3.03 (1H, s), 2.83 (2H, m), 2.01 (4H, m), 1.84 (3H, d), 1.51 (4H, m).

Example 14: Preparation of 3-(4-(4-((4-phenyl-5,6-dihydropyridine-1(2H)-yl)methyl) benzyloxy)phenyl)hex-4-ynoic acid

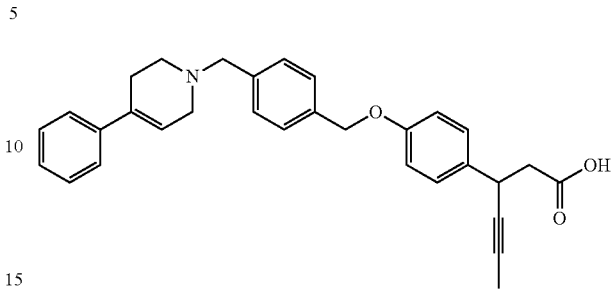

The target compound was obtained by the same manner as described in Example 12 except that 4-phenyl-1,2,3,6-tetrahydropyridine hydrochloride was used instead of 1,2,3,4-tetrahydroisoquinoline.

$^1$H NMR (400 MHz, CDCl$_3$): δ 7.25 (2H, d), 6.78 (2H, d), 4.95 (1H, s), 4.14 (2H, m), 4.04 (1H, m), 2.68 (2H, m), 1.84 (3H, d), 1.29 (3H, t).

Example 15: Preparation of 3-(4-(4-((4-phenylpiperazine-1-yl)methyl)benzyloxy)phenyl)hex-4-ynoic acid

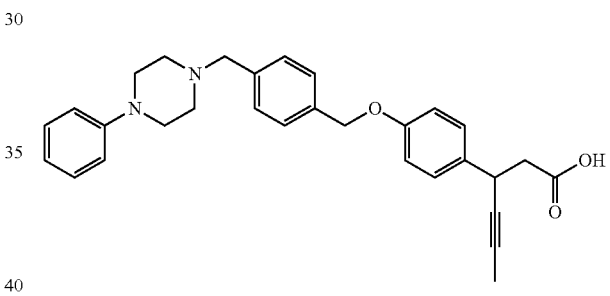

The target compound was obtained by the same manner as described in Example 12 except that 1-phenylpiperazine was used instead of 1,2,3,4-tetrahydroisoquinoline.

$^1$H NMR (400 MHz, CDCl$_3$): δ 7.37 (2H, d), 7.29 (4H, m), 7.11 (2H, d), 6.93 (5H, m), 4.96 (2H, s), 4.13 (1H, s), 3.66 (2H, m), 3.23 (4H, s), 2.83 (2H, m), 2.66 (2H, s), 1.82 (3H, s).

Example 16: Preparation of 3-(4-(4-((6-methoxy-3,4-dihydroisoquinoline-2(1H)-yl)methyl) benzyloxy)phenyl)hex-4-ynoic acid

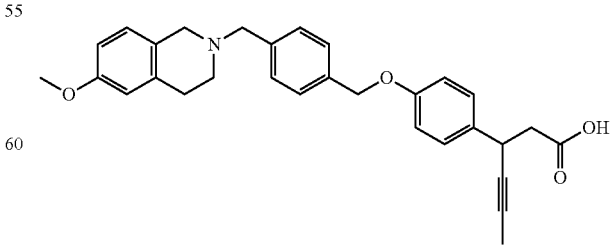

The target compound was obtained by the same manner as described in Example 12 except that 6-methoxy-1,2,3,4- tetrahydroisoquinoline obtained in Manufacturing Example 8 was used instead of 1,2,3,4-tetrahydroisoquinoline.

¹H NMR (400 MHz, CDCl₃): δ 7.40 (4H, q), 7.26 (2H, d), 6.92 (3H, q), 6.66 (2H, d), 5.06 (2H, s), 3.94 (1H, s), 3.73 (3H, s), 3.63 (2H, s), 3.35 (3H, s), 2.78 (2H, t), 2.62 (2H, t), 2.58 (2H, s), 1.77 (3H, s).

Example 17: Preparation of 3-(4-(4-((4-phenylpiperidine-1-yl)methyl)benzyloxy)phenyl)hex-4-ynoic acid

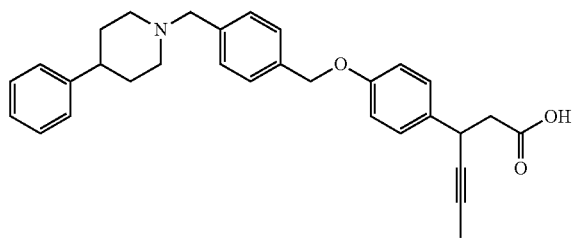 [SMILES: CC#CC(CC(=O)O)c1ccc(OCc2ccc(CN3CCC(c4ccccc4)CC3)cc2)cc1]

The target compound was obtained by the same manner as described in Example 12 except that 4-phenylpiperidine was used instead of 1,2,3,4-tetrahydroisoquinoline.

¹H NMR (400 MHz, CDCl₃): δ 7.44 (2H, d), 7.32 (2H, d), 7.23 (5H, t), 7.13 (2H, d), 6.96 (2H, d), 4.92 (2H, s), 4.16 (1H, s), 3.85 (2H, q), 3.33 (2H, t), 2.90 (1H, d), 2.78 (1H, m), 2.58 (1H, t), 2.38 (2H, t), 2.02 (2H, m), 1.83 (5H, m).

Example 18: Preparation of 3-(4-(4-((4-(4-fluorophenyl)piperazine-1-yl)methyl)benzyloxy) phenyl) hex-4-ynoic acid

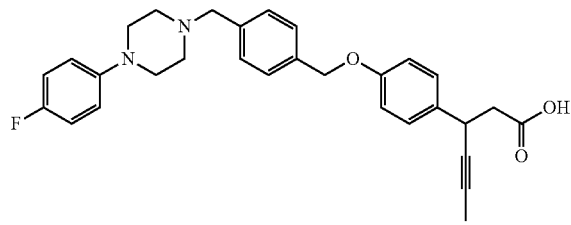 [SMILES: CC#CC(CC(=O)O)c1ccc(OCc2ccc(CN3CCN(c4ccc(F)cc4)CC3)cc2)cc1]

The target compound was obtained by the same manner as described in Example 12 except that 1-(4-fluorophenyl) piperazine was used instead of 1,2,3,4-tetrahydroisoquinoline.

¹H NMR (400 MHz, CDCl₃): δ 7.60 (2H, d), 7.46 (2H, d), 7.30 (3H, d), 6.97 (2H, t), 6.86 (4H, m), 5.01 (2H, s), 4.21 (2H, s), 4.04 (1H, t), 3.50 (4H, d), 3.25 (4H, s), 2.78 (2H, m), 1.80 (3H, d).

Example 19: Preparation of 3-(4-(4-((4-(4-(trifluoromethyl)phenyl)piperazine-1-yl)methyl) benzyloxy)phenyl)hex-4-ynoic acid

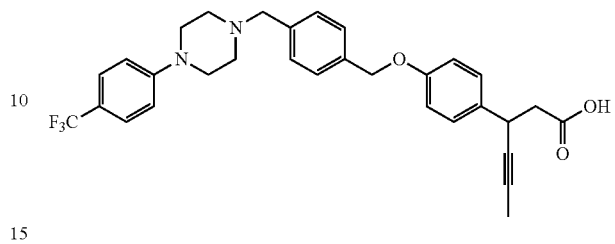

The target compound was obtained by the same manner as described in Example 12 except that 1-(4-(trifluoromethyl) phenyl)piperazine was used instead of 1,2,3,4-tetrahydroisoquinoline.

¹H NMR (400 MHz, CDCl₃): δ 7.63 (2H, d), 7.51 (4H, d), 7.21 (2H, d), 6.93 (2H, d), 6.74 (2H, s), 5.03 (2H, s), 4.13 (2H, m), 4.01 (1H, t), 3.73 (4H, s), 2.96 (4H, s), 2.71 (2H, m), 1.78 (3H, s).

Example 20: Preparation of 3-(4-(4-((4-(4-(3-(methylsulfonyl)propoxy)phenyl)piperazine-1-yl)methyl) benzyloxy)phenyl)hex-4-ynoic acid

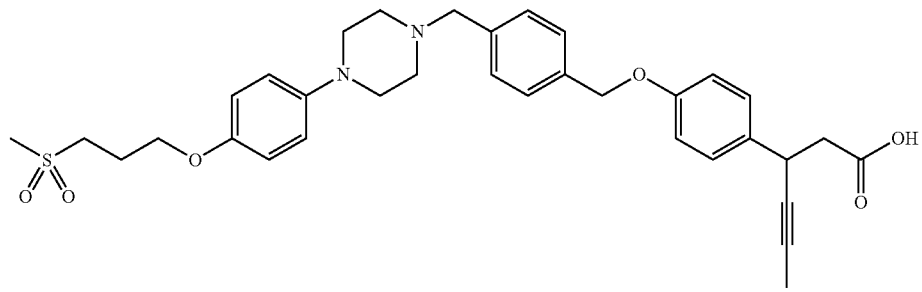 [SMILES: CC#CC(CC(=O)O)c1ccc(OCc2ccc(CN3CCN(c4ccc(OCCCS(C)(=O)=O)cc4)CC3)cc2)cc1]

The target compound was obtained by the same manner as described in Example 12 except that 1-(4-(3-(methylsulfonyl)propoxy)phenyl)piperazine hydrochloride was used instead of 1,2,3,4-tetrahydroisoquinoline.

¹H NMR (400 MHz, CDCl₃): δ 7.65 (2H, d), 7.49 (2H, d), 7.30 (2H, d), 6.87 (6H, m), 5.07 (2H, s), 4.20 (2H, d), 4.08 (2H, t), 4.01 (1H, t), 6.63 (2H, s), 3.49 (4H, m), 3.26 (2H, t), 3.01 (2H, s), 2.97 (3H, s), 2.71 (2H, m), 2.34 (2H, m), 1.83 (2H, d).

Example 21: Preparation of (S)-3-(4-(4-((3,4-dihydroisoquinoline-2(1H)-yl)methyl) benzyloxy)phenyl)hex-4-ynoic acid

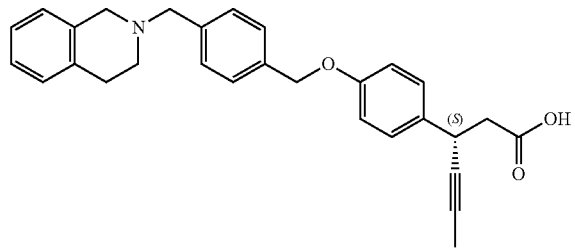

Step 1: Preparation of ethyl (S)-3-(4-(4-((3,4-dihydroisoquinoline-2(1H)-yl)methyl)benzyloxy)phenyl)hex-4-inoate 0.5 g of 1,2,3,4-tetrahydroisoquinoline was loaded in 20 mL of DMF in a flask in nitrogen atmosphere, followed by stirring. 1.1 g of cesiumcarbonate was added thereto at room temperature. 30 minutes later, 1.0 g of (S)-ethyl 3-(4-(4-((methylsulfonyloxy)methyl)benzyloxy)phenyl)hex-4-inoate prepared in Manufacturing Example 7 was added thereto, followed by stirring at room temperature for 12 hours. Upon completion of the reaction, distilled water was slowly added thereto, followed by extraction using ethylacetate. The extract was washed with brine, dried over anhydrous MgSO$_4$, and concentrated. Then, silica gel column chromatography was performed to give the target compound.

$^1$H NMR (400 MHz, CDCl$_3$): δ 7.38 (2H, d), 7.31 (2H, d), 7.22 (2H, d), 7.16 (3H, m), 6.97 (3H, m), 4.98 (2H, s), 4.14 (2H, m), 4.09 (1H, s), 3.91 (1H, d), 3.70 (3H, m), 2.92 (4H, s), 2.73 (2H, m), 1.83 (3H, s), 1.29 (3H, m).

Step 2: Preparation of (S)-3-(4-(4-((3,4-dihydroisoquinoline-2(1H)-yl)methyl)benzyloxy)phenyl)hex-4-inoic acid 0.5 g of (S)-3-(4-(4-((3,4-dihydroisoquinoline-2(1H)-yl)methyl)benzyloxy)phenyl)hex-4-inoate prepared in step 1), THF, methanol, and distilled water were loaded in a flask in nitrogen atmosphere, followed by stifling for dissolving them. Then, 0.5 g of lithium hydroxide was slowly added thereto at room temperature, followed by stifling for at least 1 hour. Upon completion of the reaction, the mixture was acidized (pH: 2~3) by using 1 M HCl aqueous solution, followed by extraction using ethylacetate. The extract was dried under reduced pressure to give the target compound.

$^1$H NMR (400 MHz, CDCl$_3$): δ 7.38 (2H, d), 7.31 (2H, d), 7.22 (2H, d), 7.16 (3H, m), 6.97 (3H, m), 4.98 (2H, s), 4.09 (1H, s), 3.91 (1H, d), 3.70 (3H, m), 2.92 (4H, s), 2.73 (2H, m), 1.83 (3H, s).

Example 22: Preparation of (S)-3-(4-(4-((4-(4-(trifluoromethyl)phenyl)piperazine-1-yl)methyl)benzyloxy)phenyl)hex-4-ynoic acid

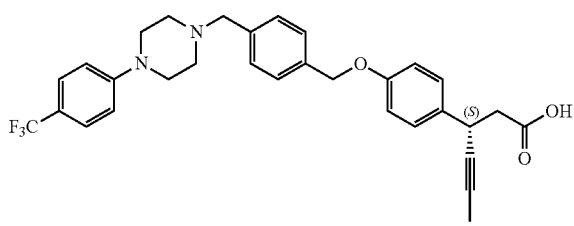

The target compound was obtained by the same manner as described in Example 21 except that 1-(4-(trifluoromethyl)phenyl)piperazine was used instead of 1,2,3,4-tetrahydroisoquinoline.

$^1$H NMR (400 MHz, CDCl$_3$): δ 7.65 (2H, d), 7.51 (4H, m), 7.30 (2H, d), 6.61 (2H, d), 6.85 (2H, d), 5.05 (2H, s), 4.21 (2H, s), 4.03 (1H, t), 3.68 (4H, s), 3.49 (2H, s), 2.84 (2H, s), 2.70 (2H, m), 1.82 (3H, s).

Example 23: Preparation of (S)-3-(4-(4-((4-(4-fluorophenyl)piperazine-1-yl)methyl)benzyloxy)phenyl)hex-4-ynoic acid

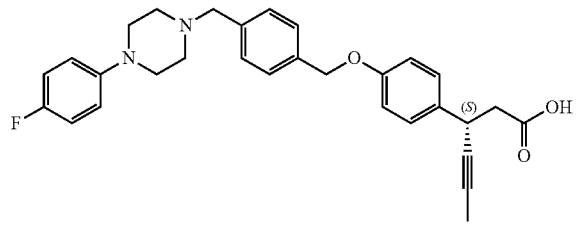

The target compound was obtained by the same manner as described in Example 21 except that 1-(4-fluorophenyl)piperazine was used instead of 1,2,3,4-tetrahydroisoquinoline.

$^1$H NMR (400 MHz, CDCl$_3$): δ 7.39 (2H, d), 7.30 (2H, d), 7.19 (2H, d), 6.96 (4H, m), 6.87 (2H, m), 4.97 (2H, s), 4.10 (2H, s), 3.81 (1H, d), 3.51 (1H, d), 3.15 (4H, s), 2.80 (6H, m), 1.82 (3H, s).

Example 24: Preparation of potassium (S)-3-(4-(4-((4-(4-(trifluoromethyl)phenyl)piperazine-1-yl)methyl)benzyloxy)phenyl)hex-4-ynoate

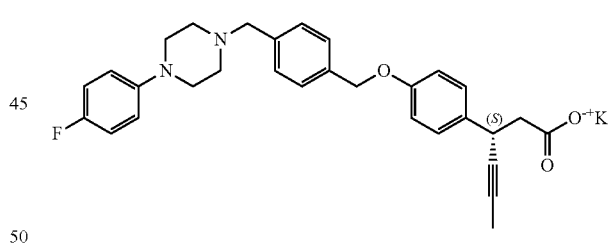

0.4 g of (S)-3-(4-(4-((4-(4-fluorophenyl)piperazine-1-yl)methyl)benzyloxy)phenyl)hex-4-inoic acid prepared in Example 23 and 10 ml of ethanol were loaded in a flask in nitrogen atmosphere, followed by stifling for dissolving them. Then, 0.3 ml of 3 N potassiumhydroxide aqueous solution was added thereto, followed by stirring at room temperature. Upon completion of the reaction, the reaction mixture was concentrated under reduced pressure. Then, isopropylalcohol was added thereto, and the produced solid was filtered to give the target compound.

$^1$H NMR (400 MHz, D$_2$O): δ 7.10 (4H, m), 6.98 (2H, d), 6.57 (4H, d), 6.38 (2H, s), 4.55 (2H, s), 3.82 (1H, d), 3.07 (2H, s), 2.59 (4H, s), 2.36 (2H, s), 2.13 (4H, s), 1.51 (3H, s).

Example 25: Preparation of (S)-3-(4-(4-((6-methoxy-3,4-dihydroisoquinoline-2(1H)-yl)methyl)benzyloxy)phenyl)hex-4-ynoic acid

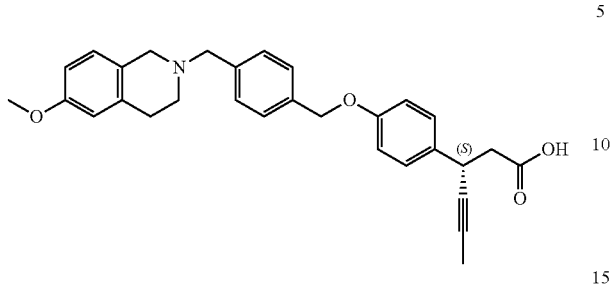

The target compound was obtained by the same manner as described in Example 21 except that 6-methoxy-1,2,3,4-tetrahydroisoquinoline was used instead of 1,2,3,4-tetrahydroisoquinoline.

$^1$H NMR (400 MHz, DMSO): δ 7.40 (4H, q), 7.26 (2H, d), 6.94 (3H, m), 6.68 (2H, m), 5.06 (2H, s), 3.95 (1H, t), 3.70 (3H, s), 3.51 (2H, s), 3.43 (2H, s), 2.77 (2H, t), 2.66 (2H, t), 2.57 (2H, d), 1.75 (3H, d).

Example 26: Preparation of (S)-3-(4-(4-((4-phenylpiperidine-1-yl)methyl)benzyloxy)phenyl)hex-4-ynoic acid

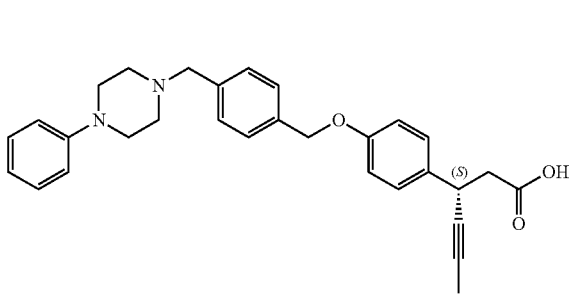

The target compound was obtained by the same manner as described in Example 21 except that 4-phenylpiperidine was used instead of 1,2,3,4-tetrahydroisoquinoline.

$^1$H NMR (400 MHz, CDCl$_3$): δ 7.66 (2H, d), 7.49 (2H, d), 7.30 (7H, m), 6.87 (2H, d), 5.04 (2H, s), 4.19 (2H, s), 4.06 (1H, t), 3.59 (2H, d), 2.73 (7H, m), 2.00 (2H, d), 1.82 (3H, s).

Example 27: Preparation of (S)-3-(4-(4-(isoindoline-2-ylmethyl)benzyloxy)phenyl)hex-4-ynoic acid

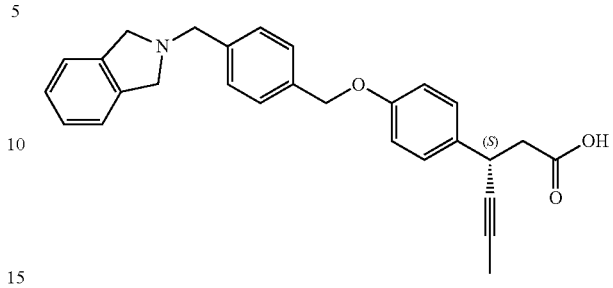

The target compound was obtained by the same manner as described in Example 21 except that isoindoline was used instead of 1,2,3,4-tetrahydroisoquinoline.

$^1$H NMR (400 MHz, CDCl$_3$): δ 7.68 (2H, d), 7.47 (2H, d), 7.38 (2H, m), 7.30 (4H, m), 6.87 (2H, d), 5.06 (2H, s), 4.90 (2H, s), 4.32 (4H, m), 4.05 (1H, t), 2.81 (2H, m), 1.83 (3H, s).

Example 28: Preparation of (S)-3-(4-(4-((4-phenyl-5,6-dihydropyridine-1(2H)-yl)methyl)benzyloxy)phenyl)hex-4-ynoic acid

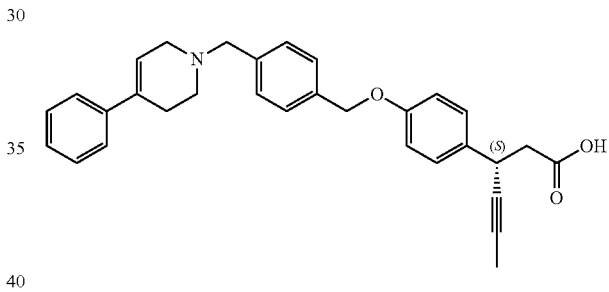

The target compound was obtained by the same manner as described in Example 21 except that 4-phenyl-1,2,3,6-tetrahydropyridine hydrochloride was used instead of 1,2,3,4-tetrahydroisoquinoline.

$^1$H NMR (400 MHz, CDCl$_3$): δ 7.47 (2H, d), 7.36 (9H, m), 6.88 (2H, d), 5.99 (1H, s), 4.99 (2H, s), 4.18 (1H, m), 4.06 (2H, m), 3.53 (2H, s), 3.22 (2H, s), 2.82 (4H, m), 1.82 (3H, s).

Example 29: Preparation of (S)-3-(4-(4-((4-(4-(methoxymethoxy)phenyl)piperazine-1-yl)methyl)benzyloxy)phenyl)hex-4-ynoic acid

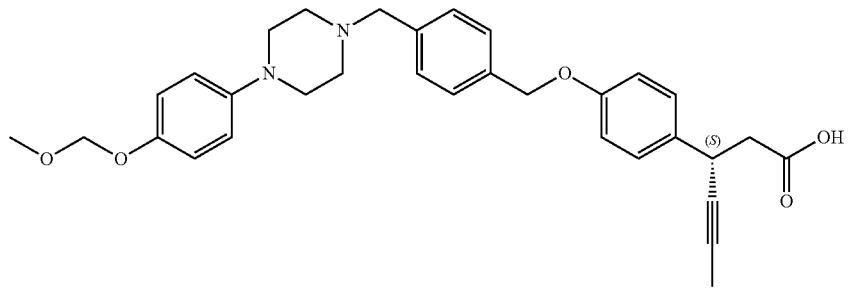

The target compound was obtained by the same manner as described in Example 21 except that 1-(4-(methoxymethoxy)phenyl)piperazine was used instead of 1,2,3,4-tetrahydroisoquinoline.

$^1$H NMR (400 MHz, CDCl$_3$): δ 7.57 (2H, d), 7.46 (2H, d), 7.26 (2H, d), 6.97 (2H, d), 6.87 (2H, d), 6.80 (2H, d), 5.13 (2H, s), 5.01 (2H, s), 4.13 (2H, s), 4.02 (1H, t), 3.51 (11H, m), 2.72 (2H, m), 1.79 (3H, s).

Example 30: Preparation of (S)-3-(4-(4-((4-(5-isopropyl-1,2,4-oxadiazole-3-yl)piperidine-1-yl)methyl)benzyloxy)phenyl)hex-4-ynoic acid

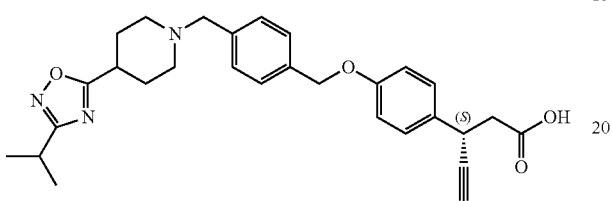

The target compound was obtained by the same manner as described in Example 21 except that 3-isopropyl-5-(piperidine-4-yl)-1,2,4-oxadiazole was used instead of 1,2,3,4-tetrahydroisoquinoline.

$^1$H NMR (400 MHz, CDCl$_3$): δ 7.63 (2H, d), 7.46 (2H, d), 7.30 (2H, d), 6.86 (2H, d), 5.05 (2H, d), 4.13 (2H, m), 4.03 (1H, t), 3.61 (1H, s), 3.43 (2H, s), 3.10 (1H, m), 2.92 (4H, m), 2.73 (2H, m), 2.30 (2H, m), 1.83 (3H, s), 1.32 (6H, d).

Example 31: Preparation of (S)-3-(4-(4-((4-(5-isopropyl-1,2,4-oxadiazole-3-yl)piperazine-1-yl)methyl)benzyloxy)phenyl)hex-4-ynoic acid

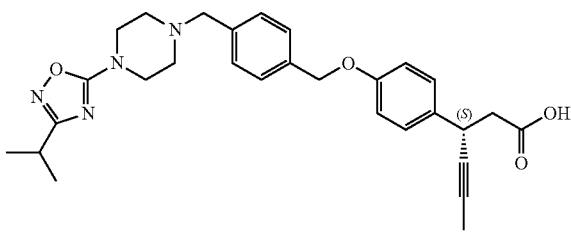

The target compound was obtained by the same manner as described in Example 21 except that 3-isopropyl-5-(piperazine-1-yl)-1,2,4-oxadiazole was used instead of 1,2,3,4-tetrahydroisoquinoline.

$^1$H NMR (400 MHz, CDCl$_3$): δ 7.61 (2H, d), 7.49 (2H, d), 7.30 (2H, d), 6.87 (2H, d), 5.05 (2H, s), 4.15 (4H, m), 4.02 (1H, t), 3.49 (3H, m), 2.81 (3H, m), 1.83 (3H, s), 1.24 (6H, d).

Example 32: Preparation of (S)-3-(4-(4-((4-(4-(methylsulfonyl)phenyl)-5,6-dihydropyridine-1(2H)-yl)methyl)benzyloxy)phenyl)hex-4-ynoic acid

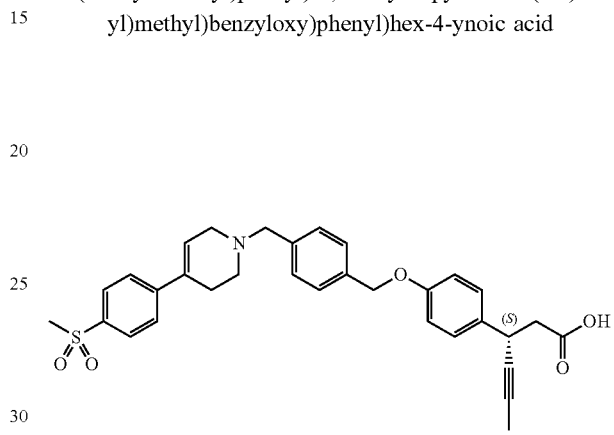

The target compound was obtained by the same manner as described in Example 21 except that 4-(4-(methylsulfonyl)phenyl)-1,2,3,6-tetrahydropyridine hydrochloride obtained in Manufacturing Example 9 was used instead of 1,2,3,4-tetrahydroisoquinoline.

$^1$H NMR (400 MHz, DMSO): δ 7.95 (2H, d), 7.75 (2H, d), 7.63 (2H, d), 7.44 (2H, d), 7.30 (2H, d), 6.98 (2H, d), 6.37 (1H, s), 5.14 (2H, s), 4.45 (2H, t), 6.97 (1H, s), 6.82 (4H, m), 3.27 (4H, s), 2.84 (2H, s), 2.59 (2H, d), 1.77 (3H, s).

Example 33: Preparation of (S)-3-(4-(4-((4-(4-(3-(methylsulfonyl)propoxy)phenyl)-5,6-dihydropyridine-1(2H)-yl)methyl)benzyloxy)phenyl)hex-4-ynoic acid

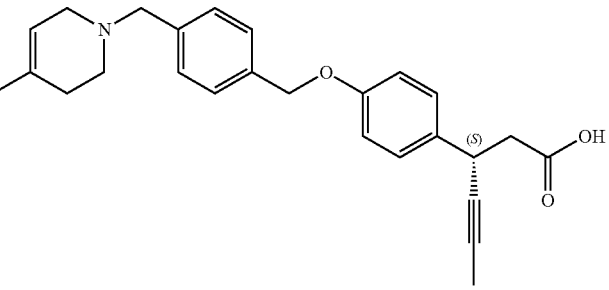

The target compound was obtained by the same manner as described in Example 21 except that 4-(4-(3-(methylsulfonyl)propoxy)phenyl)-1,2,3,6-tetrahydropyridine hydrochloride obtained in Manufacturing Example 11 was used instead of 1,2,3,4-tetrahydroisoquinoline.

¹H NMR (400 MHz, CDCl₃): δ 7.66 (2H, d), 7.49 (2H, d), 7.32 (2H, d), 7.15 (2H, d), 6.90 (2H, d), 6.82 (2H, d), 5.06 (2H, s), 4.18 (2H, s), 4.09 (3H, m), 3.58 (2H, s), 3.26 (2H, m), 2.97 (3H, s), 2.81 (5H, m), 2.62 (3H, s), 2.32 (2H, m), 1.96 (2H, d), 1.83 (3H, s).

Example 34: Preparation of (3S)-3-(4-(4-(1-(3,4-dihydroisoquinoline-2(1H)-yl)ethyl)benzyloxy)phenyl)hex-4-ynoic acid

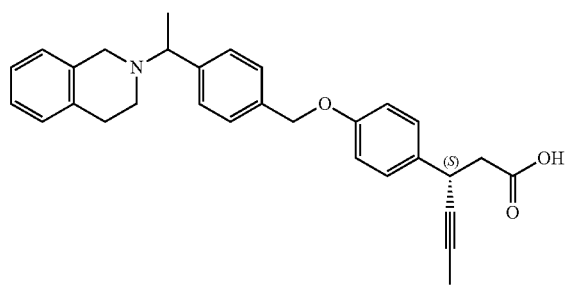

The target compound was obtained by the same manner as described in Example 21 except that (3S)-ethyl 3-(4-(4-(1-bromoethyl)benzyloxy)phenyl)hex-4-inoate obtained in Manufacturing Example 12 was used instead of (S)-ethyl 3-(4-(4-((methylsulfonyloxy)methyl)benzyloxy)phenyl)hex-4-inoate.

¹H NMR (400 MHz, CDCl₃): δ 12.98 (1H, s), 7.61 (6H, m), 7.30 (4H, m), 6.92 (2H, t), 5.08 (2H, s), 4.29 (2H, s), 4.06 (1H, s), 3.81 (1H, s), 3.51 (2H, s), 3.21 (2H, m), 2.75 (2H, m), 1.95 (2H, d), 1.84 (3H, s).

Example 35: Preparation of (S)-3-(4-(4-((4-(4-hydroxyphenyl)piperazine-1-yl)methyl)benzyloxy)phenyl)hex-4-ynoic acid

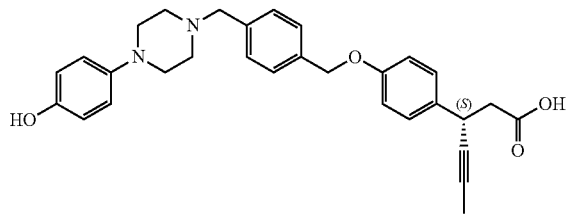

The target compound was obtained by the same manner as described in Example 21 except that 4-(1,2,3,6-tetrahydropyridine-4-yl)phenol hydrochloride obtained in Manufacturing Example 10 was used instead of 1,2,3,4-tetrahydroisoquinoline.

¹H NMR (400 MHz, CDCl₃): δ 8.80 (1H, s), 7.41 (2H, d), 735 (2H, d), 7.28 (2H, d), 6.94 (2H, d), 6.74 (2H, d), 6.63 (2H, d), 5.06 (2H, s), 3.94 (1H, t), 3.62 (3H, s), 2.95 (4H, s), 2.61 (2H, d), 1.77 (3H, s).

Example 36: Preparation of (S)-3-(4-(4-((4-(4-(3-(methylsulfonyl)propoxy)phenyl)piperazine-1-yl)methyl)benzyloxy)phenyl)hex-4-ynoic acid

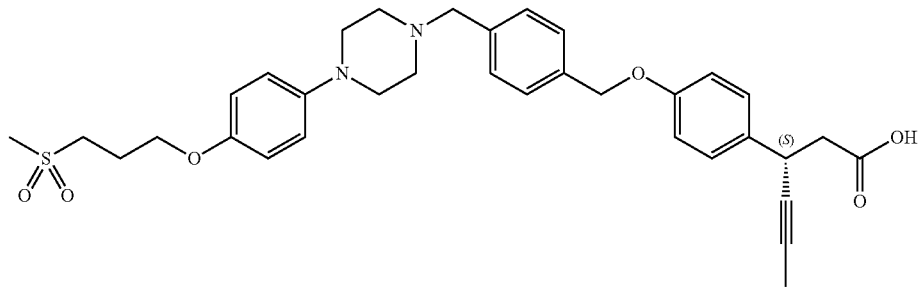

The target compound was obtained by the same manner as described in Example 21 except that 1-(4-(3-(methylsulfonyl)propoxy)phenyl)piperazine hydrochloride was used instead of 1,2,3,4-tetrahydroisoquinoline.

¹H NMR (400 MHz, CDCl₃): δ 12.32 (1H, s), 7.42 (4H, m), 7.29 (2H, d), 6.96 (2H, d), 6.83 (4H, q), 5.06 (2H, s), 4.02 (2H, t), 3.92 (1H, t), 3.52 (2H, s), 3.25 (2H, t), 3.01 (7H, m), 2.61 (2H, d), 2.09 (2H, m), 1.77 (3H, d).

Example 37: Preparation of sodium (S)-3-(4-(4-(isoindoline-2-ylmethyl)benzyloxy)phenyl)hex-4-ynoate

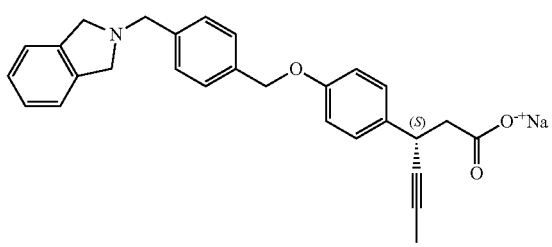

0.4 g of (S)-3-(4-(4-(isoindoline-2-ylmethyl)benzyloxy)phenyl)hex-4-inoic acid prepared in Example 27 and ethanol were loaded in a 500 mL flask in nitrogen atmosphere, followed by stifling for dissolving them. Then, 0.3 ml of 3 N sodium hydroxide aqueous solution was added thereto, followed by stirring at room temperature. Upon completion of the reaction, the reaction mixture was concentrated under reduced pressure, to which isopropyl alcohol was added. Then, the produced solid was filtered to give the target compound.

¹H NMR (400 MHz, CDCl₃): δ 7.09 (2H, d), 7.03 (2H, d), 6.97 (2H, d), 6.85 (2H, m), 6.75 (2H, m), 6.57 (2H, d), 4.54 (2H, s), 3.81 (1H, t), 3.36 (4H, s), 3.31 (2H, s), 2.33 (2H, d), 1.54 (3H, d).

Example 38: Preparation of L-lysine (S)-3-(4-(4-(isoindoline-2-ylmethyl)benzyloxy)phenyl)hex-4-ynoate

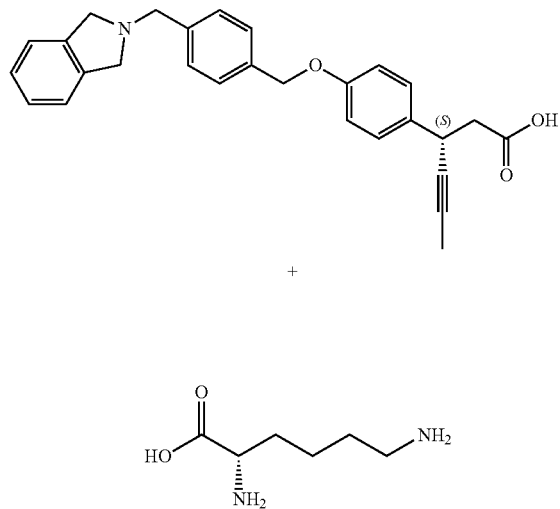

+

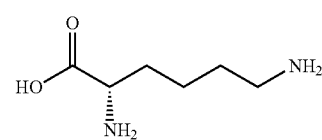

0.4 g of (S)-3-(4-(4-(isoindoline-2-ylmethyl)benzyloxy)phenyl)hex-4-inoic acid prepared in Example 27 and ethanol were loaded in a flask in nitrogen atmosphere, followed by stifling for dissolving them. Then, 0.12 g of L-lysine was added thereto. The reaction temperature was raised to 50° C. and the mixture was stirred for 30 minutes at 50° C. The mixture was cooled down to room temperature, followed by stirring for 30 minutes. Upon completion of the reaction, the produced solid was filtered to give the target compound.

1H NMR (400 MHz, D2O): δ 7.03 (6H, s), 6.83 (2H, s), 6.74 (2H, s), 6.54 (2H, s), 4.53 (2H, s), 3.77 (1H, s), 3.54 (5H, m), 2.88 (2H, t), 2.28 (2H, s), 1.74 (2H, m), 1.62 (3H, m), 1.42 (3H, s), 1.35 (3H, m).

Example 39: Preparation of (S)-3-(4-(4-((4-(4-fluorophenyl)-5,6-dihydropyridine-1(2H)-yl)methyl)benzyloxy)phenyl)hex-4-ynoic acid

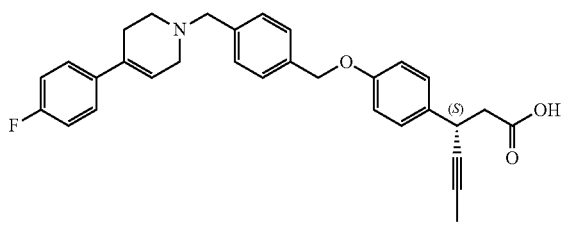

The target compound was obtained by the same manner as described in Example 21 except that -(4-fluorophenyl)-1,2,3,6-tetrahydropyridine hydrochloride was used instead of 1,2,3,4-tetrahydroisoquinoline.

$^1$H NMR (400 MHz, CDCl$_3$): δ 7.69 (2H, d), 7.48 (2H, d), 7.32 (4H, m), 7.04 (2H, t), 6.86 (2H, d), 5.90 (1H, s), 5.03 (2H, s), 4.30 (2H, s), 4.02 (1H, t), 3.71 (2H, s), 3.54 (2H, s), 3.31 (2H, s), 2.73 (2H, m), 1.81 (3H, d).

Example 40: Preparation of (S)-3-(4-(4-((4-(4-methoxyphenyl)piperazine-1-yl)methyl)benzyloxy)phenyl)hex-4-ynoic acid

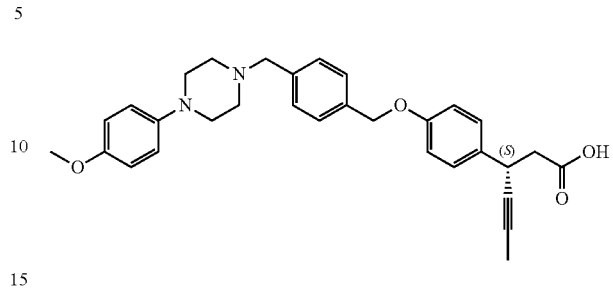

The target compound was obtained by the same manner as described in Example 21 except that 4-(4-methoxyphenyl)-1,2,3,6-tetrahydropyridine was used instead of 1,2,3,4-tetrahydroisoquinoline.

$^1$H NMR (400 MHz, CDCl$_3$): δ 7.64 (2H, d), 7.48 (2H, d), 7.31 (2H, d), 6.94 (2H, s), 6.86 (4H, t), 5.04 (2H, s), 4.21 (2H, s), 4.03 (1H, t), 3.78 (3H, s), 3.60 (2H, s), 3.47 (2H, s), 3.05 (2H, s), 2.73 (2H, m), 1.82 (3H, s).

Example 41: Preparation of sodium (S)-3-(4-(4-((3,4-dihydroquinoline-1(2H)-yl)methyl)benzyloxy)phenyl)hex-4-ynoate

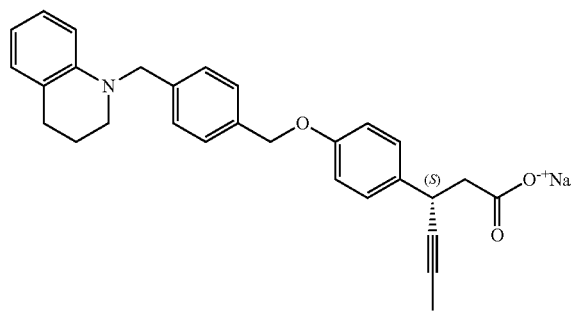

Step 1: Preparation of (S)-3-(4-(4-((3,4-dihydroquinoline-1(2H)-yl)methyl)benzyloxy)phenyl)hex-4-inoic acid The target compound was obtained by the same manner as described in Example 21 except that 1,2,3,4-tetrahydroquinoline was used instead of 1,2,3,4-tetrahydroisoquinoline.

$^1$H NMR (400 MHz, CDCl$_3$): δ 7.02 (2H, d), 6.76 (2H, d), 6.69 (2H, d), 6.43 (4H, m), 6.21 (1H, s), 6.02 (1H, s), 4.24 (2H, s), 3.84 (3H, s), 2.68 (2H, s), 2.37 (2H, d), 2.14 (2H, s), 1.47 (3H, s), 1.35 (2H, s).

Step 2: Preparation of sodium (S)-3-(4-(4-((3,4-dihydroquinoline-1(2H)-yl)methyl)benzyloxy)phenyl)hex-4-inoate The target compound was obtained by the same manner as described in Example 37 except that (S)-3-(4-(4-((3,4-dihydroquinoline-1(2H)-yl)methyl)benzyloxy)phenyl)hex-4-inoic acid obtained in step 1) was used instead of (S)-3-(4-(4-(isoindoline-2-ylmethyl)benzyloxy)phenyl)hex-4-inoic acid.

¹H NMR (400 MHz, D₂O): δ 7.01 (2H, d), 6.74 (2H, d), 6.68 (2H, d), 6.42 (4H, m), 6.15 (1H, s), 6.02 (1H, s), 4.25 (2H, s), 3.79 (3H, s), 2.62 (2H, s), 2.34 (2H, d), 2.12 (2H, s), 1.45 (3H, s), 1.32 (2H, s).

Example 42: Preparation of potassium (S)-3-(4-(4-((3,4-dihydroquinoline-1(2H)-yl)methyl)benzyloxy)phenyl)hex-4-ynoate

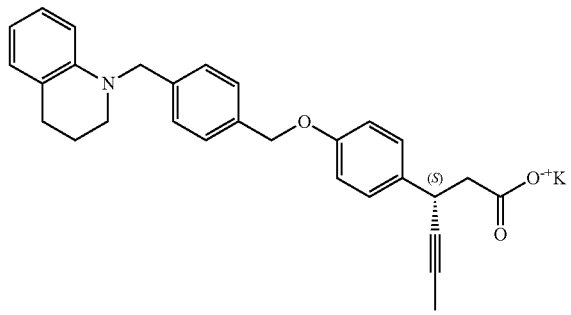

The target compound was obtained by the same manner as described in Example 25 except that (S)-3-(4-(4-((3,4-dihydroquinoline-1(2H)-yl)methyl)benzyloxy)phenyl)hex-4-inoic acid obtained in step 1) of Example 41 was used instead of (S)-3-(4-(4-((4-(4-fluorophenyl)piperazine-1-yl)methyl)benzyloxy)phenyl)hex-4-inoic acid.

¹H NMR (400 MHz, D₂O): δ 6.97 (2H, d), 6.71 (2H, d), 6.63 (2H, d), 6.45 (2H.$), 6.38 (2H, d), 6.13 (1H, s), 5.98 (1H, s), 4.20 (2H, s), 3.71 (3H, m), 2.58 (2H, s), 2.32 (2H, s), 2.15 (2H, s), 1.43 (3H, s), 1.29 (2H, s).

Example 43: Preparation of (S)-3-(4-(4-((4-(benzo[d]thiazole-2-yl)piperazine-1-yl)methyl)benzyloxy)phenyl)hex-4-ynoic acid

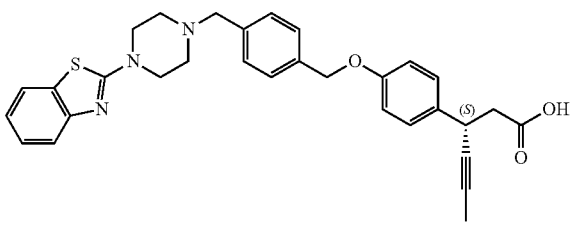

The target compound was obtained by the same manner as described in Example 21 except that 2-(piperazine-1-yl)benzo[d]thiazole hydrochloride obtained in Manufacturing Example 13 was used instead of 1,2,3,4-tetrahydroisoquinoline.

¹H NMR (400 MHz, DMSO): δ 10.87 (1H, s), 7.85 (1H, d), 7.55 (5H, m), 7.31 (3H, m), 7.14 (2H, t), 6.96 (2H, d), 5.13 (2H, s), 4.40 (2H, s), 4.17 (2H, s), 3.95 (1H, t), 3.57 (3H, t), 3.22 (3H, s), 2.57 (2H, d), 1.78 (3H, d).

Example 44: Preparation of (S)-3-(4-(4-((4-(5-propylpyrimidine-2-yl)piperazine-1-yl)methyl)benzyloxy)phenyl)hex-4-ynoic acid

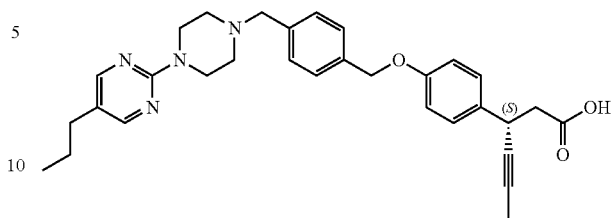

The target compound was obtained by the same manner as described in Example 21 except that 2-(piperazine-1-yl)-5-propylpyrimidine hydrochloride obtained in Manufacturing Example 14 was used instead of 1,2,3,4-tetrahydroisoquinoline.

¹H NMR (400 MHz, CDCl₃): δ 8.20 (2H, s), 7.62 (2H, d), 7.47 (2H, d), 7.30 (2H, d), 6.85 (2H, d), 5.08 (2H, s), 4.80 (2H, d), 4.17 (2H, s), 4.03 (1H, t), 3.84 (1H, t), 3.43 (2H, s), 2.74 (4H, m), 2.43 (2H, t), 1.83 (3H, d), 1.59 (2H, q), 0.94 (3H, t).

Example 45: Preparation of (S)-3-(4-(4-((4-(5-cyanopyridine-2-yl)piperazine-1-yl)methyl)benzyloxy)phenyl)hex-4-ynoic acid

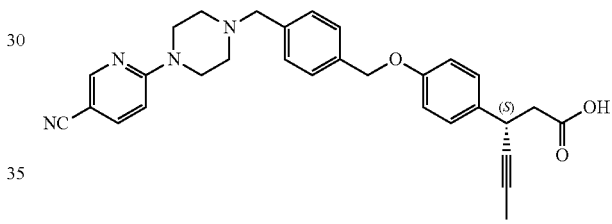

The target compound was obtained by the same manner as described in Example 21 except that 6-(piperazine-1-yl)nicotinonitrile hydrochloride obtained in Manufacturing Example 15 was used instead of 1,2,3,4-tetrahydroisoquinoline.

¹H NMR (400 MHz, DMSO): δ 11.20 (1H, s), 8.56 (1H, s), 7.99 (1H, d), 7.63 (1H, d), 7.55 (1H, d), 7.27 (2H, d), 7.04 (1H, d), 6.95 (2H, d), 5.12 (2H, s), 4.57 (2H, d), 4.35 (2H, s), 3.95 (1H, t), 3.39 (5H, m), 2.90 (2H, m), 2.59 (2H, d), 1.77 (3H, d).

Example 46: Preparation of (3S)-3-(4-(4-((3-phenylpyrrolidine-1-yl)methyl)benzyloxy)phenyl)hex-4-ynoic acid

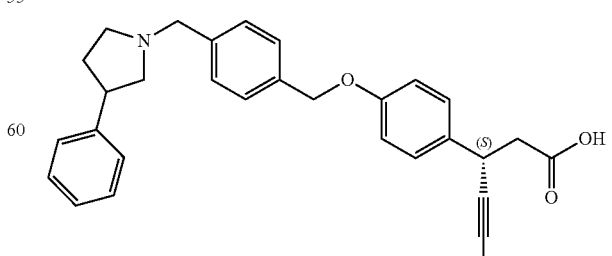

The target compound was obtained by the same manner as described in Example 21 except that 3-phenylpyrrolidine was used instead of 1,2,3,4-tetrahydroisoquinoline.

$^1$H NMR (400 MHz, CDCl$_3$): δ 12.64 (1H, s), 7.66 (2H, s), 7.46 (2H, d), 7.32 (7H, m), 6.86 (2H, d), 5.02 (2H, s), 4.28 (2H, m), 4.04 (1H, t), 3.87 (2H, s), 3.73 (1H, s), 3.18 (1H, s), 2.89 (1H, m), 2.84 (3H, m), 2.61 (1H, s), 2.41 (1H, s), 2.19 (1H, s), 1.81 (3H, d).

Example 47: Preparation of sodium (S)-3-(4-(3-(4-(4-methoxyphenyl)piperazin-1-yl)benzyloxy)phenyl)hex-4-ynoate

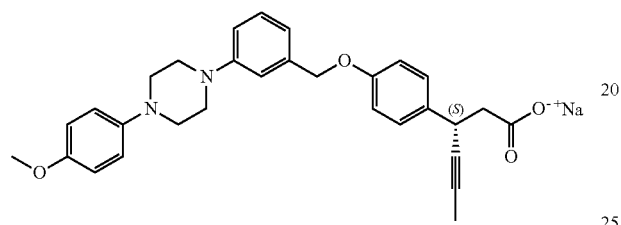

The target compound was obtained by the same manner as described in Example 37 except that (S)-3-(4-(3-(4-(4-methoxyphenyl)piperazine-1-yl)benzyloxy)phenyl)hex-4-ynoic acid was used instead of (S)-3-(4-(4-(isoindoline-2-ylmethyl)benzyloxy)phenyl)hex-4-ynoic acid.

$^1$H NMR (400 MHz, MEOC): δ 7.33 (2H, d), 7.26 (1H, d), 7.11 (1H, s), 6.96 (8H, m), 5.04 (2H, s), 4.04 (1H, t), 3.76 (3H, s), 3.32 (4H, m), 3.21 (4H, m), 2.52 (2H, m), 1.80 (3H, s).

Example 48: Preparation of (S)-3-(4-(4-(2-(6-methoxy-3,4-dihydroisoquinoline-2(1H)-yl)ethyl)benzyloxy)phenyl)hex-4-ynoic acid

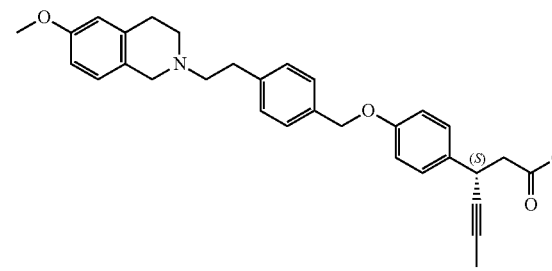

Step 1: Preparation of ethyl (S)-3 (4 (4 (2 (6 methoxy-3,4-dihydroisoquinoline-2(1H)-yl)ethyl)benzyloxy)phenyl)hex-4-inoate 0.5 g of 6-methoxy-1,2,3,4-tetrahydroisoquinoline was loaded in 20 mL of DMF in a flask in nitrogen atmosphere, followed by stifling. 1.1 g of cesiumcarbonate was added thereto at room temperature. 30 minutes later, 1.0 g of (S)-ethyl 3-(4-(4-(2-(methylsulfonyloxy)ethyl)benzyloxy)phenyl)hex-4-inoate prepared in Manufacturing Example 16 was added thereto, followed by stirring at room temperature for 12 hours. Upon completion of the reaction, distilled water was slowly added thereto, followed by extraction using ethylacetate. The extract was washed with brine, dried over anhydrous MgSO$_4$, and concentrated. Then, silica gel column chromatography was performed to give the target compound.

$^1$H NMR (400 MHz, CDCl$_3$): δ 7.35 (2H, d), 7.30 (2H, d), 7.23 (2H, d), 7.00 (1H, d), 6.85 (2H, d), 6.80 (1H, d), 6.70 (1H, d), 5.00 (2H, s), 4.30 (2H, m), 4.13 (2H, m) 4.03 (1H, t), 3.80 (3H, s), 3.58 (6H, m), 3.30 (2H, s), 2.78 (2H, m), 1.86 (3H, d), 1.28 (3H, m).

Step 2: Preparation of (S)-3 (4 (4 (2 (6 methoxy-3,4-dihydroisoquinoline-2(1H)-yl)ethyl)benzyloxy)phenyl)hex-4-inoic acid 0.5 g of ethyl (S)-3-(4-(4-(2-(6-methoxy-3,4-dihydroisoquinoline-2(1H)-yl)ethyl)benzyloxy)phenyl)hex-4-inoate prepared in step 1), THF, methanol, and distilled water were loaded in a flask in nitrogen atmosphere, followed by stifling for dissolving them. Then, 0.5 g of lithium hydroxide was slowly added thereto at room temperature, followed by stifling for at least 1 hour. Upon completion of the reaction, the mixture was acidized (pH: 4~5) by using 1 M HCl aqueous solution, followed by extraction using ethylacetate. The extract was dried under reduced pressure to give the target compound.

$^1$H NMR (400 MHz, CDCl$_3$): δ 7.35 (2H, d), 7.30 (2H, d), 7.23 (2H, d), 7.00 (1H, d), 6.85 (2H, d), 6.80 (1H, d), 6.70 (1H, d), 5.00 (2H, s), 4.30 (2H, m), 4.03 (1H, t), 3.80 (3H, s), 3.58 (6H, m), 3.30 (2H, s), 2.78 (2H, m), 1.86 (3H, d).

Example 49: Preparation of (S)-3-(4-(4-(2-(isoindoline-2-yl)ethyl)benzyloxy)phenyl)hex-4-ynoic acid

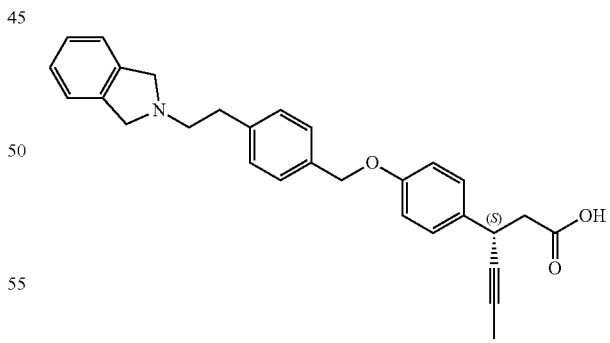

The target compound was obtained by the same manner as described in Example 48 except that isoindoline was used instead of 6-methoxy-1,2,3,4-tetrahydroisoquinoline.

$^1$H NMR (400 MHz, CDCl$_3$): δ 13.57 (1H, s), 7.38 (3H, m), 7.29 (7H, m), 6.90 (2H, d), 5.03 (4H, m), 4.28 (2H, s), 4.08 (1H, t), 3.48 (2H, m), 3.34 (2H, m), 2.80 (2H, m), 1.83 (3H, d).

Example 50: Preparation of (S)-3-(4-(4-(2-(3,4-dihydroisoquinoline-2(1H)-yl)ethyl)benzyloxy)phenyl)hex-4-ynoic acid

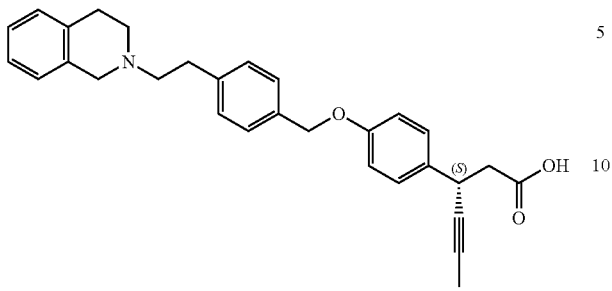

The target compound was obtained by the same manner as described in Example 48 except that 1,2,3,4-tetrahydroisoquinoline was used instead of 6-methoxy-1,2,3,4-tetrahydroisoquinoline.

$^1$H NMR (400 MHz, DMSO): δ 7.44 (2H, d), 7.38 (2H, d), 7.27 (5H, m), 7.22 (1H, d), 6.94 (2H, d), 5.07 (2H, s), 4.64 (1H, d), 4.38 (1H, s), 3.95 (1H, t), 3.77 (1H, s), 3.39 (2H, s), 3.16 (4H, m), 2.26 (2H, d), 1.77 (3H, d), 1.84 (3H, d), 1.29 (3H, t).

Example 51: Preparation of sodium (S)-3-(4-(4-((6-methoxy-3,4-dihydroisoquinoline-2(1H)-yl)methyl)benzyloxy)phenyl)hex-4-ynoate

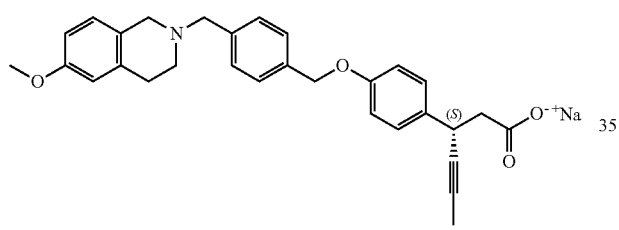

The target compound was obtained by the same manner as described in Example 37 except that (S)-3-(4-(4-((6-methoxy-3,4-dihydroisoquinoline-2(1H)-yl)methyl)benzyloxy)phenyl)hex-4-inoic acid obtained in Example 25 was used instead of (S)-3-(4-(4-(isoindoline-2-ylmethyl)benzyloxy)phenyl)hex-4-inoic acid.

$^1$H NMR (400 MHz, D$_{32}$O): δ 7.10 (2H, d), 7.02 (2H, d), 6.95 (2H, d), 6.55 (2H, d), 6.40 (1H, d), 6.34 (2H, s), 4.53 (2H, s), 3.83 (1H, t), 3.39 (3H, s), 3.17 (2H, s), 3.05 (2H, s), 2.37 (4H, m), 2.20 (2H, s), 1.57 (3H, s).

Comparative Example 1: Preparation of [(3S)-6-({(2',6'-dimethyl-4'-[3-(methanesulfonyl)propoxy]-[1,1'-biphenyl]-3-yl)}methoxy)-2,3-dihydro-1-benzofuran-3-yl]acetic acid

[(3S)-6-({(2',6'-dimethyl-4'-[3-(methanesulfonyl)propoxy]-[1,1'-biphenyl]-3-yl)}methoxy)-2,3-dihydro-1-benzofuran-3-yl]acetic acid was prepared by the method informed in international patent publication No. 2008/001931.

Comparative Example 2: Preparation of (3S)-3-(4-{[4-(1'H-spiro[indene-1,4'-piperidine]-1'-ylmethyl)benzyl]oxy}phenyl)hex-4-inoic acid

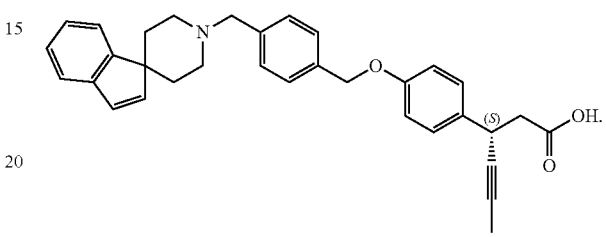

(3S)-3-(4-{[4-(1'H-spiro[indene-1,4'-piperidine]-1'-ylmethyl)benzyl]oxy}phenyl)hex-4-inoic acid was prepared by the method informed in international patent publication No. WO2011/046851.

Comparative Example 3: Preparation of 4-(3-phenoxybenzylamino)phenylpropionic acid

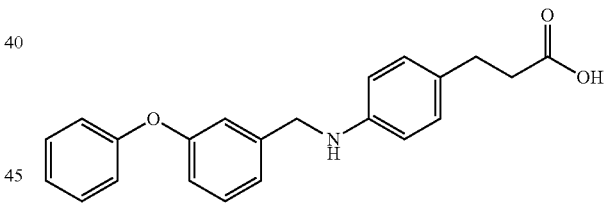

4-(3-phenoxybenzylamino)phenylpropionic acid was prepared by the conventional method.

The chemical formulas of the compounds prepared in Examples 1~51 are summarized in Table 1.

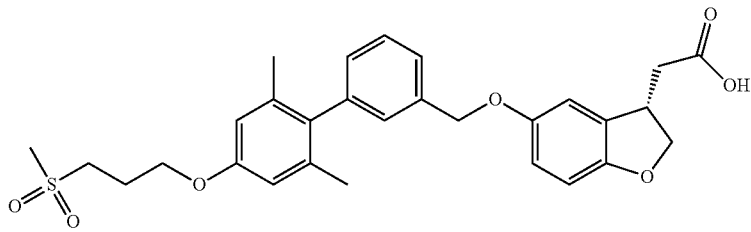 [SMILES: Cc1cc(OCCCS(C)(=O)=O)cc(C)c1-c1cccc(COc2ccc3c(c2)[C@H](CC(=O)O)CO3)c1]

TABLE 1

| Example | Formula |
|---|---|
| 1 | (structure: 1,4-dioxaspiro[4.5]dec-7-ene linked to phenyl-CH₂-O-phenyl-CH(C≡C-CH₃)-CH₂-COOH) |
| 2 | (structure as above with alkyne isomer) + L-lysine (HO₂C-CH(NH₂)-(CH₂)₄-NH₂) |
| 3 | (para-substituted analog: 1,4-dioxaspiro[4.5]dec-7-ene-phenyl-CH₂-O-phenyl-CH(C≡C-CH₃)-CH₂-COOH) |
| 4 | (cyclohexenone-phenyl-CH₂-O-phenyl-CH(C≡C-CH₃)-CH₂-COOH) |

TABLE 1-continued

| Example | Formula |
|---------|---------|
| 5 | |
| 6 | |
| 7 | |
| 8 | |
| 9 | |

TABLE 1-continued

| Example | Formula |
|---------|---------|
| 10 | |
| 11 | |
| 12 | |
| 13 | |
| 14 | |

TABLE 1-continued

| Example | Formula |
|---|---|
| 15 | |
| 16 | |
| 17 | |
| 18 | |
| 19 | |

TABLE 1-continued
| Example | Formula |
|---|---|
| 20 | 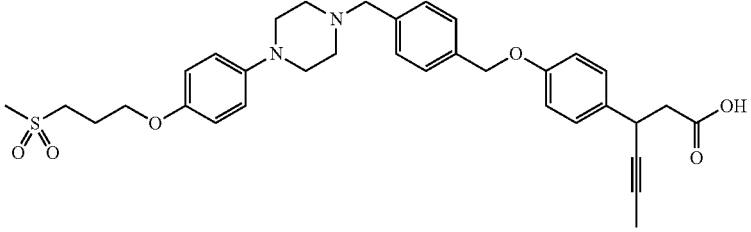 [SMILES: CC#CC(CC(=O)O)c1ccc(OCc2ccc(CN3CCN(c4ccc(OCCCS(C)(=O)=O)cc4)CC3)cc2)cc1] |
| 21 | 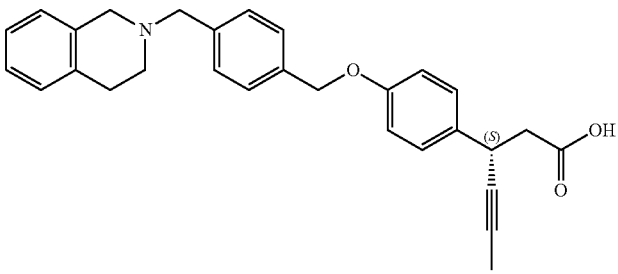 |
| 22 | 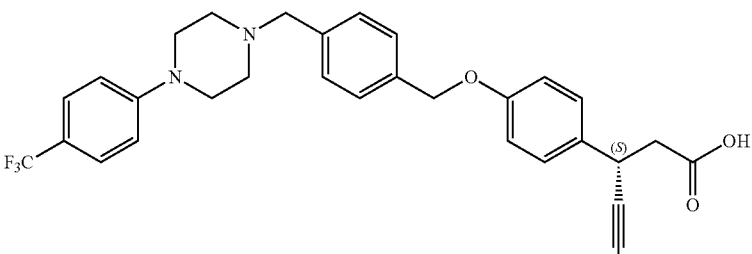 |
| 23 | 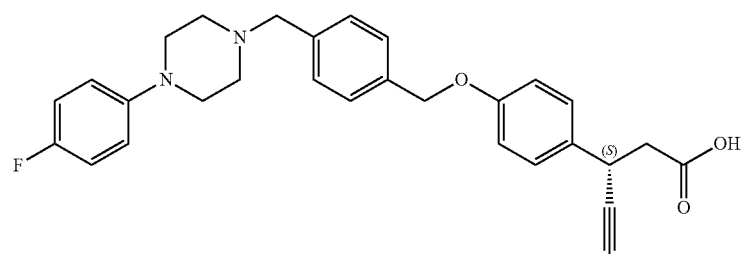 |
| 24 | 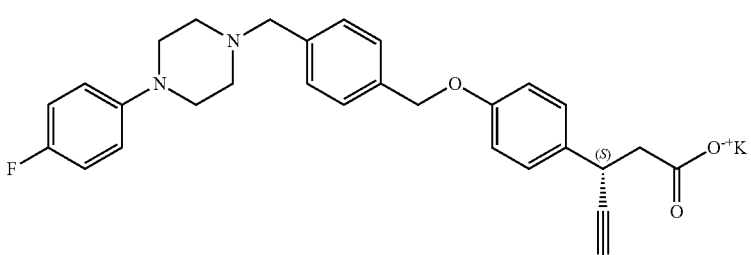 |

TABLE 1-continued

| Example | Formula |
|---|---|
| 25 | |
| 26 | |
| 27 | |
| 28 | |
| 29 | |

TABLE 1-continued
| Example | Formula |
|---|---|
| 30 | 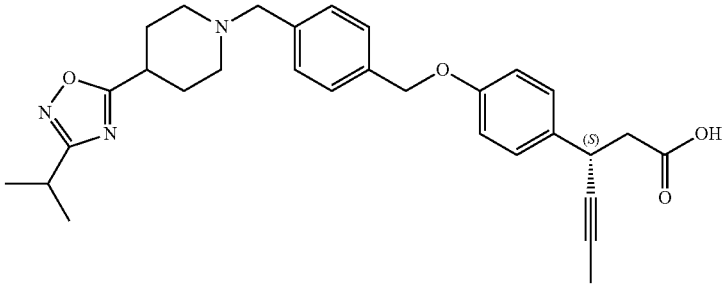 |
| 31 | 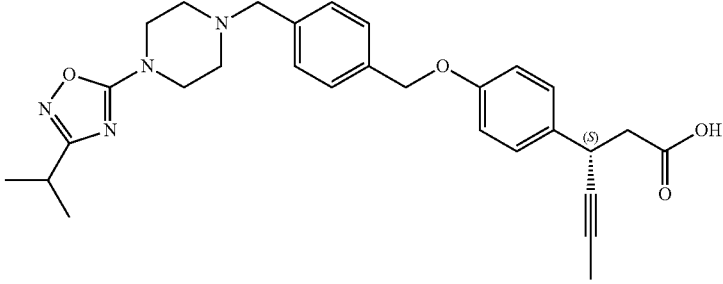 |
| 32 | 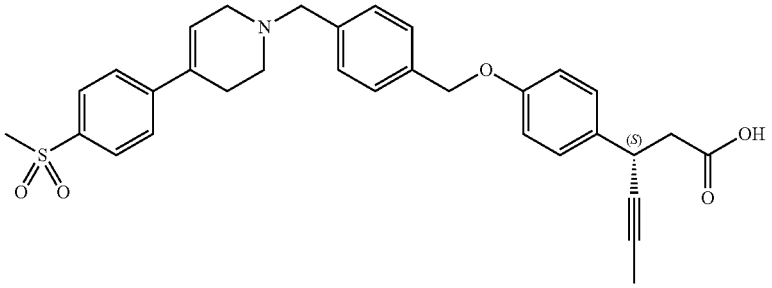 |
| 33 | 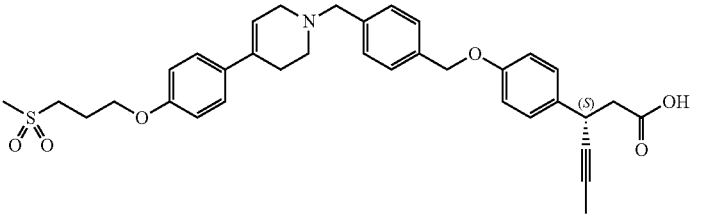 |
| 34 | 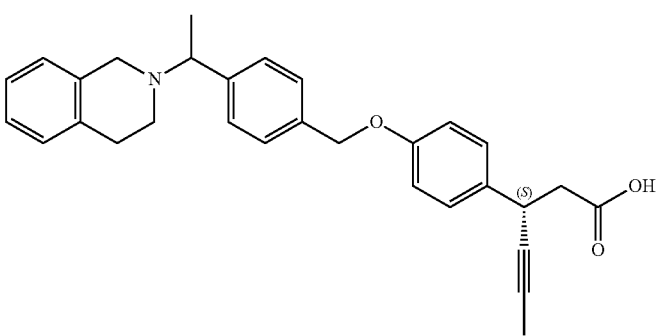 |

TABLE 1-continued
| Example | Formula |
|---|---|
| 35 | 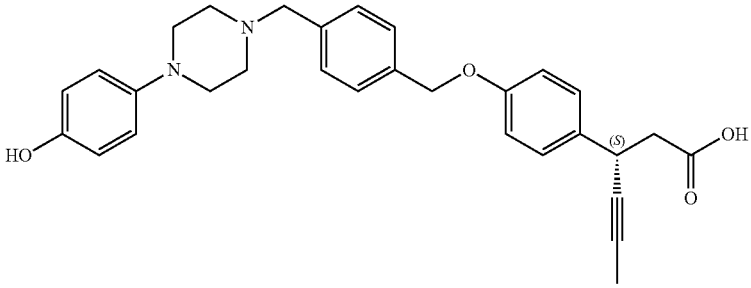 |
| 36 | 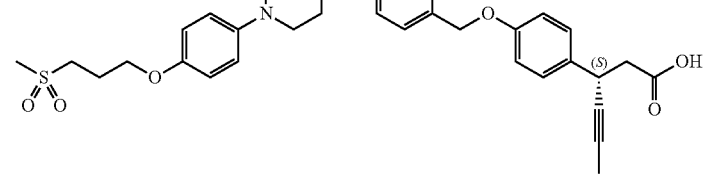 |
| 37 | 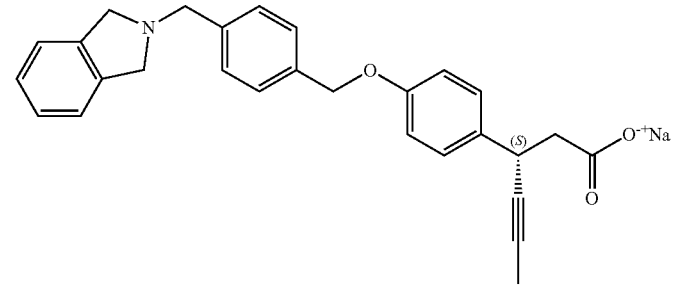 |
| 38 | 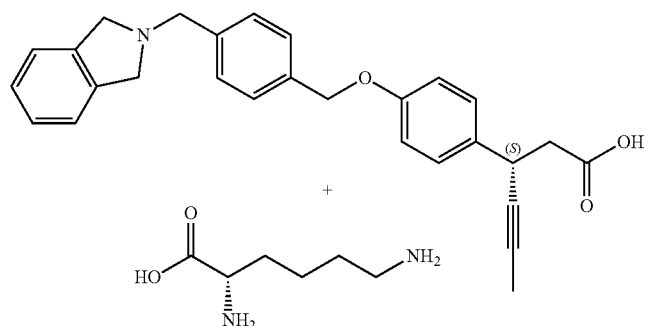 |
| 39 | 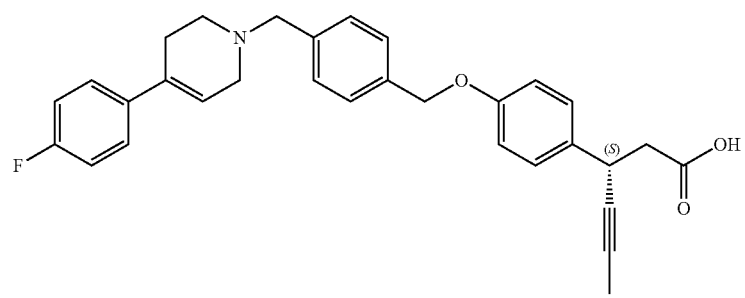 |

TABLE 1-continued
| Example | Formula |
|---|---|
| 40 | 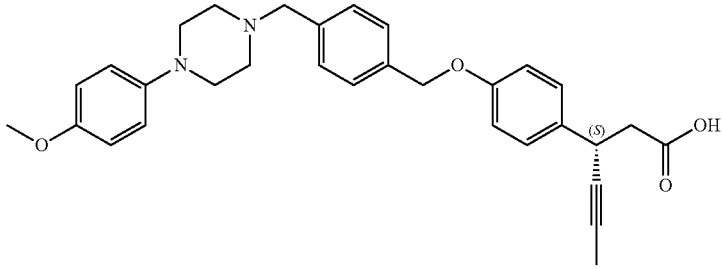 |
| 41 | 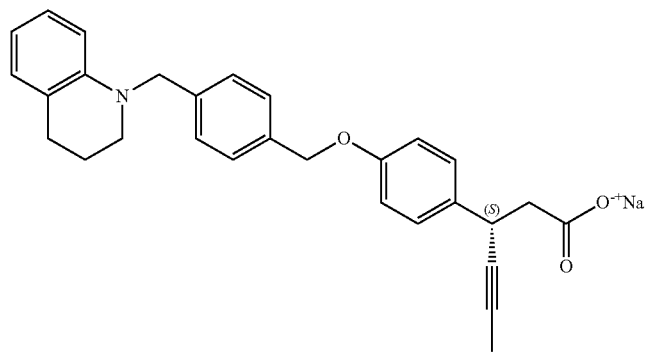 |
| 42 | 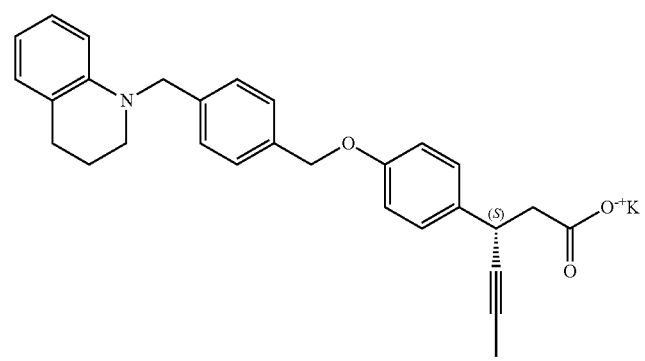 |
| 43 | 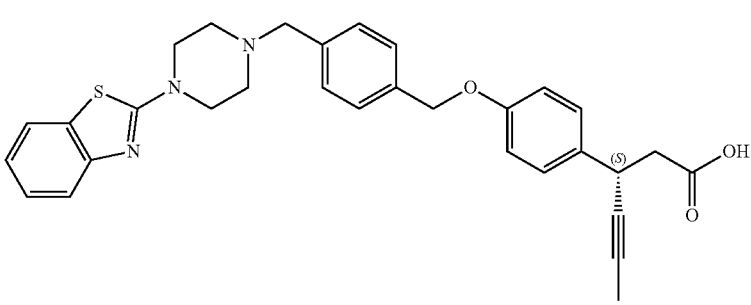 |
| 44 | 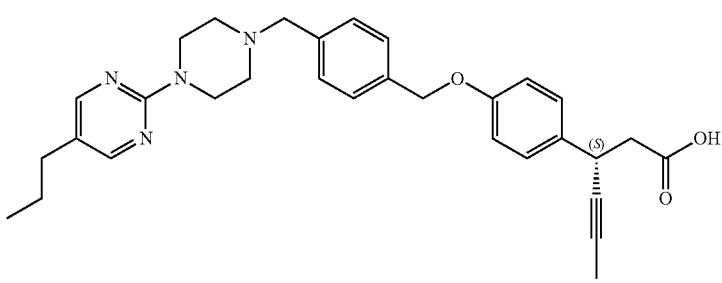 |

TABLE 1-continued
| Example | Formula |
|---|---|
| 45 | 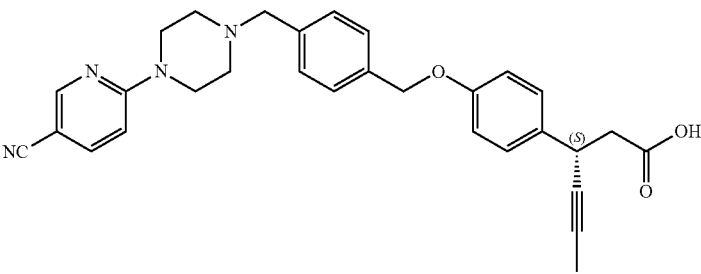 |
| 46 | 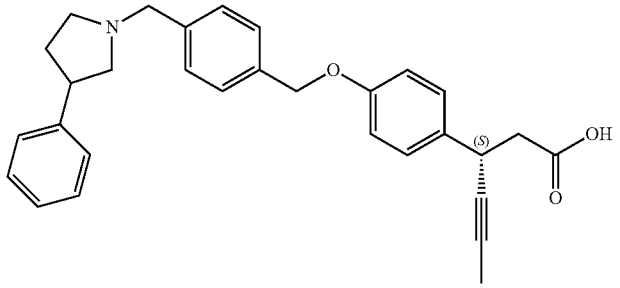 |
| 47 | 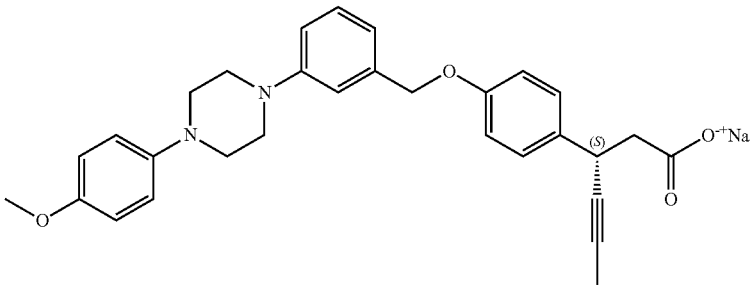 |
| 48 | 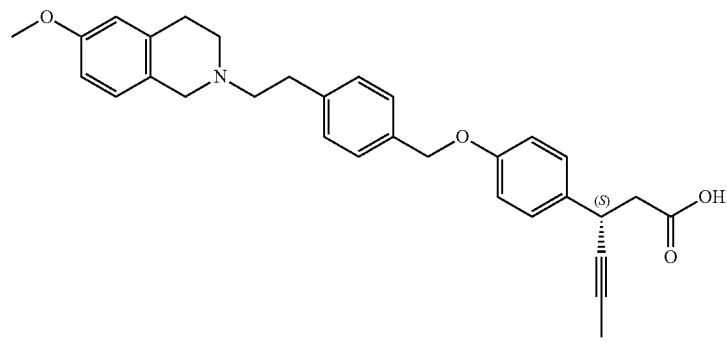 |
| 49 | 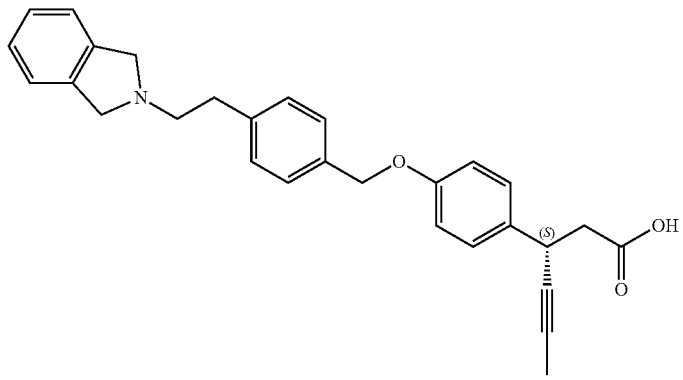 |

TABLE 1-continued

| Example | Formula |
|---|---|
| 50 | (tetrahydroisoquinoline)-N-CH₂CH₂-(4-phenyl)-CH₂-O-(4-phenyl)-(S)-CH(C≡C-CH₃)-CH₂-C(=O)-OH |
| 51 | (6-methoxy-tetrahydroisoquinoline)-N-CH₂-(4-phenyl)-CH₂-O-(4-phenyl)-(S)-CH(C≡C-CH₃)-CH₂-C(=O)-O⁻⁺Na |

Experimental Example 1: Evaluation of GPR40 protein activity according to 3-(4-(benzyloxy)phenyl)hex-4-inoic acid derivative To evaluate the GPR40 activity according to the novel 3-(4-(benzyloxy)phenyl)hex-4-inoic acid derivative of the present invention, the following experiment was performed.

The GPR40 protein activity according to the novel 3-(4-(benzyloxy)phenyl)hex-4-inoic acid derivative of the present invention was measured by investigating the changes in intracellular calcium concentration affected by the GRP40 activation. First, HEK-293 cells were transfected with human GPR40 DNA (Origene, RC218370) by using Fugene HD (Promega, E2311). The transfected HEK-293 cells were distributed in a 96-well black clear bottom floor plate (Costar, 3603), followed by culture. 24 hours later, the cell culture medium was replaced with Dulbecco's Modified Eagle Medium (DMEM, 50 µl/well) supplemented with 1% fetal bovine serum (FBS). To measure the calcium concentration, 50 µl of Fluo-4 reagent (Invitrogen, F10471) was added to each well, followed by culture in a 37° C. incubator for 2 hours. During the culture, the compounds of Examples and the compounds of Comparative Examples 1 and 2 were diluted with 1×HBSS (Hank's Buffered Salt Solution) containing 20 mM 4-(2-hydroxyethyl)-1-piperazineethanesulfonic acid (HEPES) buffer, resulting in the preparation of the samples for treating the cells. 2 hours after the culture began, those prepared samples were automatically injected to the cells by using Flexstation 3 (Molecular Devices). Then, intracellular calcium concentration was measured for 120 seconds by using SoftMax® Pro software. At this time, dimethylsulfoxide (DMSO) was injected to the cells for the non-treated group, followed by measuring the calcium concentration therein. The GPR40 protein activity was calculated by the below mathematical formula 1 with the results of calcium concentration measurement. The results are shown in Table 2.

GPR40 activity=(intracellular calcium concentration increased by the sample)/(intracellular calcium concentration of the non-treated group)×100  [Mathematical Formula 1]

TABLE 2

| Example | $EC_{50}$ (µM) |
|---|---|
| 1 | C |
| 2 | C |
| 3 | C |
| 4 | C |
| 5 | B |
| 6 | B |
| 7 | A |
| 8 | C |
| 9 | A |
| 10 | C |
| 11 | A |
| 12 | A |
| 13 | C |
| 14 | A |
| 15 | C |
| 16 | C |
| 17 | C |
| 18 | C |
| 19 | C |
| 20 | C |
| 21 | B |
| 22 | C |
| 23 | B |
| 24 | B |
| 25 | C |
| 26 | C |
| 27 | A |
| 28 | A |
| 29 | B |
| 30 | C |
| 31 | C |
| 32 | C |
| 33 | C |
| 34 | C |

TABLE 2-continued

| Example | EC$_{50}$ (μM) |
|---|---|
| 35 | C |
| 36 | C |
| 37 | A |
| 38 | A |
| 39 | B |
| 40 | B |
| 41 | C |
| 42 | C |
| 43 | C |
| 44 | C |
| 45 | C |
| 46 | C |
| 47 | B |
| 48 | C |
| 49 | C |
| 50 | C |
| 51 | C |
| Comparative Example 1 | B |
| Comparative Example 2 | C |

In Table 2,
A: under 0.20 μM;
B: 0.20-0.30 μM; and
C: over 0.30 μM.

As shown in Table 2, the compounds of Examples of the present invention were confirmed to be excellent in promoting the activation of GPR 40 protein at a low concentration. In particular, the compounds of Examples 7, 9, 11, 12, 14, 27, 28, 37, and 38 were able to promote the activation of GPR40 protein by 50% at a very low concentration (under 0.20 μM), suggesting that their capability to increase the intracellular Ca$^{2+}$ concentration was excellent, compared with that of the compound of Comparative Example 1 (B, 0.28 μM).

Therefore, it was confirmed that the novel 3-(4-(benzyloxy)phenyl)hex-4-inoic acid derivative of the present invention is excellent in increasing the activation of GPR40 protein. This activity is at least similar or better than that of the conventional anti-diabetic agent (Comparative Example 1) known to promote insulin secretion by inducing the activation of GPR40 protein. Thus, the composition comprising the compound of the invention as an active ingredient can be efficiently used as a pharmaceutical composition for the prevention and treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

Experimental Example 2: Analysis of Calcium Flux

Calcium flux according to the activation of GPR40 by the novel 3-(4-(benzyloxy)phenyl)hex-4-inoic acid derivative of the present invention was evaluated by Millipore, the GPCR assay specialized institution.

The compounds of Examples of the invention dissolved in DMSO (dimethyl sulfoxide), PBS (phosphate buffered saline), and DW (distilled water), etc, were diluted three-times with EMD Millipore's GPCR profiler assay buffer. Likewise, the non-treated group (vehicle) and the positive control groups (Comparative Examples 1 and 3) were prepared to increase the accuracy of the analysis. Each well was filled with EMD Millipore's GPCR profiler assay buffer. The said EMD Millipore's GPCR profiler assay buffer was HBSS (Hanks Balanced Salt Solution) containing 20 mM HEPES (4-(2-hydroxyethyl)-1-piperazineethanesulfonic acid) and 2.5 mM Probenecid (4-(dipropylsulfamoyl)benzoic acid), whose pH was regulated as 7.4.

The compounds of Examples were duplicated at each concentration. The positive control group (Comparative Example 1 or 3) for each G protein-coupled receptor (GPCR) was prepared as the non-treated group (vehicle) was prepared. The positive control group (Comparative Example 1 or 3) for each GPCR was included in E$_{max}$ at such concentration that displayed the highest activity. Agonist assay was performed by using FLIPR$^{TETRA}$. Fluorescence and luminescence baseline were measured. The compounds of Examples, the non-treated group (vehicle), and the positive control group (Comparative Example 1 or 3) were included in the assay plate. To measure the activity of those compounds of Examples, GPCR activity assay was performed for 180 seconds.

The fluorescence values excluding the baseline were compared with E$_{max}$ of the positive controls (Comparative Examples 1 and 3) and the non-treated group, and the activity was presented as %. The obtained data indicate the inhibition rate (%) resulted from the comparison of EC$_{50}$ with the non-treated group, and the quality of each plate was evaluated by the statistical numbers presenting activity % from repeated data. When the assay data were not satisfactory, an additional experiment was performed.

All the concentration dependent graphs were made by using GraphPad Prism. The graph was modified by Sigmoidal dose response. The minimum value was fixed as 0 and the maximum value was fixed as 100 for the prediction of better effect value.

The results are shown in FIG. 1 and Table 3.

TABLE 3

| Compound | Expected EC$_{50}$ |
|---|---|
| Example 9 | Lower than 1 nM, the lowest detectable conc. |
| Comparative Example 1 | 14 nM |
| Comparative Example 3 | 27 nM |

FIG. 1 is a graph illustrating the activation pattern of GPR40 according to the concentration of the compounds of Example 9, Comparative Example 1, and Comparative Example 3.

As shown in FIG. 1, the compound of Example needed a much lower concentration than the compounds of Comparative Examples 1 and 3 to raise the activity of GPR40 to 50% (even lower than 1 nM, the lowest detectable concentration). Particularly, as shown in Table 3, the compound of Example 9 of the present invention could induce the activation of GPR40 at a lower concentration than the compounds of Comparative Example 1 (14 nM) and Comparative Example 3 (27 nM).

Therefore, it was confirmed that the novel 3-(4-(benzyloxy)phenyl)hex-4-inoic acid derivative of the present invention is excellent in promoting the activation of GPR40 protein, which is particularly more excellent than the conventional anti-diabetic agents (compounds of Comparative Examples 1 and 3) known to increase the insulin secretion by activating GPR40 protein. Thus, the composition comprising the compound of the invention as an active ingredient can be efficiently used as a pharmaceutical composition for the prevention and treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

Experimental Example 3: Analysis of CYP Inhibition

To evaluate the interaction between the novel 3-(4-(benzyloxy)phenyl)hex-4-inoic acid derivative of the present invention and other drugs, the following experiment was performed.

CYP is the enzyme involved in drug metabolism. So, the inhibition of this enzyme can change the prediction of dose of a drug and toxicity caused by the co-treatment with other drugs. Therefore, the inventors measured the inhibitory effect of the compounds of Examples of the invention on endogenous CYP3A4, CYP2C9, CYP1A2, CYP2D6, and CYP2C19. At this time, Invitrogen (P2862) was used as the CYP2D6 inhibition kit, and BD GENTEST (459100, 459300, 459400, 459500) was used as the CYP1A2, CYP2C9, CYP2C19, and CYP3A4 inhibition kit. To prepare the Invitrogen kit, the test sample was diluted in distilled water at 2.5× of the final experimental concentration.

P450 BACULOSOMES® reagent and reproducer (100×) included in Invitrogen kit were diluted in Vivid® CYP450 reaction buffer (2×) at the concentration that matched the target CYP450. The prepared 2.5× sample (80 µL) and the diluted P450 BACULOSOMES® reagent mixture (100 µL) were mixed in each well of U-bottom 96-well plate, followed by pre-culture for 20 minutes. Vivid® CYP450 substrate and NADP+ (100×) were diluted in Vivid® CYP450 reaction buffer (2×) at the concentration that matched the target CYP450 and the substrate. Upon completion of the pre-culture, substrate-NADP (nicotinamide adenine dinucleotide phosphate) mixed solution (20 µL) was added thereto, followed by reaction for 1 hour. Upon completion of the reaction, the reactant was transferred onto the white plate, and then fluorescence was measured with a microplate reader (CYP 2D6 excitation wavelength: 400 nm, absorption wavelength: 502 nm).

The test sample for BD GENTEST kit was diluted in acetonitrile at 50× of the final experimental concentration. NADPH-coenzyme mixture was prepared by diluting the coenzyme, G6PDH, and regulatory protein included in the kit with distilled water at the concentration instructed by the kit. The prepared 50× sample (4 µL) and the NADPH-coenzyme mixture (96 µL) were mixed in each well of U-bottom 96-well plate, followed by pre-culture for 10 minutes in a 37° C. incubator. Enzyme/substrate mixed solution was prepared by diluting the buffer (0.5 M potassium phosphate, pH 7.4), each CYP450 enzyme/substrate mixed solution included in the kit with distilled water at the instructed concentration. Upon completion of the pre-culture, 100 µL of the enzyme/substrate mixed solution was added in each well of the plate, followed by culture in a 37° C. incubator for 15 minutes (CYP 1A2), 30 minutes (CYP 3A4 and CYP 2C19) or 1 and half hours (CYP 2C9). Upon completion of the reaction, the reactant was transferred onto the white plate, and then fluorescence was measured with a microplate reader (CYP 1A2 and CYP 2C19 excitation wavelength: 410 nm, absorption wavelength: 460 nm; CYP 2C9 and CYP 3A4 excitation wavelength: 409 nm, absorption wavelength: 530 nm). The values obtained above were converted into % as the inhibition rate of the sample by the value of the non-treated group. The results are shown in Table 4.

TABLE 4

| Example (10 µM) | CYP inhibition (%) | | | | |
|---|---|---|---|---|---|
| | 1A2 | 2C9 | 2C19 | 2D6 | 3A4 |
| 1 | 0 | 42.8 | 18.3 | 1.9 | 12.7 |
| 3 | 0 | 21.1 | 19.4 | 6.0 | 33.1 |
| 4 | 0 | 41.5 | 45.4 | 19.3 | 35.0 |
| 7 | 4.3 | 47.1 | 3.7 | 13.9 | 15.5 |
| 9 | 4.3 | 47.1 | 3.7 | 13.9 | 15.5 |
| 21 | 4.0 | 75.9 | 46.5 | 16.1 | 27.3 |
| 26 | 0.7 | 31.5 | 13.2 | 2.3 | 14.1 |
| 29 | 0.7 | 26.7 | 9.7 | 18.2 | 0 |
| 36 | 16.6 | 0 | 10.8 | 1.8 | 11.5 |
| 38 | 2.2 | 34.4 | 13.2 | 15.6 | 18.1 |
| 40 | 9.7 | 18.4 | 19.5 | 17.9 | 0 |
| Comparative Example 1 | 0.8 | 81.2 | 12.4 | 4.3 | 10.0 |
| Comparative Example 2 | 0 | 43.9 | 34.5 | 63.2 | 42.0 |

As shown in Table 4, the compounds of Examples of the present invention display a low activity to inhibit CYP450, suggesting that a risk of causing side effects owing to the interaction among different drugs is very low. More precisely, almost all the compounds of the invention showed as low inhibition rate as 50% at best for CYP 1A2, CYP 2C9, CYP 2C19, CYP 2D6, and CYP 3A4 enzymes. In particular, compared with the compound of Comparative Example 1 (81.2%) that has been used as the conventional anti-diabetic agent that can promote insulin secretion by activating GPR40 protein, the compounds of Examples of the invention demonstrated a significantly lower enzyme inhibiting activity particularly against CYP 2C9. Compared with the compound of Comparative Example 2 (63.2%), the compounds of Examples of the invention demonstrated a comparatively lower enzyme inhibiting activity against CYP 2D6.

Since the novel 3-(4-(benzyloxy)phenyl)hex-4-inoic acid derivative of the present invention has a significantly low CYP enzyme inhibiting effect, a pharmaceutical composition comprising the same as an active ingredient can be co-treated with other drugs and thereby can be efficiently used for the treatment of complications including metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

Experimental Example 4: Oral Glucose Tolerance Test (OGTT) 1

To investigate in vivo hypoglycemic effect of the novel 3-(4-(benzyloxy)phenyl)hex-4-inoic acid derivative of the present invention, the following experiment was performed.

Male Sprague Dawley rats at 8~10 weeks, the diet-induced obesity model, were adapted at least for 7 days. Only healthy animals were selected thereafter, followed by OGTT. After fasting for 16~18 hours, 5 rats per group were randomly selected and orally administered with the compounds prepared in Examples 2, 3, 4, 6, 9, 12, 14, 16, 25, 29, 36, 37, 41, 43, and 44 at the dose of 10 mg/kg each. At this time, 5% polyethyleneglycol (PEG) was orally administered at the same dose to the non-treated group (Vehicle) rats. 30 minutes after the sample administration, glucose (4 g/kg) was orally administered thereto at the dose of 5 ml/kg. Then, blood glucose was measured by using Accu-chek active strip (Roche diagnostic Co.). The time for the measurement was set at 30 minutes before the glucose administration (−30), 0 minute, 20 minutes, 40 minutes, 60 minutes, and 120 minutes after the glucose administration, and blood glucose was measured through tail vein puncture. The results are shown in Table 5.

TABLE 5

| Example | % AUC |
|---|---|
| 2 | 17.2 |
| 3 | 12.5 |
| 4 | 16.2 |
| 6 | 15.2 |
| 9 | 24.7 |
| 12 | 31.0 |
| 14 | 27.7 |
| 16 | 21.1 |
| 25 | 24.6 |
| 29 | 27.1 |
| 36 | 22.6 |
| 37 | 28.5 |
| 41 | 23.7 |
| 43 | 21.2 |
| 44 | 22.8 |
| Comparative Example 1 | 16.2 |

As shown in Table 5, the compounds of the invention displayed 21.9% of hypoglycemic effect by that of the non-treated group, suggesting that they had excellent in vivo glucose lowering effect. More precisely, the compound of Comparative Example 1, known as the conventional GPR40 protein activator, was confirmed to have as high the hypoglycemic effect as 16.2%, while the compounds of Examples of the invention demonstrated higher hypoglycemic effect than that. In particular, the hypoglycemic effects of those compounds of Examples 9, 12, 14, 29, and 37 were respectively 24.7%, 31.0%, 27.7%, 27.1%, and 28.5%, indicating that their activity to lower blood glucose was excellent, compared with that of the compound of Comparative Example 1.

Therefore, it was confirmed that the novel 3-(4-(benzyloxy)phenyl)hex-4-inoic acid derivative of the present invention has excellent effect to activate GPR 40 protein and accordingly has significant effect of lowering blood glucose by promoting insulin secretion. Thus, the composition comprising the same as an active ingredient can be efficiently used as a pharmaceutical composition for the treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

Experimental Example 5: Oral Glucose Tolerance Test (OGTT) 2

To investigate in vivo hypoglycemic effect of the novel 3-(4-(benzyloxy)phenyl)hex-4-inoic acid derivative of the present invention, the following experiment was performed.

Male Goto-Kakizaki (GK) rats at 22~23 weeks, the type II diabetes animal model (not obesity), were adapted at least for 7 days. Only healthy animals were selected thereafter, followed by OGTT. After fasting for 16~18 hours, 5 rats per group were randomly selected and orally administered with the compounds prepared in Examples 5, 9, 14, 28, 37, and 47 at the dose of 0.3~10 mg/kg. At this time, 5% polyethyleneglycol (PEG) was orally administered at the same dose to the non-treated group rats. 60 minutes after the sample administration, glucose (4 g/kg) was orally administered thereto at the dose of 5 ml/kg. Then, blood glucose was measured by using Accu-chek active strip (Roche diagnostic Co.). The time for the measurement was set at 60 minutes before the glucose administration (−60), 0 minute, 20 minutes, 40 minutes, 60 minutes, and 120 minutes after the glucose administration, and blood glucose was measured through tail vein puncture. The results are shown in Table 6.

TABLE 6

| Example | Dose (mg/kg) | % AUC |
|---|---|---|
| 5 | 0.3 | C |
|  | 1 | C |
|  | 3 | C |
|  | 10 | B |
| 9 | 0.3 | C |
|  | 1 | C |
|  | 3 | A |
|  | 10 | A |
| 14 | 0.3 | C |
|  | 1 | C |
|  | 3 | B |
|  | 10 | B |
| 28 | 0.3 | C |
|  | 1 | C |
|  | 3 | C |
|  | 10 | B |
| 37 | 0.3 | C |
|  | 1 | B |
|  | 3 | B |
|  | 10 | A |
| 47 | 0.3 | C |
|  | 1 | C |
|  | 3 | B |
|  | 10 | B |
| Comparative Example 1 | 10 | B |

In Table 6,
A: over 35.0%;
B: 25.0-35.0%; and
C: under 25.0%.

As shown in Table 6, the compounds of Examples of the invention demonstrated at least average 30.0% of hypoglycemic effect by that of the non-treated group at the same dose of the compound of Comparative Example 1 (10 mg/kg). More precisely, the compound of Comparative Example 1 displayed 25.3% (B) of hypoglycemic effect at the dose of 10 mg/kg, while the compounds of Examples 5, 9, 14, 28, 37, and 47 demonstrated similar hypoglycemic effect at the dose of 3 mg/kg to that of the compound of Comparative Example 1. In particular, the compounds of Examples 9 and 37 displayed more than 35.0% of hypoglycemic effect at the dose of 10 mg/kg, which was significantly high, compared with that of the compound of Comparative Example 1.

Therefore, it was confirmed that the novel 3-(4-(benzyloxy)phenyl)hex-4-inoic acid derivative of the present invention has excellent effect to activate GPR40 protein and accordingly has significant effect of lowering blood glucose by promoting insulin secretion. Thus, the composition comprising the same as an active ingredient can be efficiently used as a pharmaceutical composition for the treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

Experimental Example 6: Oral Glucose Tolerance Test (OGTT) 3

To investigate in vivo hypoglycemic effect of the novel 3-(4-(benzyloxy)phenyl)hex-4-inoic acid derivative of the present invention, the following experiment was performed.

Male OLETF (Otsuka Long-Evans Tokushima fatty) rats at 29~30 weeks, the type II diabetes animal model (obesity), were adapted at least for 7 days. Only healthy animals were selected thereafter, followed by OGTT. After fasting for 16~18 hours, 5 rats per group were randomly selected and orally administered with the compounds prepared in Examples 5, 9, 14, 28, 37, and 47 at the dose of 1~10 mg/kg. At this time, 5% polyethyleneglycol (PEG) was orally administered at the same dose to the non-treated group rats. 60 minutes after the sample administration, glucose (4 g/kg) was orally administered thereto at the dose of 5 ml/kg. Then, blood glucose was measured by using Accu-chek active strip (Roche diagnostic Co.). The time for the measurement was set at 60 minutes before the glucose administration (−60), 0 minute, 20 minutes, 40 minutes, 60 minutes, and 120 minutes after the glucose administration, and blood glucose was measured through tail vein puncture. The results are shown in Table 7.

TABLE 7

| Example | Dose (mg/kg) | % AUC |
|---|---|---|
| 5 | 1 | B |
|  | 3 | B |
|  | 10 | A |
| 9 | 1 | B |
|  | 3 | A |
|  | 10 | A |
| 14 | 1 | C |
|  | 3 | B |
|  | 10 | B |
| 28 | 1 | B |
|  | 3 | B |
|  | 10 | B |
| 37 | 1 | A |
|  | 3 | A |
|  | 10 | A |
| 47 | 1 | C |
|  | 3 | C |
|  | 10 | B |
| Comparative Example 1 | 10 | B |

In Table 7,
A: over 35.0%;
B: 25.0-35.0%; and
C: under 25.0%.

As shown in Table 7, the compounds of Examples of the invention demonstrated at least average 35.0% of hypoglycemic effect, compared with the non-treated group at the same dose of the compound of Comparative Example 1 (10 mg/kg). More precisely, the compound of Comparative Example 1 displayed 31.6% (B) of hypoglycemic effect at the dose of 10 mg/kg, while the compounds of Examples 9 and 37 demonstrated higher hypoglycemic effect at the dose of 1 mg/kg than that of the compound of Comparative Example 1. In particular, the compounds of Examples 9 and 37 displayed more than 35.0% of hypoglycemic effect at the dose of 10 mg/kg, which was significantly high, compared with that of the compound of Comparative Example 1.

Therefore, it was confirmed that the novel 3-(4-(benzyloxy)phenyl)hex-4-inoic acid derivative of the present invention has excellent effect to activate GPR40 protein and accordingly has significant effect of lowering blood glucose by promoting insulin secretion. Thus, the composition comprising the same as an active ingredient can be efficiently used as a pharmaceutical composition for the treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

Experimental Example 7: Measurement of Blood GLP-1 (Glucagon-Like Peptide-1) after the Oral Administration To investigate the blood GLP-1 increasing rate over the oral administration of the novel 3-(4-(benzyloxy)phenyl)hex-4-inoic acid derivative of the invention, the following experiment was performed.

Male Sprague Dawley rats at 10~12 weeks, the diet-induced obesity model, were adapted at least for 7 days. Only healthy animals were selected after the adaptation for the following experiment. After fasting for 16~18 hours, 5 rats per group were randomly selected and orally administered with the compound prepared in Example 9 at the dose of 10~100 mg/kg (volume of administration solvent: 5 ml/kg). At this time, 5% polyethyleneglycol (PEG) was orally administered at the same dose to the non-treated group rats. 60 minutes after the sample administration, glucose was orally administered thereto at the dose of 2 g/kg. 20 minutes later, blood was drawn from the heart (0.5 ml of whole blood). The blood sample was immediately loaded in the sample tube treated with DPP-4 (dipeptidyl peptidase-4) inhibitor and EDTA (ethylenediaminetetraacetic acid), which was placed in an ice vessel for cooling. The blood sample was centrifuged at 3600 rpm for 10 minutes to separate blood plasma. Then, GLP-1 content in the separated blood plasma was measured by using ELISA kit for GLP-1 measurement (Millipore, USA). The results are shown in FIG. 2.

FIG. 2 is a graph illustrating the blood GLP-1 content in SD rat (Sprague Dawley rat) according to the oral-administration of the compounds of Example 9 and Comparative Example 1.

As shown in FIG. 2, the compound of Comparative Example 1 did not display any increase in GLP-1 that can promote insulin secretion after the administration, compared with the group treated with glucose (Veh.). However, the compound of Example 9 was confirmed to increase blood GLP-1 in SD rat.

Therefore, it was confirmed that the novel 3-(4-(benzyloxy)phenyl)hex-4-inoic acid derivative of the present invention has excellent activity to promote the secretion of GLP-1 hormone, compared with the compound of Comparative Example 1 and particularly, this effect is more excellent in diabetes animal models. It is also expected by such activity of promoting GLP-1 secretion for the novel 3-(4-(benzyloxy)phenyl)hex-4-inoic acid derivative of the present invention to be able to prevent functional defect of beta cells and weight gaining. Thus, the composition comprising the novel 3-(4-(benzyloxy)phenyl)hex-4-inoic acid derivative of the present invention as an active ingredient can be efficiently used as a pharmaceutical composition for the treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

In the meantime, the compound represented by formula 1 of the present invention can be formulated in various forms according to the purpose of use. The below is the examples of formulation methods using the compound represented by formula 1 of the present invention as an active ingredient, but the present invention is not limited thereto.

Preparative Example 1: Preparation of Pharmaceutical Formulations

<1-1> Preparation of Powders

| | |
|---|---|
| Compound of Example 1 | 500 mg |
| Lactose | 100 mg |
| Talc | 10 mg |

Powders were prepared by mixing all the above components, which were filled in airtight packs according to the conventional method for preparing powders.

<1-2> Preparation of Tablets

| | |
|---|---|
| Compound of Example 1 | 500 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Compound of Example 1 | 500 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Injectable Solutions

| | |
|---|---|
| Compound of Example 1 | 500 mg |
| Sterilized distilled water | proper amount |
| pH regulator | proper amount |

Injectable solutions were prepared by mixing all the above components, putting the mixture into 2 ml ampoules and sterilizing thereof by the conventional method for preparing injectable solutions.

<1-5> Preparation of Liquid Formulations

| | |
|---|---|
| Compound of Example 1 | 100 mg |
| Isomerized sugar | 10 g |
| Mannitol | 5 g |
| Purified water | proper amount |

All the above components were dissolved in purified water. After adding lemon flavor, total volume was adjusted to be 100 by adding purified water. Liquid formulations were prepared by putting the mixture into brown bottles and sterilizing thereof by the conventional method for preparing liquid formulations.

INDUSTRIAL APPLICABILITY

The novel 3-(4-(benzyloxy)phenyl)hex-4-inoic acid derivative, the optical isomer thereof, or the pharmaceutically acceptable salt thereof of the present invention has excellent activities of activating GPR40 protein and promoting insulin secretion accordingly but has no toxicity when co-administered with other drugs. That is, the novel 3-(4-(benzyloxy)phenyl)hex-4-inoic acid derivative, the optical isomer thereof, or the pharmaceutically acceptable salt thereof of the present invention can be co-administered with other drugs and can promote the activation of GPR40 protein significantly, so that the composition comprising the same as an active ingredient can be efficiently used as a pharmaceutical composition for the prevention and treatment of metabolic disease such as obesity, type I diabetes, type II diabetes, incompatible glucose tolerance, insulin resistance, hyperglycemia, hyperlipidemia, hypertriglyceridemia, hypercholesterolemia, dyslipidemia, and syndrome X, etc.

What is claimed is:

1. A compound represented by the below formula 1, an optical isomer thereof, or a pharmaceutically acceptable salt thereof:

[Formula 1]

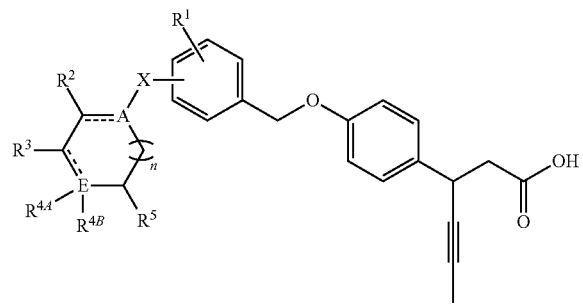

wherein, $\mathrel{\overline{\overline{\phantom{=}}}}$ is single bond or double bond;
A and E are independently C or N;
n is an integer of 0-1;
X is a single bond, or $C_{1-3}$ straight or branched alkylene;
$R^1$ is —H, or

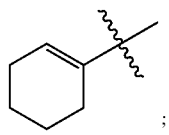 [SMILES: *C1=CCCCC1]

;

$R^2$ is —H, or can form phenyl with $R^3$;
$R^3$ is —H, or can form a phenyl group with $R^2$, or can form a phenyl group with $R^{4A}$, wherein the phenyl group formed between $R^3$ and $R^{4A}$ can be substituted with methoxy;
$R^{4A}$ is —H, —OH, =O,

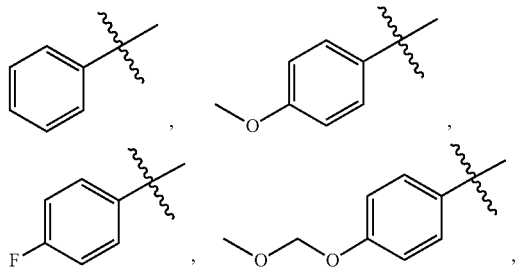

101
-continued

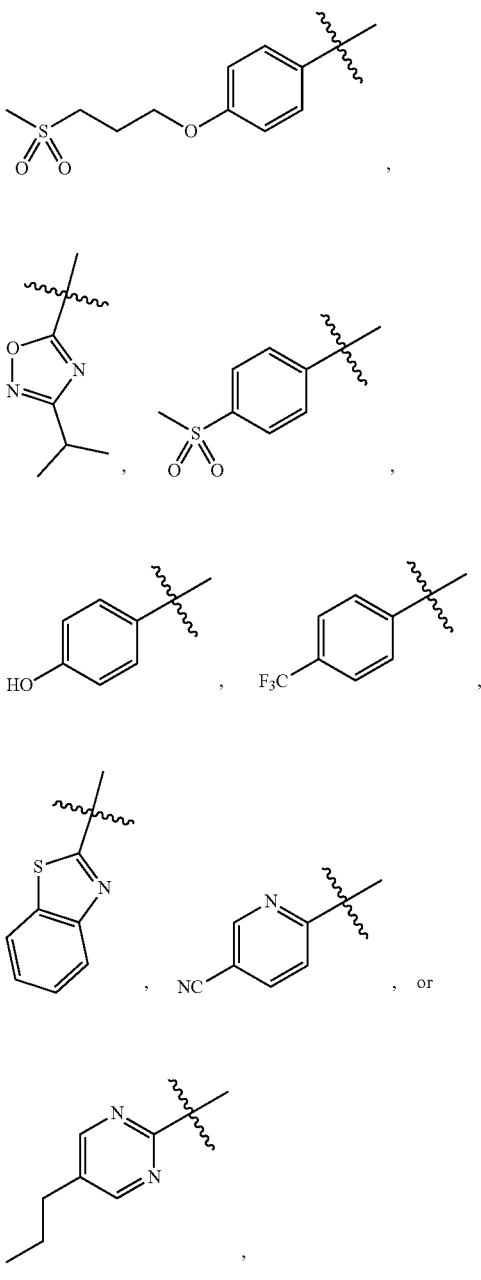

or R³ and R⁴ᴬ can form a phenyl group, wherein the phenyl group can be substituted with methoxy;

R⁴ᴮ is absent, —H, or can form

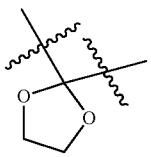 [SMILES: *C1(*)OCCO1]

along with atoms which are conjugated to the same and R⁴ᴬ;

102

$R^5$ is —H; and
wherein when A is N, then the compound has a formula

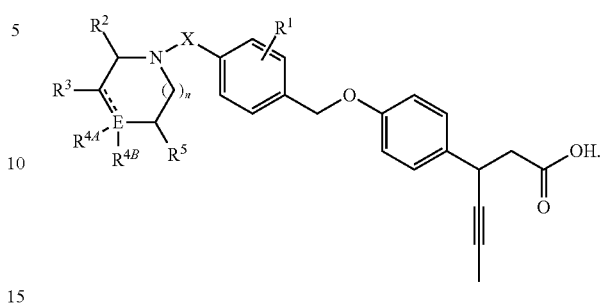

2. The compound represented by formula 1, the optical isomer thereof, or the pharmaceutically acceptable salt thereof according to claim 1, wherein the compound represented by formula 1 is selected from the group consisting of the following compounds:

(1) 3-(4-(3-(1,4-dioxaspiro[4,5]dec-7-en-8-yl)benzyloxy)phenyl)hex-4-ynoic acid;
(2) L-lysine 3-(4-(3-(1,4-dioxaspiro[4,5]dec-7-en-8-yl)benzyloxy)phenyl)hex-4-ynoate;
(3) 4-(4-(3-(1,4-dioxaspiro[4,5]dec-7-en-8-yl)benzyloxy)phenyl)hex-4-ynoic acid;
(4) 3-(4-(3-(4-oxocyclohex-1-enyl)benzyloxy)phenyl)hex-4-ynoic acid;
(5) 3-(4-(3-(4-hydroxycyclohex-1-enyl)benzyloxy)phenyl)hex-4-ynoic acid;
(6) L-lysine 3-(4-(3-(4-hydroxycyclohex-1-enyl)benzyloxy)phenyl)hex-4-ynoate;
(7) (3S)-3-(4-(3-(1,4-dioxaspiro[4,5]dec-7-en-8-yl)benzyloxy)phenyl)hex-4-ynoic acid;
(8) (3R)-3-(4-(3-(1,4-dioxaspiro[4,5]dec-7-en-8-yl)benzyloxy)phenyl)hex-4-ynoic acid;
(9) L-lysine (3S)-3-(4-(3-(1,4-dioxaspiro[4,5]dec-7-en-8-yl)benzyloxy)phenyl)hex-4-ynoate;
(10) L-lysine (3R)-3-(4-(3-(1,4-dioxaspiro[4,5]dec-7-en-8-yl)benzyloxy)phenyl)hex-4-ynoate L-lysinate;
(11) sodium (3S)-3-(4-(3-(1,4-dioxaspiro[4,5]dec-7-en-8-yl)benzyloxy)phenyl)hex-4-ynoate
(12) 3-(4-(4-((3,4-dihydroisoquinoline-2(1H)-yl)methyl)benzyloxy) phenyl)hex-4-ynoic acid;
(13) 3-(4-(3-cyclohexenyl-4-((3,4-dihydroisoquinoline-2(1H)-yl)methyl)benzyloxy)phenyl)hex-4-ynoic acid;
(14) 3-(4-(4-((4-phenyl-5,6-dihydropyridine-1(2H)-yl)methyl) benzyloxy)phenyl)hex-4-ynoic acid;
(15) 3-(4-(4-((4-phenylpiperazine-1-yl)methyl)benzyloxy)phenyl)hex-4-ynoic acid;
(16) 3-(4-(4-((6-methoxy-3,4-dihydroisoquinoline-2(1H)-yl)methyl) benzyloxy)phenyl)hex-4-ynoic acid;
(17) 3-(4-(4-((4-phenylpiperidine-1-yl)methyl)benzyloxy)phenyl)hex-4-ynoic acid;
(18) 3-(4-(4-((4-(4-fluorophenyl)piperazine-1-yl)methyl)benzyloxy) phenyl)hex-4-ynoic acid;
(19) 3-(4-(4-((4-(4-(trifluoromethyl)phenyl)piperazine-1-yl)methyl) benzyloxy)phenyl)hex-4-ynoic acid;
(20) 3-(4-(4-((4-(4-(3-(methylsulfonyl)propoxy)phenyl)piperazine-1-yl)methyl)benzyloxy)phenyl)hex-4-ynoic acid;
(21) (S)-3-(4-(4-((3,4-dihydroisoquinoline-2(1H)-yl)methyl) benzyloxy)phenyl)hex-4-ynoic acid;
(22) (S)-3-(4-(4-((4-(4-(trifluoromethyl)phenyl)piperazine-1-yl)methyl)benzyloxy)phenyl)hex-4-ynoic acid;
(23) (S)-3-(4-(4-((4-(4-fluorophenyl)piperazine-1-yl)methyl)benzyloxy)phenyl)hex-4-ynoic acid;

(24) potassium (S)-3-(4-(4-((4-(4-(trifluoromethyl)phenyl)piperazine-1-yl)methyl)benzyloxy)phenyl)hex-4-ynoate;
(25) (S)-3-(4-(4-((6-methoxy-3,4-dihydroisoquinoline-2 (1H)-yl)methyl)benzyloxy)phenyl)hex-4-ynoic acid;
(26) (S)-3-(4-(4-((4-phenylpiperidine-1-yl)methyl)benzyloxy)phenyl)hex-4-ynoic acid;
(27) (S)-3-(4-(4-(isoindoline-2-ylmethyl)benzyloxy)phenyl)hex-4-ynoic acid;
(28) (S)-3-(4-(4-((4-phenyl-5,6-dihydropyridine-1(2H)-yl)methyl)benzyloxy)phenyl)hex-4-ynoic acid;
(29) (S)-3-(4-(4-((4-(4-(methoxymethoxy)phenyl)piperazine-1-yl)methyl)benzyloxy)phenyl)hex-4-ynoic acid;
(30) (S)-3-(4-(4-((4-(5-isopropyl-1,2,4-oxadiazole-3-yl)piperidine-1-yl)methyl)benzyloxy)phenyl)hex-4-ynoic acid;
(31) (S)-3-(4-(4-((4-(5-isopropyl-1,2,4-oxadiazole-3-yl)piperazine-1-yl)methyl)benzyloxy)phenyl)hex-4-ynoic acid;
(32) (S)-3-(4-(4-((4-(4-(methylsulfonyl)phenyl)-5,6-dihydropyridine-1(2H)-yl)methyl)benzyloxy)phenyl)hex-4-ynoic acid;
(33) (S)-3-(4-(4-((4-(4-(3-(methylsulfonyl)propoxy)phenyl)-5,6-dihydropyridine-1(2H)-yl)methyl)benzyloxy)phenyl)hex-4-ynoic acid;
(34) (3S)-3-(4-(4-(1-(3,4-dihydroisoquinoline-2(1H)-yl)ethyl)benzyloxy)phenyl)hex-4-ynoic acid;
(35) (S)-3-(4-(4-((4-(4-hydroxyphenyl)piperazine-1-yl)methyl)benzyloxy)phenyl)hex-4-ynoic acid;
(36) (S)-3-(4-(4-((4-(4-(3-(methylsulfonyl)propoxy)phenyl)piperazine-1-yl)methyl)benzyloxy)phenyl)hex-4-ynoic acid;
(37) sodium (S)-3-(4-(4-(isoindoline-2-ylmethyl)benzyloxy)phenyl)hex-4-ynoate;
(38) L-lysine (S)-3-(4-(4-(isoindoline-2-ylmethyl)benzyloxy)phenyl)hex-4-ynoate;
(39) (S)-3-(4-(4-((4-(4-fluorophenyl)-5,6-dihydropyridine-1(2H)-yl)methyl)benzyloxy)phenyl)hex-4-ynoic acid;
(40) (S)-3-(4-(4-((4-(4-methoxyphenyl)piperazine-1-yl)methyl)benzyloxy)phenyl)hex-4-ynoic acid;
(41) sodium (S)-3-(4-(4-((3,4-dihydroquinoline-1(2H)-yl)methyl)benzyloxy)phenyl)hex-4-ynoate;
(42) potassium (S)-3-(4-(4-((3,4-dihydroquinoline-1(2H)-yl)methyl)benzyloxy)phenyl)hex-4-ynoate;
(43) (S)-3-(4-(4-((4-(benzo[d]thiazole-2-yl)piperazine-1-yl)methyl)benzyloxy)phenyl)hex-4-ynoic acid;
(44) (S)-3-(4-(4-((4-(5-propylpyrimidine-2-yl)piperazine-1-yl)methyl)benzyloxy)phenyl)hex-4-ynoic acid;
(45) (S)-3-(4-(4-((4-(5-cyanopyridine-2-yl)piperazine-1-yl)methyl)benzyloxy)phenyl)hex-4-ynoic acid;
(46) (3S)-3-(4-(4-((3-phenylpyrrolidine-1-yl)methyl)benzyloxy)phenyl)hex-4-ynoic acid;
(48) (S)-3-(4-(4-(2-(6-methoxy-3,4-dihydroisoquinoline-2(1H)-yl)ethyl)benzyloxy)phenyl)hex-4-ynoic acid;
(49) (S)-3-(4-(4-(2-(isoindoline-2-yl)ethyl)benzyloxy)phenyl)hex-4-ynoic acid;
(50) (S)-3-(4-(4-(2-(3,4-dihydroisoquinoline-2(1H)-yl)ethyl)benzyloxy)phenyl)hex-4-ynoic acid; and
(51) sodium (S)-3-(4-(4-((6-methoxy-3,4-dihydroisoquinoline-2(1H)-yl)methyl)benzyloxy)phenyl)hex-4-ynoate.

3. A method for preparing the compound represented by formula 1 of claim 1 comprising the following steps as shown in the below reaction formula 1:

preparing the compound represented by formula 4 by condensation reaction of the compound represented by formula 2 and the compound represented by formula 3 (step 1); and preparing the compound represented by formula 1 by reduction reaction of the compound represented by formula 4 prepared in step 1 (step 2);

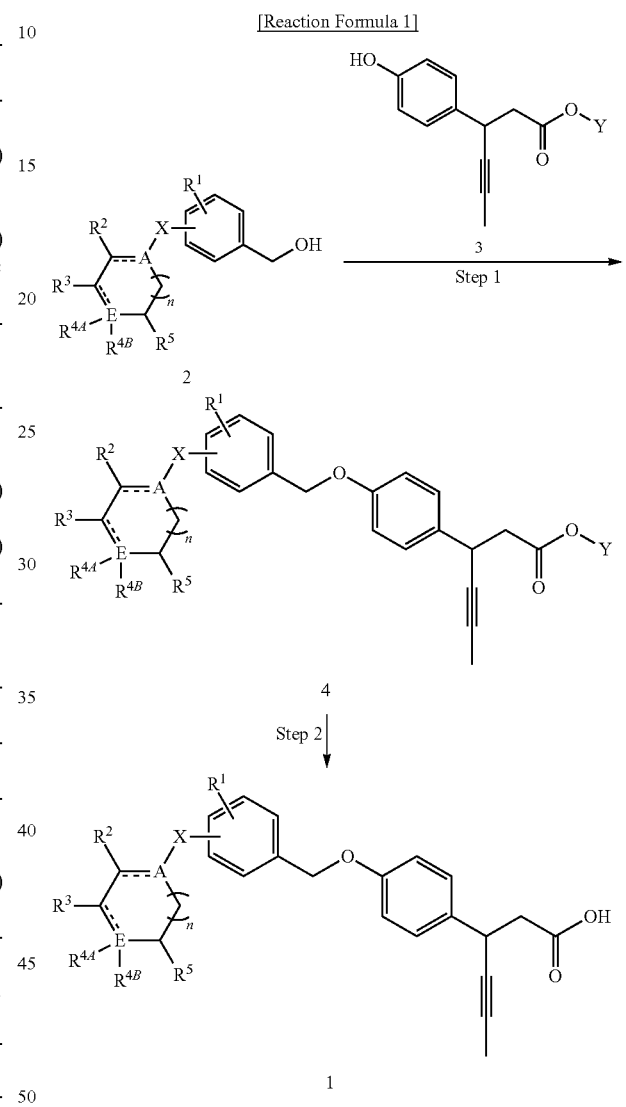

[Reaction Formula 1]

and in reaction formula 1, $R^1$, $R^2$, $R^3$, $R^{4A}$, $R^{4B}$, $R^5$, A, E, n, ═══, and X are as defined in formula 1; and Y is $C_{1-10}$ straight or branched alkyl.

4. A method for preparing the compound represented by formula 1 of claim 1, in which the compound represented by formula 2 is prepared by the method comprising the following steps, as shown in the below reaction formula 2:

preparing the compound represented by formula 10 by reacting the compound represented by formula 8 and the compound represented by formula 9 (step 1);

preparing the compound represented by formula 12 by reacting the compound represented by formula 10 prepared in step 1 and the compound represented by formula 11 (step 2); and preparing the compound represented by formula 2 by reduction reaction of the compound represented by formula 12 prepared in step 2 (step 3);

[Reaction Formula 2]

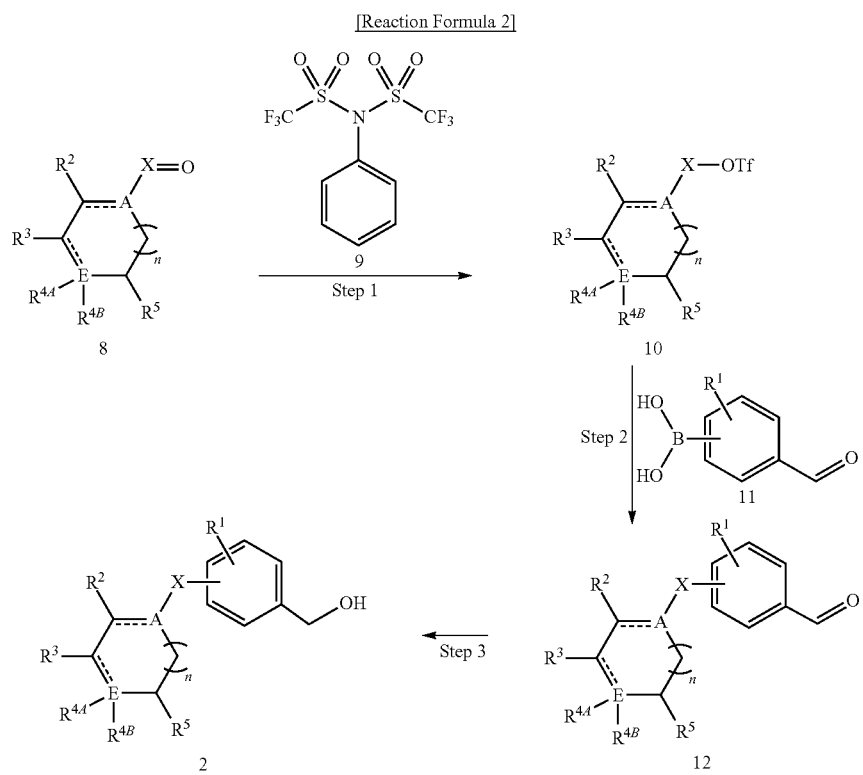

and in reaction formula 2, $R^1$, $R^2$, $R^3$, $R^{4A}$, $R^{4B}$, $R^5$, A, E, n, ⇌, and X are as defined in formula 1; and -OTf is trifluoromethanesulfonate.

5. A method for preparing the compound represented by formula 1 of claim 1 comprising the following steps as shown in the below reaction formula 3:
   preparing the compound represented by formula 6 by coupling reaction of the compound represented by formula 5 and the compound represented by formula 3 (step 1);
   preparing the compound represented by formula 7 by mesylate reaction of the compound represented by formula 6 prepared in step 1 (step 2);
   preparing the compound represented by formula 4 by replacing the mesylate site of the compound represented by formula 7 prepared in step 2 with the compound represented by formula 13 (step 3); and
   preparing the compound represented by formula 1 by reduction reaction of the compound represented by formula 4 prepared in step 3 (step 4)

[Reaction Formula 3]

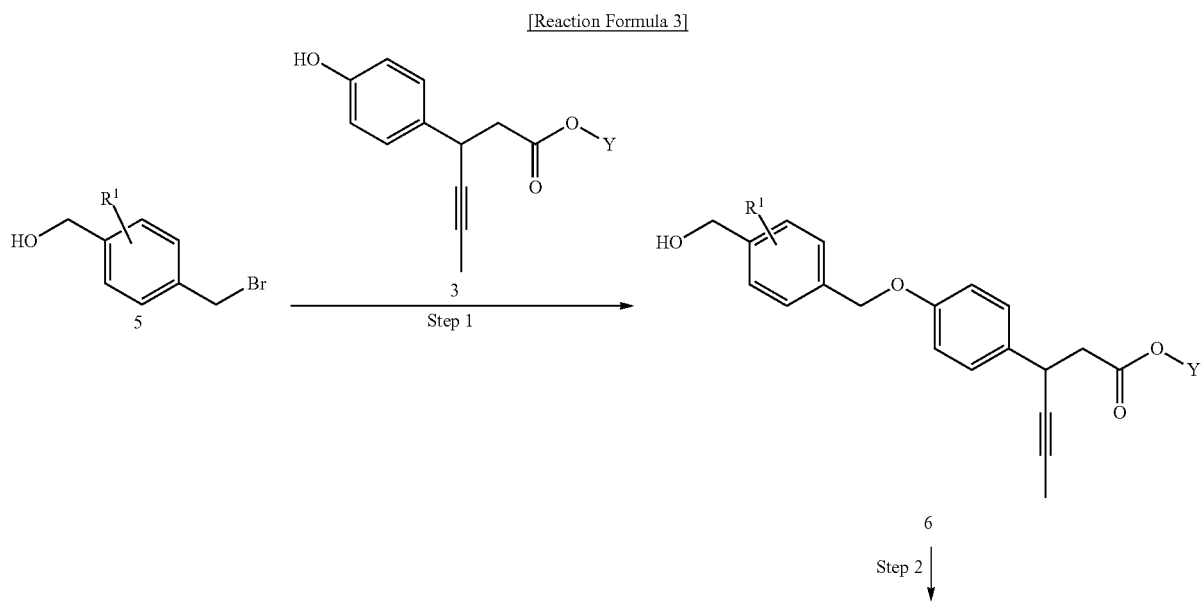

-continued

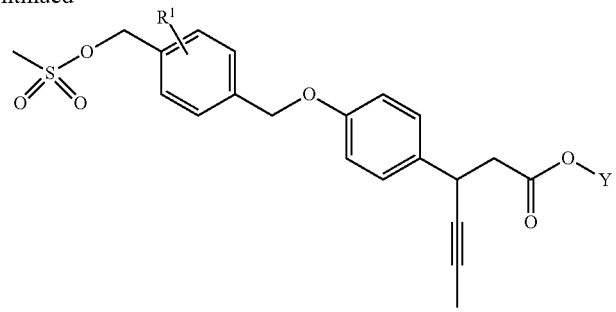

7

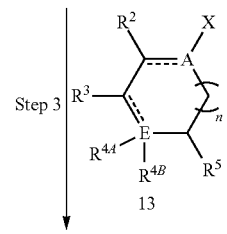

Step 3

13

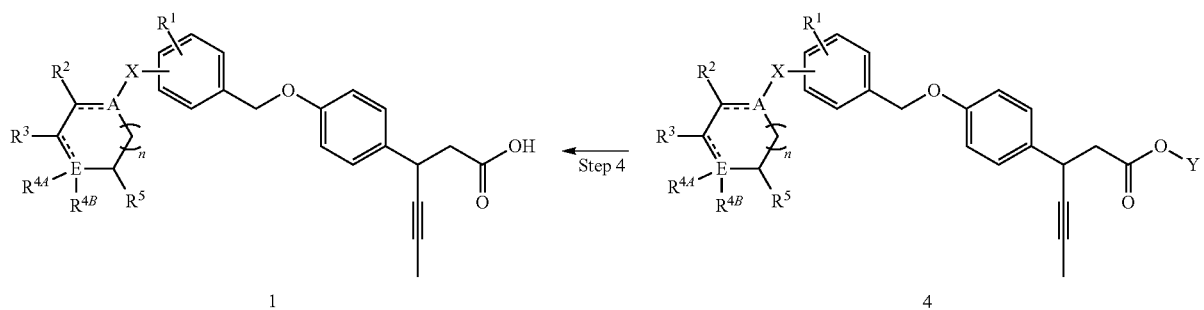

and in reaction formula 3, $R^1$, $R^2$, $R^3$, $R^{4A}$, $R^{4B}$, $R^5$, A, E, n, ═, and X are as defined in formula 1; and Y is $C_{1-10}$ straight or branched alkyl.

6. A method for preparing the compound represented by formula 1 of claim 1 containing the step of preparing the compound represented by formula 1b by ring-opening reaction of the compound represented by formula 1a (step 1) as shown in the below reaction formula 4:

[Reaction Formula 4]

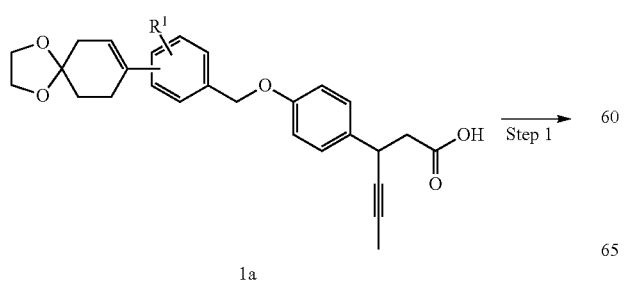

1a

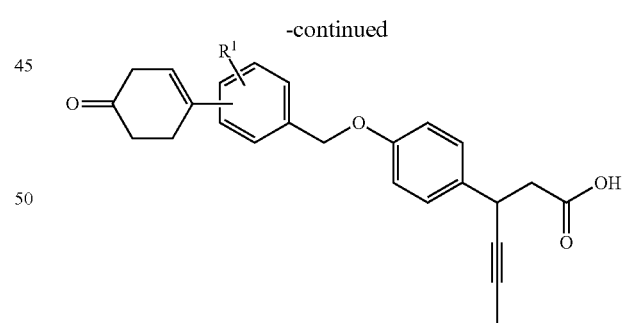

1b and in reaction formula 4, $R^1$ is as defined in formula 1; and the compounds represented by formula 1a and formula 1b are included in the compound represented by formula 1.

7. A method for preparing the compound represented by formula 1 of claim 1 containing the step of preparing the compound represented by formula 1c by reduction reaction of the compound represented by formula 1b (step 1) as shown in the below reaction formula 5:

[Reaction Formula 5]

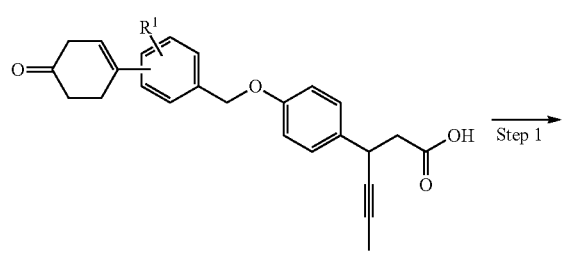

1b

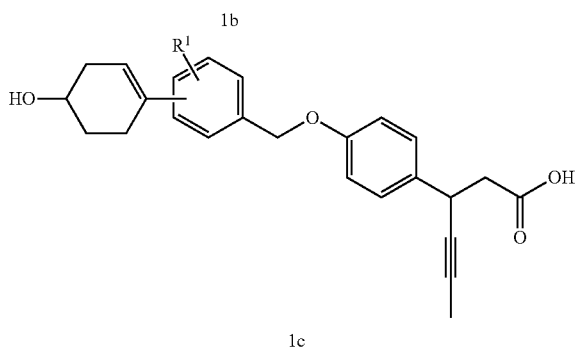

1c and in reaction formula 5, R¹ is as defined in formula 1; and the compounds represented by formula 1b and formula 1c are included in the compound represented by formula 1.

8. A pharmaceutical composition comprising the compound represented by formula 1 of claim 1, the optical isomer thereof, or the pharmaceutically acceptable salt thereof as an active ingredient for the prevention or treatment of metabolic disease.

9. A method of treating metabolic disease comprising administering a pharmaceutically effective amount of the compound represented by formula 1 of claim 1, the optical isomer thereof, or the pharmaceutically acceptable salt thereof to a subject in need thereof.

10. The method of claim 9, wherein the metabolic disease is obesity, type I diabetes, type II diabetes, incompatible glucose tolerance, insulin resistance, hyperglycemia, hyperlipidemia, hypertriglyceridemia, hypercholesterolemia, dyslipidemia, and syndrome X.

11. A compound having a structure:

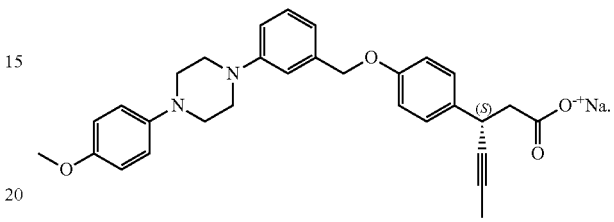

12. A pharmaceutical composition comprising the compound of claim 11 or the optical isomer thereof as an active ingredient for the prevention or treatment of metabolic disease.

13. A method of treating metabolic disease comprising administering a pharmaceutically effective amount of the compound of claim 11 or the optical isomer thereof to a subject in need thereof.

14. The method of claim 13, wherein the metabolic disease is obesity, type I diabetes, type II diabetes, incompatible glucose tolerance, insulin resistance, hyperglycemia, hyperlipidemia, hypertriglyceridemia, hypercholesterolemia, dyslipidemia, and syndrome X.

* * * * *